US009366667B2

(12) United States Patent
Lipkin et al.

(10) Patent No.: US 9,366,667 B2
(45) Date of Patent: Jun. 14, 2016

(54) PISCINE REOVIRUS DIAGNOSTIC COMPOSITIONS

(75) Inventors: W. Ian Lipkin, New York, NY (US); Gustavo Palacios, New York, NY (US); Ruth Toril Kongtorp, Oslo (NO); Edgar Brun, Oslo (NO)

(73) Assignees: THE TRUSTEES OF COLUMBIA UNIVERSITY IN THE CITY OF NEW YORK, New York, NY (US); THE NATIONAL VETERINARY INSTITUTE, Oslo (NO)

( * ) Notice: Subject to any disclaimer, the term of this patent is extended or adjusted under 35 U.S.C. 154(b) by 0 days.

(21) Appl. No.: 13/499,867

(22) PCT Filed: Oct. 4, 2010

(86) PCT No.: PCT/US2010/051348

§ 371 (c)(1), (2), (4) Date: Nov. 21, 2012

(87) PCT Pub. No.: WO2011/041790

PCT Pub. Date: Apr. 7, 2011

(65) Prior Publication Data

US 2013/0072542 A1 Mar. 21, 2013

Related U.S. Application Data

(60) Provisional application No. 61/325,047, filed on Apr. 16, 2010, provisional application No. 61/380,594, filed on Sep. 7, 2010.

(51) Int. Cl.

| | |
|---|---|
| ***G01N 33/53*** | (2006.01) |
| ***A61K 31/7088*** | (2006.01) |
| ***A61K 39/15*** | (2006.01) |
| ***C07K 14/005*** | (2006.01) |
| ***C07K 16/10*** | (2006.01) |
| ***A61K 39/12*** | (2006.01) |

(52) U.S. Cl.

CPC ........ *G01N 33/5308* (2013.01); *A61K 31/7088* (2013.01); *A61K 39/12* (2013.01); *A61K 39/15* (2013.01); *C07K 14/005* (2013.01); *C07K 16/10* (2013.01); *C12N 2720/12022* (2013.01); *C12N 2720/12034* (2013.01)

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,737,323 | A | 4/1988 | Martin et al. |
| 4,833,092 | A | 5/1989 | Geysen |
| 4,837,028 | A | 6/1989 | Allen |
| 4,946,778 | A | 8/1990 | Ladner et al. |
| 5,670,367 | A | 9/1997 | Dorner et al. |
| 6,471,964 | B1 | 10/2002 | Biering et al. |
| 2003/0148443 | A1 * | 8/2003 | Zhao et al. .................. 435/69.1 |
| 2006/0014225 | A1 | 1/2006 | Georges et al. |
| 2006/0165698 | A1 | 7/2006 | Butzke et al. |
| 2007/0271630 | A1 | 11/2007 | Boukharov et al. |
| 2008/0025662 | A1 | 1/2008 | Kondo et al. |
| 2008/0124793 | A1 | 5/2008 | Duncan |
| 2008/0226602 | A1 | 9/2008 | Coffey |
| 2013/0072542 | A1 * | 3/2013 | Lipkin et al. ............... 514/44 A |

FOREIGN PATENT DOCUMENTS

| | | | |
|---|---|---|---|
| GB | 2188638 | A | 10/1987 |
| WO | WO-84/03564 | A1 | 9/1984 |
| WO | WO-86/06487 | A1 | 11/1986 |
| WO | WO-97/06243 | A1 | 2/1997 |
| WO | WO-99/58639 | A2 | 11/1999 |
| WO | WO-01/09340 | A1 | 2/2001 |
| WO | WO-01/10469 | A2 | 2/2001 |
| WO | WO-01/68865 | A2 | 9/2001 |
| WO | WO-2005/121325 | | 12/2005 |
| WO | WO-2008/106803 | | 9/2008 |
| WO | WO-2011/041789 | | 4/2011 |

OTHER PUBLICATIONS

Subramanian et al. Journal of Clinical Microbiology. Jun. 1993; 31(6): 1612-1614).*

Sequence alignment of instant SEQ ID No. 2 with GenEmbl database access No. GU994022, submitted by Palacios et al. on Jul. 27, 2010.*

Sequence alignment of SEQ ID No. 39 with the deduced amino acid sequence from the sequence alignment of instant SEQ ID No. 2 with GenEmbl database access No. GU994022.*

Sequence alignment of SEQ ID No. 40 with the deduced amino acid sequence from the sequence alignment of instant SEQ ID No. 2 with GenEmbl database access No. GU994022.*

Koop et al., "A salmonid EST genomic study: genes, duplications, phylogeny and microarrays," BMC Genomics 9:545 (2008) 16 pages.

Danish Search Report issued for Danish application PA 2011 70227, dated Jul. 4, 2013, 2 pages.

"*Reovirus* sp. Salmo/GP-2010/NOR segment S3, partial sequence", GenBank accession No. GU994020.1, Jul. 27, 2010, 2 pages.

Watanabe, K., et al., "Virus-like particles associated with heart and skeletal muscle inflammation (HSMI)", Diseases of Aquatic Organisms, 2006, vol. 70, pp. 183-192.

(Continued)

*Primary Examiner* — Shanon A Foley

(74) *Attorney, Agent, or Firm* — Leason Ellis LLP

(57) ABSTRACT

The invention is directed to a isolated a Piscine reovirus associated with HSMI in teleosts, and isolated nucleic acids sequences and peptides thereof. The invention also relates to diagnostic antibodies against antigens derived from Piscine reoviruses. In another aspect, the invention relates to iRNAs which target nucleic acid sequences of Piscine reoviruses. In another aspect, the invention is related to methods for detecting the presence or absence of Piscine reoviruses in an animal.

8 Claims, 24 Drawing Sheets

(56) References Cited

OTHER PUBLICATIONS

GenBank_EG879913, EST__ssal_eve_23282 ssaleve thyroid Salmo salar cDNA Salmo salar CDNA clone ssal_eve_531_277_ Fwd 5-, mRNA sequence. Nov. 20, 2008.
Internatioanl Search Report and written Opinion mailed on Feb. 22, 2011 for International Application No. PCT/US10/51348 filed Oct. 4, 2010 (11 pages).
Internatioanl Search Report and written Opinion mailed on Feb. 28, 2011 for International Application No. PCT/US10/51346 filed Oct. 4, 2010 (14 pages).
Swiss-Prot_O72469, Non Structural protein sigma NS, Oct. 31, 2006.
Zeng et al. Swiss-Prot Accession No. AOFKT9 "Lambda-1 protein" direct submission, Nov. 28, 2006.
Supplementary EP Search Report issued Jun. 7, 2013 for EP Patent Application No. 10821407.3, 17 pages.
Palacios, Gustavo, et al., "Heart and Skeletal Muscle Inflammation of Farmed Salmon is Associated with Infection with a Novel Reovirus", PLoS ONE, Jul. 2010, vol. 5, No. 7, pp. 1-7.
Kongtorp, R. T., et al., "Studies with experimental transmission of heart and skeletal muscle inflammation in Atlantic salmon, *Salmo salar* L.", Journal of Fish Diseases, 2009, vol. 32, pp. 253-262.
Mikalsen, Aase B., et al., "Atlantic Samon Reovirus Infection Causes a CD8 T Cell Myocarditis in Atlantic Salmon (*Salmo salar* L.)", PloS ONE, Jun. 2012, vol. 7, No. 6, pp. 1-11.
Al-Harbi, A. H. et al., "Purification of macroglobulings from the serum, and Skin and gut mucus of turbot (*Scophthalmus maximus* L.) Immunized with lipopolysaccharide (LPS) from a Fish-pathogenic Cytophaga-like bacterium (CLB)," Bulletin of the European Association of Fish Pathologists, vol. 13, No. 2, pp. 40-44, 6 pages (1993).
Altschul, S. F. et al., Basic local alignment search tool, J. Mol. Biol., vol. 215, pp. 403-410 (1990).
Altschul, S. F. et al., "Gapped BLAST and PSI-BLAST: a new generation of protein database search programs," Nucleic Acids Research, vol. 25, No. 17, pp. 3389-3402 (1977).
Anderson, M. L. M. et al., "Quantitive Filter Hybridisation," Nucleic Acid Hybridization: A Practical Approach, pp. 73-111, 47 pages (1985).
Attoui, H. et al., "Common evolutionary origin of aquareoviruses and orthoreoviruses revealed by genome characterization of Golden shiner reovirus, Grass carp reovirus, Striped bass reovirus and golden ide reovirus (genus *Aquareovirus*, family Reoviridae)," J. Gen. Virol., vol. 83, pp. 1941-1951 (2002).
Ausubel, F. M. et al., "Current Protocols in Molecular Biology," vol. 1, John Wiley & Sons, Inc. NY, NY, 17 pages (1987-2001).
Barton, K. A. et al., "Regeneration of Intact Tobacco Plants Containing Full Length Copies of Genetically Engineered T-DNA, and Transmission of T-DNA to R1 Progeny," Cell, vol. 32, pp. 1033-1043 (Apr. 1983).
Boder, E. T. et al., "Yeast surface display for screening combinatorial polypeptide libraries," Nature Biotechnology, vol. 15, pp. 553-557 (Jun. 1997).
Bornstein, P. et al., "The Chemistry and Biology of Collagen," The Proteins, vol. IV, Academic Press, New York, 222 pages (1979).
Bovarnick, M. R. et al., "The Influence of Certain Salts, Amino Acids, Sugars, and Proteins on the Stability of Rickettsiae," J. Bacteriology, vol. 59, pp. 509-522 (Jan. 13, 1950).
Carlsson, A. et al., "Purification of Infectious Pancreatic Necrosis Virus of Anion Exchange Chromatography Increases the Specific Infectivity," Journal of Virological Methods, vol. 47, No. 1-2, pp. 27-35 (Apr. 1994).
Chen, W. et al., "Cell-Surface Display of Heterologous Proteins: From High-Throughput Screening to Environmental Applications," Biotechnol. Bioeng., vol. 79, No. 5, pp. 496-503 (Sep. 5, 2002).
Clark, T. G. et al., "Developmental expression of surface antigen genes in the parasitic cilate Ichtyophthirius multifiliis," Proc. Natl. Acad. Sci. USA, vol. 89, No. 14, pp. 6363-6367 (Jul. 15, 1992).
Coligan, J. E. et al., "Current Protocols in Protein Science," vol. 1, John Wiley and Sons, Inc., 13 pages (1997-2009).
Corbeil, S. et al., "Evaluation of the protective immunogenicity of the N, P, M, NV, G proteins of infectious hematopoietic necrosis virus in rainbow trout *Oncorhynchus mykiss* using DNA vaccines," Dis. Aquat. Organ., vol. 39, No. 1, pp. 29-26 (1999).
Cox-Foster, D. L. et al., "A metagenomic survey of microbes in honey bee colony collapse disorder," Science, vol. 318, pp. 282-287 (2007).
Danilova, N. et al., "Immunoglobulin variable-region diversity in the zebrafish," Immunogenetics, vol. 52, No. 1-2, pp. 81-91 (Nov. 2000).
Dayhoff, Margaret O., "Atlas of protein sequence and structure," vol. 5, Supplement 3, National Biomedical Research Foundation, Washington D.C., 4 pages (1978).
Devereux, J. et al., "A comprehensive set of sequence analysis programs for the VAX," Nucleic Acids Research, vol. 12, No. 1, pp. 387-395 (1984).
Donnelly, J. J. et al., "Immunication with polnucleotides: a novel approach to vaccination," The Immunologist, vol. 2, pp. 20-26 (1993).
Eliassen T. M. et al., "Isolation of heart and poster skeletal muscle inflammation virus (HSMIV) from salmon," 6th International Symposium on Viruses of Lower Vertebrates, Hokkaido, Japan, 1 page (2004).
Engelbrecht, M. et al., "Association between immunisation, reduced weight gain and plasma cortisol concentrations in juvenile Baltic salmon (*Salmo salar*)," Acta Vet. Scand., vol. 38, No. 3, pp. 275-282 (1997).
Evans, D. A. et al., "Heuristic models of the intermonomeric disulfide bonding process," J. Theor. Biol., vol. 195, No. 4, pp. 505-524 (Dec. 21, 1998).
Feng, D.-F. et al., "Progressive Sequence Alignment as a Prerequisite to Correct Phyogenetic Trees," J. Mol. Evol., vol. 25, pp. 351-360 (1987).
Ferguson, H. W. et al., "An outbreak of disease resembling heart and sketetal muscle inflammation in Scottish farmed salmon, *Salmo salar* L., with observations on myocardial regeneration," J. Fish Dis., vol. 28, pp. 119-123 (2005).
Geysen, H. M. et al., "Strategies for epitope analysis using peptide synthesis," J. Imm. Meth., vol. 102, pp. 259-274 (1987).
Geysen, H. M. et al., "Use of peptide synthesis to probe viral antigens for epitopes to a resolution of a single amino acid," Proc. Natl. Acad. Sci. USA, vol. 81, No. 13, pp. 3998-4002 (Jul. 1984).
Gregersen, Jens.P. "Herstellung von Virussimpfstoffen aus Zelkulturen" Chapter 4.2 in Pharmazeutisce Biotechnology (eds. O. Kayser and R.H. Mueller) Wissenschaftliche Verlagsgesellschaft, Stuttgart, 34 pages (2000).
Hagen, A. J. et al., "Optimization of Poly(ethylene glycol) Precipitation of Hepatitis A Virus Used to prepare VAQTAS, a Highly Purified Inactivated Vaccine," Biotechnology Progress, vol. 12, No. 3, pp. 406-412 (May-Jun. 1996).
Hames, B. D. et al., "Nucleic Acid Hybridization: A Practical Approach," IRL Press, Washington, D.C., 8 pages (1985).
Hansen, J. et al., "Complete nucleotide sequence of a rainbow trout cDNA encoding a membrane-bound form of immunoglobulin heavy chain," Molecular Immunology, vol. 31, No. 6, pp. 499-501 (Apr. 1994).
Harlow, E. et al., "Antibodies: A Laboratory Manual," Cold Spring Harbor Laboratory, NY, 9 pages (1988).
Havarstein, L. S. et al., "Purification and Partial Characterization of an IgM-Like Serum Immunoglobulin from Atlantic Salmon," Dev. Comp. Immunol, vol. 12, No. 4, pp. 773-785 (1988).
Henikoff, S. et al., "Amino Acid substitution matrices from protein blocks," Proc. Natl. Acad. Sci. USA, vol. 89, pp. 10915-10919 (Nov. 1992).
Higgins, D. G. et al., "Fast and sensitive multiple sequence alignments on a microcomputer," CABIOS Communications, vol. 5, No. 2, pp. 151-153 (1989).
Hirono, I. et al., "Cloning and characterisation of a cDNA encoding Japanese flounder *Paralichthys olivaceus* IgD," Fish & Shellfish Immunology, vol. 15, pp. 63-70 (2003).
Hoogenboom, H. R. et al., "Natural and designer binding sites made by phage display technology," Immunology Today, vol. 21, No. 8, pp. 371-378 (Aug. 2000).

(56) References Cited

OTHER PUBLICATIONS

Hordvik, I. et al., "Molecular Cloning and Phylogenetic Analysis of the Atlantic Salmon Immunoglobulin D Gene," Scandinavian Journal of Immunology, vol. 50, pp. 202-210 (1999).
Inbar, D. et al., "Localization of Antibody-Combining Sites within the Variable Portions of Heavy and Light Chains," Proc. Natl. Acad. Sci. USA, vol. 69, pp. 2659-2662 (Sep. 1972).
Ingram, G. A. et al., "The immunoglobulin of the brown trout, *Salmo trutta* and its concentration in the serum of antigen-stimulated and non-stimulated fish," J. Fish Bioi., vol. 14, No. 3, pp. 249-260 (1979).
Itami, T. et al., "Purification and Characterization of Immunoglobulin in Skin Mucus and Serum of Ayu," Nippon Suisan Gakkaishi, vol. 54, No. 9, pp. 1611-1617 (1988).
Jones, P. T. et al., "Replacing the complementarity-determining regions in a human antibody with those from a mouse," Nature, vol. 321, pp. 522-525 (May 29, 1986).
Jones, R. C., "Avian reovirus infections," Rev. Sci. Tech., vol. 19, pp. 614-625 (2000).
Kaattari, S. et al., "Varied redox forms of teleost IgM: an alternative to isotypic diversity?," Immunol. Rev., vol. 166, pp. 133-142 (Dec. 1998).
Karlin, S. et al., "Applications and statistics for multiple high-scoring segments in molecular sequences," Proc. Natl. Acad. Sci. USA, vol. 90, pp. 5873-5877 (Jun. 1993).
Kashima, N. et al., "Unique structure of murine interleukin-2 as deduced from cloned cDNAs," Nature, vol. 313, pp. 402-404 (Jan. 31, 1985).
Kimmel, Alan R., "Identification and Characterization of Specific Clones: Strategy for Confirming the Validity of Presumptive Clones," Methods Enzymol., vol. 152, pp. 507-511 (1987).
Kongtorp, R. T. et al., "Heart and skeletal muscle inflammation in Atlantic salmon, *Salmo salar* L: a new infectious disease," Journal of Fish Diseases, vol. 27, pp. 351-358 (2004).
Kongtorp, R. T. et al., "Longitudinal study of a natural outbreak of heart and skeletal muscle inflammation in Atlantic salmon, *Salmo salar* L.," Journal of Fish Diseases, vol. 29, pp. 233-244 (2006).
Kongtorp, R. T. et al., "Pathology of heart and skeletal muscle inflammation (HSMI) in farmed Atlantic salmon *Salmo salar*," Diseases of Aquatic Organisms, vol. 59, pp. 217-224 (2004).
Koumansvandiepen, J. C. E. et al., "B Cell and Immunoglobulin Heterogeneity In Carp (*Cyprinus carpio* L); An Immuno{Cyto)Chemical Study," Developmental and Comparative Immunology, vol. 19, pp. 97-108 (1995).
Kretzschmar, T. et al., "Antibody discovery: phage display," Current Opinions in Biotechnology, vol. 13, pp. 598-602 (2000).
Lipman, D. J. et al., "Rapid and sensitive protein similarity searches," Science, vol. 227, No. 4693, pp. 1435-1441, (Mar. 22, 1985).
Luckow, V. A. et al., "Trends in the Development of Baculovirus Expression Vectors," Bio/Technology, vol. 6, pp. 47-55 (1988).
Majhdi, F. et al., "Isolation and Characterization of a Coronavirus from Elk Calves with diarrhea," Journal of Clinical Microbiology, vol. 35, No. 11, pp. 2937-2942 (1995).
Makino, M. et al., "Concentration of live retrovirus with a regenerated cellulose hollow fibre, BMM," Archives of Virology, vol. 139, No. 1-2, pp. 87-96 (1994).
Margulies, M. et al., "Genome sequencing in microfabricated high-density picolitre reactors," Nature, vol. 437, pp. 376-380 (2005).
Mattheakis, L. C. et al., "An in vitro polysome display system for identifying ligands from very large peptide libraries," Proc. Natl. Acad. Sci. USA, vol. 91, pp. 9022-9026 (Sep. 1994).
Mertens, P. et al., "Family Reoviridae," Virus Taxonomy: Classification and Nomenclature of Viruses, Eighth Report, pp. 447-454, 10 pages (2005).
Mierendorf, R. C. et al., "Gene Isolation by Screening Agt11 Libraries with Antibodies," Methods in Enzymology, vol. 152, pp. 458-469, 20 pages (1987).
Morrison, S. L. et al., "Chimeric human antibody molecules: Mouse antigen-binding domains with human constant region domains," Proc. Natl. Acad. Sci. USA, vol. 81, pp. 6851-6855 (Nov. 1984).
Needleman, S. B. et al., "A General Method Applicable to the Search for Similarities in the Amino Acid Sequence of Two Proteins," J. Mol. Biol., vol. 48, No. 3, pp. 443-453 (Mar. 1970).
Notredame, C. et al., "T-Coffee: A novel method for fast and accurate multiple sequence alignment," J. Mol. Biol., vol. 302, pp. 205-217 (2000).
Nusbaum, K.E. et al., "Protective immunity induced by DNA vaccination of channel catfish with early and late transcripts of the channel catfish herpes virus (IHV-1)," Vet. Immunol. Immunopathol., vol. 84, No. 3-4, pp. 151-168 (2002).
O'Neil, P. F. et al., "Virus Harvesting and Affinity Based Liquid Chromatography: A Method for Virus Concentration and Purification", Biotechnology, vol. 11, No. 2, pp. 173-178 (Feb. 1993).
Olsvik, P. A. et al., "Evaluation of potential reference genes in real-time RT-PCR studies of Atlantic salmon," BMC Mol. Biol., vol. 6, No. 21, 9 pages (Nov. 17, 2005).
Pack, P. et al., "Improved Bivalent Miniantibodies, with Identical Avidity as Whole Antibodies, Produced by High Cell Density Fermentation of *Escherichia coli*," Bio/Technology, vol. 11, pp. 1271-1277 (Nov. 1993).
Palacios, G. et al., "A new arenavirus in a cluster of fatal transplant-associated diseases," N. Engl. J. Med., vol. 358, pp. 991-998 (2008).
Palacios, G. et al., Panmicrobial oligonucleotide array for diagnosis of infectious diseases, Emerg. Infect. Dis., vol. 13, pp. 73-81 (2007).
Paul, William E., "Fundamental Immunology," Third Edition, Raven Press, NY, 5 pages (1993).
Pay, T. W. et al., "Production of rabies vaccine by an industrial scale BHK 21 suspension cell culture process," Developments in Biological Standardization, vol. 60, pp. 171-174 (1985).
Pearson, W. R. et al., "Comparison of DNA sequences with protein sequences," Genomics, vol. 46, pp. 24-36 (1997).
Pearson, W. R. et al., "Improved tools for biological sequence comparison," Proc. Natl. Acad. Sci. USA, vol. 85, pp. 2444-2448 (Apr. 1988).
Pearson, William R., "Effective Protein Sequence Comparison," Methods Enzymol., vol. 266, pp. 227-258 (1996).
Pfaffl, M. et al., "A new mathematical model for relative quantification in real-time RT-PCR," Nucleic Acids Res., vol. 29, No. 9, pp. 2002-2007 (2001).
Prior, C. et al., "Process Development for Manufacture of Inactivated HIV-1," Pharmaceutical Technology, pp. 30-52 (Apr. 1995).
Raa, Jan, "The Use of Immunostimulatory Substances in Fish and Shellfish," Farming Reviews in Fisheries Science, vol. 4, No. 3, pp. 229-288 (1996).
Sambrook, J. et al., "Molecular Cloning: A Laboratory Manual," Third Edition, Cold Spring Harbor Laboratory, Cold Spring Harbor, N.Y. 21 pages (2001).
Sandhu, Jasbir Singh, "Protein Engineering of Antibodies," Critical Reviews in Biotechnology, vol. 12, No. 5-6, pp. 437-462 (1992).
Sato, H. et al., "Expression of YAV proteins and vaccination against viral ascites among cultured juvenile yellowtail," Biosci. Biotechnol. Biochem., vol. 64, No. 7, pp. 1494-1497 (Jul. 2000).
Sayan, R. et al., "Discovery of a new class of immunoglobulin heavy chain from fugu," European Journal of Immunology, vol. 35, No. 11, pp. 3320-3331 (Nov. 2005).
Schlesinger, S. et al., "Alpavirus vectors for gene expression and vaccines," Current Opinions in Biotechnology, vol. 10, pp. 434-439 (1999).
Shmulevitz, M. et al., "A new class of fusion-associated small transmembrane (FAST) proteins encoded by the non-enveloped fusogenic reoviruses," EMBO J., vol. 19, pp. 902-912 (2000).
Singer, J. T. et al., "Expression of capsid proteins from infectious pancreatic necrosis virus (IPNV) in the marine bacterium *Vibrio anguillarum*," New Developments in Marine Biotechnology, Plenum Press, New York, pp. 303-306 (1998).
Smith, G. P., "Filamentous Fusion Phage: Novel Expression Vectors That Display Cloned Antigens on the Virion Surface," Science, vol. 228, pp. 1315-1317 (1985).
Smith, T. F. et al., "Comparison of Biosequences," Advances in Applied Mathematics, vol. 2, pp. 482-489 (1981).

(56) References Cited

OTHER PUBLICATIONS

Solem, S. T. et al., "Antibody repertoire development in teleosts—a review with emphasis on salmonids and Gadus morhua L.," Developmental and Comperative Immunology, vol. 30, No. 1-2, pp. 57-76 (2006).
Subramanian, K. et al., "Detection of aquareovirus RNA in fish tissues by nucleic acid hybridization with a cloned eDNA probe," Journal of Clinical Microbiology, vol. 31, No. 6, pp. 1612-1614 (1993).
Tamura, K. et al., "Molecular Evolutionary Genetics Analysis (MEGA) software version 4.0," Mol. Biol. Evol., vol. 24, pp. 1596-1599 (2007).
Thompson, J. D. et al., "CLUSTAL W: improving the sensitivity of progressive multiple sequence alignment through sequence weighting, position-specific gap penalties and weight matrix choice," Nucleic Acids Research, vol. 22, No. 22, pp. 4673-4680 (1994).
Thompson, J. D. et al., "Multiple sequence alignment using ClustalW and ClustalX," Curr. Protoc. Bioinformatics, Chapter 2, Unit 23, pp. 2.3.1-2.3.22 (2003).
Trepanier, P. et al., "Concentration of human respiratory syncytial virus using ammonium sulfate, polyethylene glycol or hollow fiber ultrafiltration," Journal of Virological Methods, vol. 3, No. 4, pp. 201-211 (1981).
Trifonov, V. et al., "Frequency analysis techniques for identification of viral genetic data," MBio., vol. 1, No. 3, 8 pages (Aug. 24, 2010).
Tsurumi, T. et al., "Structure and filtration performances of improved cuprammonium regenerated cellulose hollow fibre (improved BMM hollow fibre) for virus removal," Polymer Journal, vol. 22, No. 12, pp. 1085-1100 (1990).
Tucker, C. et al., "Assessment of DNA vaccine potential for juvenile Japanese flounder *Paralichthys olivaceus*, through the introduction of reporter genes by particle bombardment and histopathology," Vaccine, vol. 19, No. 7-8, pp. 801-809 (Nov. 22, 2000).
Veseley, T. et al., "Production of monoclonal antibodies against immunoglobulin heavy chain in common carp (*Cyprinus carpio* L)," Veterinarni Medicina, vol. 51, No. 5, pp. 296-302 (2006).
Wahl, G. M. et al., "Molecular Hybridization of Immobilized Nucleic Acids: Theoretical Concepts and Practical Considerations," Methods Enzymol., vol. 152, pp. 399-407 (1987).
Warr, Gregory W., "The Immunoglobulin Genes of Fish," Developmental and Comparative Immunology, vol. 19, No. 1, pp. 1-12 (1995).
Whitlow, M. et al., "Single-Chain Fv Proteins and Their Fusion Proteins," Methods: A Companion to Methods in Enzymology, vol. 2, pp. 97-105 (1991).

* cited by examiner

A

B

C

A

B

SEQUENCE LISTING

```
<160> NUMBER OF SEQ ID NOS: 44

<210> SEQ ID NO 1
<211> LENGTH: 1143
<212> TYPE: DNA
<213> ORGANISM: Piscine reovirus

<400> SEQUENCE: 1

gataattttg attgcataca ttcctatcat gtcgaacttt gatcttggac gtcaggctaa      60

taagccaaaa actgaatatc acttgaatgc attaccttac ttgaaatgtg gaattaaaaa     120

cagcgaatct gttggttctg taatcatcaa ctttcctgct cgtttcgaca ccgcaaagag     180

cgtcagcccc ttatctgcaa tgactaatga tggcttcctc aagttcaagg acccttctga     240

ctcccttgcc tctcgtgacc gtcctgcgtt caatgactat gtgcgtgcac ttcaaccatc     300

gcctgagcat cctcaccatt tccaagcact tgaccctgcc ttcactgatg aaatcctgaa     360

aacttgtgat cctactttca actggacatc catcaaaagt ggtgacaaat actaccttcc     420

tgctatcagt caagctctag tgtatcgtgc ctctggcttt cgtttcaact ctgagaagca     480

cctggaacaa actggttcat tattgcccat agctcttggt atcagcaaag caacatgcgc     540

cctccctgtc cttgtggact ctggtacagt ggtctgtcct gaagagaatg tttctgcctt     600

gttttcaaaa gacaaactct cctccctgga catccagttt ggatacccaa aaccaaagaa     660

tggcaatgat tccactgcgt acacaaaatc catcaatggg taccagattg gtgcgtatgg     720

tttgaagctt cctggaggtc atttcctcaa gctgattcac atcctcaact gcatgtgcct     780

gaaagcagac ctggatcttc tgtctcaagt gccctccctg gcagattccc tcaatcgtgg     840

aatgagatgt ggctatgccc tgcttcaata tgtttcccag ttcgccactg tggacagaga     900

attgctcctg atgtctttcc tcctgaaaga ggctaacgac cccaccttcc atgaagttgc     960

tgcaatgtgg aaatccgttc gtgatggtac cgctcaaatg gacgacgtgc gttttgacct    1020

gcaacctttt ggcatcatgg cttcaactgc atcgctcagg gatggggttc gcatcatggc    1080
```

-continued catgttttgt tagaaaccgg atctccagcc ggggacttgc atacaatcga acatctcttc 1140
atc 1143

<210> SEQ ID NO 2
<211> LENGTH: 1081
<212> TYPE: DNA
<213> ORGANISM: Piscine reovirus

<400> SEQUENCE: 2
gataaagact tctgtacgtg aaacccaaat ggcgaaccat aggacggcga caactactga 60
cttttctgat tttatagaat caactttaca cgggaatatt atcttctatg acgaccaaca 120
taacacttca agcgagtgga tccctggtac cagcaagttt gttagggtcg gttcccttcg 180
aatatgtgtt gaatgcgggc atcgggttgg tttgtctcat aatgctaagc ctgttatggt 240
cactcatcaa tgcgacggcg atacgttgtg ggatcattct acacccggag attggacatg 300
gagtgaatgg agctatttcg tcactagttg cgcaaatgcc ctttctgcga acgcagacgc 360
ttacctcaga atcctcaatg acaaatggac agaagacaac agtcgcggtt caaacgacag 420
accagacaga cgcggagtca ttgaagctaa gcgacgcctt agagacgata tgcgtggcat 480
aatgaagaag aaaaccgctg gagaccttgg cttgactggc tggctgatcc ttgatcctga 540
cgagttggaa tctttccctg actattcaac ggagatgaca cagctgcagg aagacatgga 600
ggagctgaac ccagtggagc agaagactgg aaatggtgga aaagcgcacg tggcggccgc 660
aaatcagttc ccacacaagg tcattctgcg tcctgcgtat ggcaccgttc ccatcgtgat 720
gtacctggac acgcgtgaag atcacaacgc ctacctttgc ctctcattga aaacgaaagc 780
gcacatggta aacatgatac gaaggatgtg ctattcgggc atgccagcca acatcatcaa 840
aatgacgcaa ggaatggcac tctctggaat ggaggagatg acttttcgtt caggtcacag 900
actttttggt cacatgcact ctggtcatac aatccctgtt aaaggaactt catcattgac 960
attgacatct ggtaaatgct cacacacgtg tcagaatttg ctcaaatggt catcggcgtg 1020
atggggagcc tactgtagac ataaaatcca ttgtctgagg gggaaggagg tcttattcat 1080
c 1081

<210> SEQ ID NO 3
<211> LENGTH: 1040
<212> TYPE: DNA
<213> ORGANISM: Piscine reovirus

<400> SEQUENCE: 3
gataaagatc ttaaccgcag cgacatctca gcttaaccat gcatagattt acccaagaag 60
accatgttat tattaactca agacttgatg ccattgaaga ggacaacaag cggaacttcg 120
cttcattgaa acaatcaatc cacaacaact acggattgct tcgcagcctg cttggaggtc 180
aaggacgctt gaacgggaaa attggagatc tggagaagga cgtcaatctg atacatttga 240
gagtggtttc cctggaacat gcgcttgatg atcttcgcgc tgattttgac gcttttactc 300
caactgttgg tcctgagatt gacgacaaac tggctccgct ccagaaacag cttaaggtgc 360
tgaatgacca gctcacaatc atgaactctg aggtcgctgt gttggggaaa gggatattcg 420
gagactatca actgactgac ctgcttggac acactgttgg tggagttgcg gctgtgacga 480
caaattcact cacaagcgcc ttccgcttga gcgaccgact gcctgcgact actgttggag 540
atttcagtct atccactgga gtaggataca cctttgttgg gacggcacca aggccaatcc 600

-continued

```
ttcaagttga agatttcatg cggggcacct gcaggatgaa tctcactgac actgcgctga    660

tgtatggtgg tagccacatt ccactcctgc aacagtcact gcttcaactg gagacaacag    720

ttcctcctgg cccgacagat tggaagaagc tgcctcaaat ggtgaaaggc gtgctctgga    780

tgagtctggt ggattatgaa ggcgccaatg tagttcctgt ggtggtgatg aggaaggtta    840

atgctacggt gacgactgtc attctcccag acatggttgg caagcaaaag ctgatttcct    900

cgtttccctg gacgacaaga tcaacgttca tgagtcctgg aatggaggtg atcattcatg    960

gtggagactt cgtgatcatc atctagcgtg gaagagccac gtgtcgcact ggagatattg   1020

cggtaagcct gtttttcatc                                               1040
```

<210> SEQ ID NO 4
<211> LENGTH: 1329
<212> TYPE: DNA
<213> ORGANISM: Piscine reovirus

<400> SEQUENCE: 4

```
gataaatttg ttggtgacga tatggctaga gcaattttct cgggtatttc tgcctttttc     60

gcgaacgcac cttacgttca agatggcgac acaattaagc atgcattcct ttctggcgac    120

tcactctttt tccaagggac caacacactg taccccacac tttccacaag ttatcaagga    180

gatactgacc tcccaacccc atttactgtt atgtatcaga ctgctatggt ccggtctgcg    240

ttatttcagg taccactctt cggcggactt tggaacgcaa gaagctatcg ggatttagtg    300

ttcacttctc aggctatgct gaatgtcaag actaacacct ctgtcacctg ccctcctcct    360

gtcataccgc gacctgcgta tgtctacaac gtgatgaata atcaaagatt cgcgcagagt    420

gctacagcta ggaacaaagt ctatgtcgat ttttcaatca ccacattgtt tcagatggac    480

atcaatggct tcgctcttcc tctcttgttc aatcctgatg acaatggtat agatgtgacc    540

cttgcattga ctagccttgt gggacaatct tggagtacta tcgtcggtgc acgatatgaa    600

agcgctggaa atgcggcaat ggatatagac aacccaatac atcgcacgaa cagagcactc    660

atgctcctat acctgggtag cgcatgcgga tacttcaatc caacgatgac atggaatggc    720

ttctattttc gtcaagctgg gaaaccaggc tcctggggcg ctgatttgga cccaatttta    780

gttcgcggtg actctgctct catcaatcga gccacattcg ttcgtttgaa tcgttgggtt    840

gtcttcaaag acttcctctg gcagatgtct cgtggaacat tgcatgctct ggtcctcgga    900

ggaatgatct gcgctgttga gcaacctttg agaggtctga gcgttatttc agttttggca    960

aatactgttt gcgcaccttg gactggtgtt aatggacgcg cgggggatga ggtaactacc   1020

attggcttga agtacgttgc gatcgagaat ctgattcggt ctggtagtta caccgttgct   1080

gaaggtgtgg tcgccgatgc ccaaattgcc gcttgggggg tccgcaacac agaccatatg   1140

gatagagttc gtgctgctga tgacgctaac gtattagccg gagtcaacat cagacgcgtc   1200

aagccctggg ataatggtgg tggattccaa agattggctg ctgtgagagc gttagtgaat   1260

ctaatggcgg caaatacacg gtaactctag ccgggactga ccaccctgta gtcagcacgc   1320

ctcttcatc                                                           1329
```

<210> SEQ ID NO 5
<211> LENGTH: 2179
<212> TYPE: DNA
<213> ORGANISM: Piscine reovirus

<400> SEQUENCE: 5

```
gataaatttg tttaacaggc ttgaccatgg gtaactatca gacaagtaac aaccaatttt     60
```

```
gggtaactgg cgacggcaat gatttcagtg ctgaaggcgg actcgactct acgaacgcgg    120
catcactcga ctttaaagct ggaaaaacga atcctggtgg tcacatgtat gtgatatccg    180
gtgacaatac gtcagatgtc gtgaaatggg acagtttaac gcccttgtat gggatagatg    240
gacagatggt tgttgtgctg actgcggtag ctatgtctac ttttgagaag atggtgaatt    300
taattgagat gtatagacca ttacttgaag catcacagca gatggcttgt taccgtgatt    360
ggaagaagga tattgtcctg cttgatggct atgttggtag tactcctcaa tctgctgtca    420
ctaactttgt gactggggct agtgtaatca atctgagaga actgagaagc ctggggaaga    480
tgtatcaaaa catactcggt gtcatagcta actatgatcg tgacattcaa gttgccctgt    540
ccctgatccc tcattcaact ccaatcggta gtctgaccgc tgacatgcat tccattctga    600
ggatgttctc cctctccctc aagccaacca atgtgtgcta cctctaccct gaagcggctc    660
tgcaagtgat tcgagctatt tcaccgactg tcaggaatgt tgacactcaa caaggtggat    720
caatagttga gactctcaat ctctttgaac ctgttttcaa tggcactgga cccaatcaac    780
ctccactgac tgatcagagc gaagtccgtt caatcgcaag gtctgatgca tccctggctc    840
aactctctct catctccagc acagaaccca ttgaagcaag agccctcaaa agtggcacac    900
caacgaaaac gtacgacatt cgtctcgttg atcccctcac cacaccctgg gtatccaaag    960
cgtacgcatt ggctgaaaag accgcacgaa tccaattcac tgacagtggt cgcaaaacct   1020
ggtatactgc agttggcaaa ggaactctgg cattgcatct ggatgacatc actagcatgt   1080
ctattacaat ggatctaggt ggtgagagct actactacaa gacgttagcg aacgacgcag   1140
ctgaaactgt tgatcctgaa tctgccaccg ttgctttcat cttgttctca gtcacgaggc   1200
ccctggagga gataaccact gcgtcagagc tgcagactgg gaagatcgtt gcttttgaga   1260
aactcatggt cgcaaactcc agtgtgcagg gcgctaaaat cattgcaaac acttccctga   1320
agtacaactt tgatcacaat tctatcagcg gcgacaaatc tgaattgaac cactacctgc   1380
tgtgtcaact gctcttcaac aatctctctg catccaccac ctacactcaa caagacgcat   1440
gggctgggaa gacgacaatg caatctctgg attcagataa ggtgacagtc aaaggggttg   1500
aggttgacag agtcattcct gctggagcgt tcggtaacta cacaactgct gagcagaagt   1560
cctcacttcc aaatgatctg cacagcgtca tggcaactca tcttgagaga gctgcaaaag   1620
caatgacagc aattgatgat gaagatcaag agggtggatc gacagttgcc aatgcaatct   1680
ttggagcact gatttcaaag gaatcacctg ttgctggacc gatcccctgg aagaacatca   1740
agtttgacga gttgagagtt ttgtctgaca aggccgcttc aagtttcaag agagacccat   1800
cgcaagctct gatttcacat gacccggtcc ttggagacag tgcagtgatg acatcgctac   1860
ttggtggtat tggaaacgca gtcaagacga agggactatc tgccgcgtgc aaggatacga   1920
agagtgcgtt gactgctgcc cagtcaggta gatctgtgag acagacgatt ctggacaaga   1980
tagagaaact gtttccacca ggcccacgcc ctgcgaagaa aatgattgag gaaggaccat   2040
ccaaaaagga agctaggcgt ctgggagact cacgtcgagg ccaaaaatag gttcccgcac   2100
caccctggca gtacgttgta cgtgacaacg gtgctctgcg gcctgtttag cgggtgacac   2160
cgaacgacaa atcttcatc                                                 2179
```

<210> SEQ ID NO 6
<211> LENGTH: 2383
<212> TYPE: DNA
<213> ORGANISM: Piscine reovirus -continued

<400> SEQUENCE: 6

```
gataataact cctttgccac catgcctatc ataaacctgc caattgaacc tactgaccag     60
agtattaccg aatttaagac gcaagcgcag accgtgtttt caggatgcat ggagaatact    120
gatgtcacat ttgttgacta cctcaagagg gacgttaaaa tattcatcgt tgacaaccgt    180
tttctgctgc cgcagatcgc gaagatgatt gattcgtcgg atcttgatga gattgccagc    240
caagtgctaa acttaccatt acttagcgaa gcgtgcttca ttctacttcc tcccctttct    300
gtgatggcta agaggcttct ttcctccagt gattcctacc ctgacatctt cctcactagg    360
gttccaactc gcgtgctcaa agctcaatct gacaactcaa gatccactgc tctgctgaaa    420
ttcatgccca aggttgttac gtcatccacg actgcctctg acatgctgac gatgtctgta    480
cagaatgctg acgtttacac gttgaccccc gatgtcatcg gaatgccact tcgtcgctat    540
gcagagaaat ctcattatcc ctcagctttt gattttggaa gtgcacatcc atcaaactgg    600
cgtcgctcag tcatcaaggc ttcaaactct cttctgatac caatggtgcc ggtcatgtcc    660
actgcgaaga ccttatatct ggacgccgat ttctcaactt ctgacgatag aactggcatc    720
ttttggcgtc tttctgcctc tgcgcgtatt cgagctcgac aacgtggtgt gattgtactc    780
ccctcaatga tcaaaacatt ctacgagaaa gaacgtggtc tgaagagcgc accagttcaa    840
cttcgcagag aacacaaaat ggctgccaga ctcctgagga ttccttttgg acgagtgccc    900
tccgaaactt cctttcgccg agacatggtt caatgttgtg atctgctcgt ttccacctct    960
gtcctgaaca agcttttgag tccaaccgag gctggtaaat cacctccctt tgacaaatac   1020
gtgtttcatg gtgtgccagt tgagttcatt aacagagtct gccctgacat cggtacacaa   1080
gctctcggcc gagacaccaa tggatatctg caagaatggt tgattatgtt attcctgatg   1140
tctgactata tcacctccac caccagccgc cggcgcctga ctcttgtcac caactttgac   1200
ccaatgcgaa agtggtacga catcaccttg ctgaaaatca ccaataccta ctatcaatgt   1260
caagagatga tgacgcctcc ggccatctct tcttttggtg tgtgcagtca gaaaggcact   1320
ttcaagtcca ctctcagcag ctggttgtct caagtcatcg tgcgcggcgt caatctcttt   1380
cctgaaggat cgattgtgga ctctgacgat cttggcagca aactggatcc aacattcgag   1440
agtgagtggg agactaacgt catcgagaaa attggtatgc ctgtcatcat tcgtgggctc   1500
acggaagaag gtgctttcaa gataaccact gacaccatgt ttgacacgta tgcactgttc   1560
agacaactat acgatcggat gattgttcca gttgctcggc atttctttga ctactcagtc   1620
gcatctggta ggaagatgat ctttgcgcat tgcgacagtg agttccttga caactctttc   1680
ccttctccgt tctatcgcac tcacatcacg atcgacaact acggcaacat cctgaaccgt   1740
ccaaaccgag ttggtggcgt tctaagccag tacgtacttg ctgagtgcta ccgtctcatg   1800
gccacgtcct gcaaatccag accgattgcc aagctgttga aggctaagtt ggtgccctgg   1860
tgggagtttg acagtcatgt gaagcggatg ggaggcacac ctgttcacta ctcacttgga   1920
gtcaagattc aacctgagtt gatgagagac gctggatatt gtggtcatct gatcgatcat   1980
gcgcgcgtcg aagtacttca agcgatgtgg gttcccgaag cagtggatga gagtttcttc   2040
cataaccctc caagcatgcc attgaccatc catctggcgg attccaagta caacaggtat   2100
gagcccatcg gtgaacacaa tttgaacatc cctgttctga tcgacacctc cacctcttac   2160
ctttctgaga catatcttcc agctggagtc gtgttcacac caacaaaaag attcacagtg   2220
gaggggtgtg actttaactg ctggaggggg aatccaatca ctttcaaggg tactctgagt   2280
tggtggtcta cagctggtga gtgagtgcca tggggctcct gactacttca gatggtccgc   2340
```

```
cggtcagcgg ctgaaggaat aaggggctta agagattttc atc                  2383


<210> SEQ ID NO 7
<211> LENGTH: 2403
<212> TYPE: DNA
<213> ORGANISM: Piscine reovirus

<400> SEQUENCE: 7

gataaagctt acgacacgtg acatccttac atgaactgtg aagactgact tactataact     60

tactgaaact aactactact acaatggctg aatcaattac ttttggagga ccatctcgca    120

agctggactt ggttgcatct gggagcaagc cgatcacagt cactgtgaca gttggagatc    180

tgggctgcag tatctacgga accgttcctc gtggtactga tgaattcgtt acctctgatc    240

gctatcttgc gatgtgccgt cacctgttgg tttttaagcc tacactgaac aatgggacac    300

tgactcatta cactgcgttc tctgctatac gtagtatgat ttctcctctt ggatttggag    360

tgatgcgcaa tgttgatgtt gttgagaagc agtgtgccat cattgaagct cttgaaagac    420

gtgggatgtt gaatgaagtc aaggatgcgg ctgctgaatt acctcttcaa ttggatgtca    480

ctgacacctc cacacatgtt gaccctgcga tcattgactc actcccccca ctgattcaaa    540

atgaagttgc tgctggcctc acacctcttg agttgcctgc catcaccatg gttcaaaccg    600

ctcccctgat cacccctgct cttggaatgg agaatgatga tttcaatctc tctcgctact    660

tctttgcctc tggtttcatt gatcaagcct ccagaattgg cggtactgtg aatgatgaat    720

acgtcaaagg attcatgcag gcccttcccc gtttcaacga tgatggctcc attcgtgtag    780

attgtgatgt tctgacttgc ttgtgctccc gggatgaaga tttgtctgtt ttgacacctc    840

tgtctgtcaa caccactgct gtttctgaca tgtttgagct gtcccatgat caccagccaa    900

tggcctacct gcgcactgtg tatgtggaag actacattgc ctcacatctt gagtccctga    960

aaaacagaga gaccgccact cctctcgtcc tgaagctgag cgctgtcaac agtgtcactc   1020

cgaaagccct gatcgctctg gttgaatcca aagctactga ctcaatcttc aatcaggctg   1080

acaaacgctg gatgattggt cttgatccca tgttctctga gtgctggcct ggggcaatcg   1140

ctttgctttc aatgcttttt gatcacaagg ttgactactg gtctgttaga tgtcgtttca   1200

tccttcgcag cgctctgatt ggcatgagtg atgatgacgc acgccctagg gttcagatga   1260

tgcggatgca ctattccctg accacaccaa ctacctggta ttcaacgcgt ggcgtctact   1320

ctgctgaagg tcgttccaaa attcactatg ccagcggaga ccgaatgaga ttgggactgc   1380

gtgttggtga ggtgcgagat cgtcaagtca cgatgttgga ggacctttcc accattcact   1440

ccatggatgt cgccaacatg aaggaccagg tcattcagaa agacgtgcag ctgaaggcgc   1500

tgaccgaggc catgtcccag aaggattctc tcattgacag tctgcgagcg gatgttgctg   1560

gattaactga gcgtgcagtc ttagttcaag ctgagcatct cactacgatt gctgacatgg   1620

aagtgaggag agtccagtct gaggataagg ccaggattgg cattgacgca gcgaatcgcc   1680

gagccggaga agccattgag agtgcccatc tcttgactga ggagttctcc aaatgtctca   1740

gctctgactt cctgatggtg aaaccacttc ctgaacacaa ccaatgtcct gtgccgctgc   1800

tggagtctgt ttggcctgca ttgtgtcaac gttacattca aaacatgcaa ctggttgatg   1860

aaatctggac caacaagctt gctgatgcga ctgacaccat cgccactgaa atggctgagg   1920

agacaatgag gatcattgcc gaaagagact gccaagctat ggtcatgcca gtggttgaag   1980

caccaaaacc tcaaagaaaa cctcgcatct acgagccttc tgacgacgac cttgaacgca   2040
```

```
cgagcgtgtc gagcaccagc agcgagaaga agaagcgagt catctggagt cgttctgcca   2100

ctagagttcc ccgcactgat gtagactttt ctgcaatcac tgccgcaaga cgtgatgaac   2160

atttcgaact ggggatgcct agagaaggaa gatatcctgt ccacagtggg attcctggca   2220

gtgtgcgcgc aaccatgact cggggcctgg caatcgacag catgagtgag tttccaaaaa   2280

tcatcgactt tggtggctca gatgactggg acgtgggcgt gaataatgtg ctacgtggct   2340

gaatggtgta agtctgattc tatgttttcc ctaggtttgt acgtgtgagc tcccctcctc   2400

atc                                                                 2403
```

<210> SEQ ID NO 8
<211> LENGTH: 3911
<212> TYPE: DNA
<213> ORGANISM: Piscine reovirus

<400> SEQUENCE: 8

```
gataatgttt gttttgccat ggagcgactt aagaggaaag ataagtacaa aaatactaat     60

actaaagaaa atacacaaga actgactgtt gacgaatctg ctgtatcttc caataatcct    120

accggaaaaa ctacagacaa tggcggcgtc ggtaaaaatc ggggatcgtt accagctatt    180

tcggcatcgg atagtgacag tagtgaagaa gaagcaattg ttgaggtaca gagaatcaag    240

aagtcaaaag ctcagaagaa gagcactaaa ttggctacaa caactcaaaa tgactctaac    300

gagagtaata ttgtaactca acctggcatg ggaatgtctg caaatgtgag taccatcaat    360

gtgttgccac ctacagtgac tatgcctttg cagactactc aatcatctcc tggccctgca    420

gttgatcaat ctggtgagac gaagttggga agatcgtcta acgttagtgg aaaagaggct    480

gctatgcaag ctccggctgt cgaccgctct gagattactg ataaccctag gtacgatcct    540

accacgtcta caggcactac atcctgccca ctttgcttca tgaccttaag ttctgttcct    600

gatctgctac ttcacatttc tatgcgtcat gcacccattg acagcttttc cacgactgca    660

ccacagattc aggatgctga gagacagttc attacaattt ggagtgcaca taacgctgca    720

gctttgtcct cactttccac tggtctgacg actagttcaa gtttcttgtc taaggtgcct    780

ccgcgtttat tcgtattcga tgatggaata tgctcatctt ttaggtttat gacggctgtt    840

gaagctcgct atctgcctga agtacgtggc tacgcctggt atgatgagat ctatgacatc    900

attctgcctt ttccagcttc agctgtggtt cgtatcgtac ttgacacgga ttgggctatg    960

gttagtgatg aaacgttacc tattaaacta accacgcttt tacctactct ttcaaatgta   1020

ggcttgttgc gtcaagttct cactgttctt tctgacaaca gtaaatacaa tcctgtttgg   1080

gctcgcgcca acgtaatcgt gatgggtgtg aaatttatac ttgccaatct tgtcatcaac   1140

agatctagtt cttgggctca agactctact ccctcggttt ctggcagact actacgcaca   1200

gtccctggta aaccagaata ttggccattg atgtatccac gaaggacgct taacgctaat   1260

gtcagcaaga tttcacgttt cgttgagcaa acacaggctg aacgcactgg cagagttgat   1320

cgagcaatgc tttatcaagg agagaaagtc atctatactg acgttgctga gacctgcgat   1380

acgttgaccg tgcgtttgcg tgacatgtgg actgggaaga ttttcaaaat gcattacaca   1440

cattctgaca tcgctctggc tctatctgag tgcgctcgtg tggtctcctt ctcagctgtg   1500

atggcgttat ccccacgcac aatacttcct tgtcgtgcga cgactgatga aagaaagctg   1560

gcacaagttt tgaacatcgc tcgcctcggt gatctcagac tacgaattga gcctattatc   1620

caatccgctg ctgacacttt aagatcagtt accatgctgg agatcaaccc caagattttg   1680

actgctgtct tgaacagaat atgtgaaaat caaactcaat cagtgactgt gactgggaca   1740
```

```
attcttcgtc tgctgagctc tgctaccaca gattcttctg ccttctggac ctgcatcgca   1800
agttggttgt acaatgggat agttaccacc actcttcgtc aacaagatta ccctaacccc   1860
actgcctcca tcacggatta cactgcactc tggtctgccc tgattgttag tcttgtttct   1920
ccactcacca atgacccaaa tgctcctgtc aagatcttca tgactatggc gaatcttttc   1980
aacggatatg aacgaattcc gatgaacaat gccagtatga cacaaggaac acctccctgg   2040
gcattcaaca atcctaacaa atggccggcc tgcttcatcc aacctcgcaa cattaaccag   2100
aacattgcgc cattcatgag agcctgggct gacttgatcc accgctactg gccacaacct   2160
ggtgtcgtca actatggatc acctcaccac cttggtgcta ctgaactgct agttgaggat   2220
ggacagatcg tcaccccgtt accagttcaa cctcaacagt ttgagtacgc tgcacttgat   2280
cgtgacaatg agatgtctac ctggatcaac caagtttgca atttcttcat ccgctgcatc   2340
aacggaacgg atcttcgtac cgcttctaac caagctactc agcaagcttt gatttctgcc   2400
atctcacaat tgaagacctc cccatccctc acatatggat atatgtccag gtatttacca   2460
tatgagttgg cgatgatttc acccacgctg gcgttacctc cattccaaat accattccag   2520
cgtttgaatg tgaacgacat cgtttaccaa attggagtcc gtcgtcatgt ggtgagggat   2580
caggttgaac ctgcacttga cacaagttcc acattagaga ccattggcca actgattgag   2640
atcgatgctc aggccctgct cgtttcgctc ctttctggta ccatgaatgc taaggtcctg   2700
ccatccgtcc actacgcaga gaaaatcact cctctttaca tggatgacga ctttttcgcc   2760
cctcatcaaa gagccgtcgt cgtcagtgaa gcatactccc tagtacgcac catcatctca   2820
cagatttcag acacgcgtgg accgcaactc aatcctctgg cttggatccc agctccaaac   2880
gcatcatctc ctgtctcagc cgaagtagcc agactcgtca atgacatgat caaggaagct   2940
tttgacatgc ctggtgaact gcttgaagga ttgatcggat atggtgaccc tagatacact   3000
caagtcgaga ttgttgcaca gaggtgtcgc gcggctccac ttcggttcga accactgatt   3060
cctccgtctg ttctggctca agagcttcaa cttgttgaga acgtgatcac tgctgaacct   3120
aatctgtttg gattggctac tggagactta tatctcgagc gcattgacac ttcagccggg   3180
ttctctggtc tcaacgttat cggctgggag caatgggatg ctaacactcc aggagtcatt   3240
gtcgccggta gctctctact catctgcagc ggattcaacg gagtagaccc aatgatcatg   3300
gatgctgatg ggtggaacg gccgattacc ggtagatggg ttgtcacact ggaagcttgg   3360
cgtagcagcg tggtcaccgt ccagaagttg ctgttaccaa ggatcagagc aggaaagttg   3420
gctgtaagga tactggttgg tatttttcca tacaccatta actactatga acccgctgtt   3480
ggtattgacg agtggaagct gttgtccgac tgggcgtcca tgtgtgaacc tacaggaata   3540
ccggccatac ctttcactgc tccagttcca tctgatgtgt ccgttgtcac cgctgcgtgc   3600
gtgaggtatc tgaggtgctc caccttcaac gaaggctcat tgatggctac taacgcagga   3660
tcacctcgca ccgtgtttgg gcaatcagta gagtttgaca tcggcagatg gatgcagcta   3720
tgtgatttga acactggagt cgacgagata cagctaccca acatgattga attctatcaa   3780
atcttcagac gctacaacat cactcaaacg gaactgactc aagttgtgac attgactggg   3840
actttgactc atcctgtact caactaagtg gctcggcgga acaggaggtt cacaaacatg   3900
acaacttcat c                                                        3911
```

<210> SEQ ID NO 9
<211> LENGTH: 3916
<212> TYPE: DNA

<213> ORGANISM: Piscine reovirus

<400> SEQUENCE: 9
gataataatg gagaaaccta aagcgcttgt caaccaacta cctgaagact tggaaaacct 60
gagtgtggca ctaagtggca ctatcgaatt aactgctgat atctggacta acgcgagtaa 120
aacttttagg actacgcaaa gacatgaagt atatgacata attaataaaa ttgaatttat 180
tgattctttc ttggttccgt catctctatt tcaaccacct ccacacaaaa gatattggga 240
tgtcgacgtt cgccaacgag ttgtgcgtgt gcctaagtgt gcagttcctg atgatgtcta 300
cctccctcac gctaatctca ctgacgtgct ggaaatcaat acagaatcta ttcacaagta 360
tggtcaactg cggaaagaga ttcaagctgc ggctaaaaga ttggatccaa ctgcaaggat 420
cgcagagacc ttttacaatc tttcagttta tcaagcaaac caaatcaaat ttcccctcga 480
gagatttctc ttgtgtttag tagttagtta cgcccatgag ctgtctccct cacctctcct 540
cattgatgaa cagaatgtta acttcttaac catagaagcc aacccagcac tttctgcatt 600
gaaaaccatc atgttacact tcatggagta cgggaaatac aagccaccat tcttgaagac 660
ttcacgcgac atcgtttttg ccctctatga tgacaaaaga cctctttcaa gtcaaatagc 720
tccattgatg attgacctgg ttaactatgc gatagttatc tattcctgca acatttcccg 780
ccttatcagc gttccaacgg tacgtatgat gcttaaagca gctgggacta cttcttacaa 840
ccatactcaa ctaaagctga agaagatcat acccgccgct tcactactgt ctgtttatca 900
tggtgagact gttggtcgtg tgcccatagt cgtttgggag gaacctagag aggaatatcg 960
tttcagattg gatggtgcgc gtgatctccc tcgaggatgg aagaacgaac ttcaaggtgc 1020
gaagaaggcg attgaggatg cttctgactt agctagtagt tatggcatga ctgctgaatt 1080
tgaggaactt cgctctcagt actcaaagat atcagttcac aatggtgttg gcatgaagat 1140
gatcagagat gcattggctg gtgtttcatc ggtattcata actcgcactc ccacagatac 1200
agttcttcaa gagtatgttc atgctccagt cattgagcgc ccaattcccc cacaagattg 1260
gaccgatccc gttggtgtgg taaaatacct gaagaatgac actcagcatt atgtggctcg 1320
aaacttgtat gctacctggc gagaagctgc tgtccaagtt gccaacaatc ccgacaattg 1380
ggacccaaac actcaggcca ttctgcgttc acaatacgta acacctcgcg gcggatcagg 1440
aagtagtgtt aagaaggtgc tcactgataa aggtgtcata ttgaaaaact tctcaaaatc 1500
tggcgctaag agctcaacaa aaatcgtcca agccgctcaa ctggcaagta taccattcac 1560
gcaataccaa gacaccatca tggctcccgt ctctcatgga gtgagaattc aagttcagcg 1620
tcgtagtcgg acgattatgc cattcagcgt tccacagcag caggtctccg ctcctcacac 1680
tctctgcggc aactacatca acaagttctt gaataagagc acaacttcag gttccaacgt 1740
caccgaaaag gtcattccac ttggtatctt cgcctcgtct ccacctactc gtgctgtcaa 1800
cattgacatt aaagcttgtg attcttcgat cacttgggga ttcttcttgt ctgtcatctg 1860
cggtgctatg catgaaggta tggatggaat caatgttggg acgccttttc ttggagtacc 1920
tgccaccttg gttgaagacg gtcttgattt gggtattgtc ggcacacgga gcatctctgg 1980
tatgcagaac atggttcaga agttgtctca actgtatgag cgggggtttg agtacgaagt 2040
taaagatgct ttctctcctg ggaacgcctt cactcatcac actactacat ttccctctgg 2100
ctctactgct acttccacgg aacatacagc gaacaatagt accatgatga aaacgttcct 2160
gatgcactgg ttacctaatc acacgaagga tcttgaattg attgattttg tgaagaagct 2220
tgatgtcaat cgtaactacg tttgccaagg agatgatggt atcatgatac tacccactaa 2280

```
tgatggtcgt ccgatcagtt ctcatcatgt tgaatcaatg ctggaattgc tcagtgtgtt   2340

cggtaaagag agtggatggg tttttgacat tgagtttaac ggatccgctg agtacttgaa   2400

actgttgttt ttgaacggat gcaggatacc taatgtcggt cgtcaccctg tcgttggaaa   2460

ggagcgggct agtcgtgatc aagatgtgat ttggcctggt ggcattgacg ctttcattgg   2520

catgtacaac aatggagttg aggatcaatt tcactggcgt agatggttga agttctcatg   2580

gtcgatggct tgtttccttt cttccaaggc agtcttcatt aagggaaaat ctgacgtgat   2640

tcagtatcca tcctggtctt tcgtgtacct tgggctcccg ccaatacgca ttttcgactc   2700

tccaccttgg atcttctctc catacactcc tggcggcgat ttagggatgt attccatcat   2760

ggtcacaggt aagaagtaca tcgttgatcg catgcaatca agtggttatc agaaagacaa   2820

cactgacttg tccaatgaat ctaccttctt ccggggatat gactacgtca agttcatgaa   2880

tgattgcgga gttctgcctg ggtactacat gtcacaaata cctcgttcac ctgataagac   2940

gaagagaaag gttattggtc ctgagtcacg tgacttgatt gatagtcttc gtaactactt   3000

gttctcagat cagaagctca caatcagagt caactatgga catcgcatcg ttacggatta   3060

tccaggccgc ttgccacgca aattaccatc tcttgacgac gtcccccaaa ggtggtttga   3120

taccgcggtt gaagctgaca tggcgagcac gtatgagatc gaagcgatgg atgttcacct   3180

tcttcgtggc cagttctcta ggtatcaatc cttttctaaa gtgttggaag cctacctgtc   3240

cgtagattgg gagttgactg accttaacat accagcaggc ctgtcattgg atgttccact   3300

agttgccggc tgtgacccta ctaatggtga accatactac aaaatgatgg gtctcggacc   3360

aatgatggaa tccattcaaa cctacttcca cggcacagtg ttcatgagta gagctgtctc   3420

tggtctcgat gttgagtcga tcgatgttgc tctcttgaag atgaaagcct tgaaagtccc   3480

aactgaggtt atcactggat tcttaatgac ttgcggtcta tcaaaaccta aggcatccac   3540

ggtcgccaca aaaatcaact tccaagacat gaaaacggtc caagtcgcaa aactcactgg   3600

attaaatgtt tcggacaaat ggatgagcat gaattttgat cgtttgctgc actcctacgt   3660

ggacgttaag acctatgttt ctgacagtag caatcagata cgtttacctg gcggagctgg   3720

atggttgaga ggagtgatca gattccttgg agctggtgtt gtgatgacta gggttggacc   3780

tcctcagccg gtgagaatct caatcattta tggcggcggt gcacggttgc atagcaaatt   3840

ccttaattgg atggtgtccg atttttagcc cagggtaagt gcggggtagt tgggcttggg   3900

ccgatccttc ttcatc                                                   3916
```

<210> SEQ ID NO 10
<211> LENGTH: 3935
<212> TYPE: DNA
<213> ORGANISM: Piscine reovirus

<400> SEQUENCE: 10

```
gataattgta acgacgaaat ggctacgctt tatgggctac gcataacacg acttaagaac     60

ttaccactac ttgaacgcga cactgaagaa tatacttata aagaaataat aacattttta    120

acaactgatg ttgtgaaaag acttcgtcaa ttccaaaatg gagatcgcga atgttacgca    180

gttcagctcc tctttcctct tacaggatgg tgtccttcag ttgatgtggt tgatggtact    240

agttacaaca cgctcgggaa gttgattaac ttaatacaga ctagttgcgg attgctcgcc    300

cgtcaactca atgtcaggta tcctttggtt ggtgcagcta attccatagt caattcactt    360

gttatcacac aactagttga ttgcgcaatc cgtcatgaat caactgccgc tttgattgaa    420
```

```
caccttttg atgataatgg tcaaatttca tcgttaactg ttcacgctac aacctgggat    480
gaagtcaagt taagcaaaaa tatgactgtg cgtcgacgtg ttgttgagtg tgttgctggg    540
ctgaagtatt ggctgtttcg caacgttaaa ggagctaaga gctttgaaac atggggtaag    600
gactatcctg gttatgccaa cgttcacttc ttcgatgatt ctgctggaaa acaagctgca    660
atacgtcata ttgggaacga cgtgcacata ttccaacatt tcgacaatcc aacttacgct    720
ccacacttgt atgtgccctt ggaaggaaac tattcacgcg acatgtatac tgatagtttc    780
tccactctcg tgcagatgga atgtgtcgtt gatcaggcgc gtgctaactc taacagtgga    840
ttgaagatgg tctctcgaag attcattgag gtgatgaaat gcatacaacg gccaatggga    900
gagactggcg tatctatact ctcaaaattg gatgagattg gaactgtgtt ggctaatggc    960
ggacagttcg agcttgctac cttagatcta agtcgtcgtg aggtgataca ttccatgatt   1020
gacacgattt cagacacacc aaattcctca cgtgcaattc ctttcgacgc taccaggtta   1080
gtcattttcc ttgacactgc ttacactgga cctatgcctt ctactgactt caatgtttca   1140
acatatgagt tcgggttttc tttgattggt tcagtttctg gcaaagcttt ctcacgcccc   1200
atacgttact ctccaaacta caaagatgac ctgggtgact tgcacgatgt taaggaactc   1260
ctcagaacat tcgtgaaacg gaaagatgac gtcacgataa gtaacatttg ggacgggttt   1320
cctttagtcg actttgctaa gtttggaaac gctgcgacca caccggttga tccacgtttg   1380
aggaaggaat ttcccaatga ctactttgat cgggagcaat ctatcaaccg catgttgttt   1440
cgtggttata gaaaaaccat tgatcgctca tgggcaaaag atcaggctgt tttggagact   1500
atcttttcca ttgctggtaa ctggcttact gctaataagt cttatactgc tgcgtatttt   1560
ggagctagtg gcatacatcc taatgacgac caacctctcg ttatcgatcc ctggtcaaag   1620
ggcacaattt ttggtgttcc agccccatca tctaaggttt cccagtatgg atatgacgtt   1680
tccaatggag tgattactga tctgactcga ccctcaccat ctggcacttt ttcattcatc   1740
tattgcgacg tcgatcaggt tcaagatgct ggtgatgatc ttggagtgtg ctaccagata   1800
gttcgcagtc ttttcgacac catcaatgac gctctgacta ctggaggttc ctttgtgatg   1860
aagatcaact ttcccactag acaaatcatg gactatttgg ttgaggttgt cgctcccaag   1920
ttcactgatg gtgttctgat taagccagtt gtgagtaaca acttggagtt gtttgttgga   1980
tttttctgta aggtcgacaa tcgtggatgt cattggaatt ctgactgttc caggttcatg   2040
ttcagactgc acaatcgcta caatcatctt gatcacgctt gtgactacat tccaattatt   2100
ggcaacgcca gagaacatcc acgtgccatc tctcgtcagg agtttgccat cagaaatccg   2160
actagctcta gtgacacttt gagccaagag attgaactga gtctcggtct gttttctcaa   2220
cagtgtgcgg ctaacaccat caccatctca cgtaatctgt tacatggcat gacggaaata   2280
cttgtcagtg gtgttgtgac cgcatcatcc cttaatcgtt gtgaaagact tgattacagt   2340
cctaccattg actcaaccac cattctacat caacatcgcg aaatcgctac tgcctcacca   2400
caactgttcc agttcgaagc atctgaatgg actctccttg ctatgggata caatgagttg   2460
gccgctcggt ttgtcaatgg aagtgcgaaa tctctggttg atgttggtag tggtcctgaa   2520
gggagaagca ttaactacgt tgattctgat atcaaagtta cactctttga tcaaaggaca   2580
ccccacatca atgttgattg gttcgccaat gtggaataca ttcagggaga ttatcttcag   2640
cgtagagatt ggcgtggttg cacctttgat actgccatat gcattttctc ctttggtgcc   2700
gccactgctg gatctccaac gggtatgatt gaatacttaa ccgaacttct tgagatcttg   2760
aaagacgccg gttgtactcg aatcatcatt cagctgaatt gccctctaat gaccaagccc   2820
```

actgtgttg tgagtaagct ggaaatcgac gtgatcaatg acgattatta cttcatcaag 2880
caaggaagag ttgagcccta cgctagccca caggatatat tgggagctat cacgcaagct 2940
ttgcctcaat ctaccgttca gatcaagaca ctggatgacg aattgtcctg gttcccgcgc 3000
atcatttcag aaggtttcag agtgaccaca gaagcaatga gagacgctat cacactttcc 3060
aagttgctac ctctcttcct gatcgagact tcaaaaactc tcttccggcc tgcgaaatac 3120
attggtctag ttgatgaagt gatcaccgca acttggactg ttactgaccc attcgttgac 3180
gtctctgtct acctggaaga cacctctgtt ggattcttca atacgataga taatgaaatc 3240
attggagttg aagttaaagc cgtgttcgat ggacgaggaa cgtatcgagg cactttctcg 3300
actgacaaag ctggagtggt cacgtttgag cagacagaga aagatggcac atctaccata 3360
cttggatctt tcctatgtgt gaccggccca aacgctgttg caatcacctg gcctgcaaac 3420
gaagtcgttg gagataaccc aaacgtcgcc tctctcacca ataacactgg atacgaactg 3480
atagtggcgt atgaatatga cgggacatgg attggagtga acgcttacaa ggctaatgtt 3540
tacgaggacg ccgctggaga tgacaagatg gagtactatc acgtggttgg cgaggagaaa 3600
ctggcttggg cattagtaga tcatcattat ggttctcctg gcgctcgtgt agtgatacct 3660
ttcgtttggc ctgacgttac tgccttgcct ggtgatgtat tagtggctcc accttacgcc 3720
ggtgactggt tggtgaacgt tgatgggaat ttaacggctg aattacacgt tgatgagcct 3780
gatgagatac cagcactctg gactttaatg acacgctcag tagccaacaa tggcagctca 3840
ctttcatata ttggccaagc tggtatctat acgttcttaa agttgccata gcagtggtca 3900
taaaccgatg agccataggc cgttccttct tcatc 3935

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
gtagtgtatg ccactagctc c 21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
gctggtaact ggcttactgc taat 24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
atgtcacaac ttgagtcagt tcc 23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gatacagcta cccaacatga ttga 24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tcagtgcggg gaactctagt ggca 24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gacgaccttg aacgcacgag cgtg 24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tgctggcgat gatcttggag tatgc 25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
acaccatcag tgaacttagg agcaaca 27

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tgctaacact ccaggagtca ttg 23

<210> SEQ ID NO 20

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

tgaatccgct gcagatgagt a                                          21

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21

cgccggtagc tct                                                   13

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

acagtcgcgg ttcaaacga                                             19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

aaggcgtcgc ttagcttcaa                                            20

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24

agaccagaca gacgc                                                 15

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

ccacagacaa gccccttcgt                                            20

<210> SEQ ID NO 26
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

ccttcagggt tccagtctcc a                                              21


<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27

aggtacagtt ccaataccac cgattttgta aacg                                34


<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28

caccatcagt gaacttagga gcaac                                          25


<210> SEQ ID NO 29
<211> LENGTH: 1282
<212> TYPE: PRT
<213> ORGANISM: Piscine reovirus

<400> SEQUENCE: 29

Met Glu Arg Leu Lys Arg Lys Asp Lys Tyr Lys Asn Thr Asn Thr Lys
1               5                   10                  15

Glu Asn Thr Gln Glu Leu Thr Val Asp Glu Ser Ala Val Ser Ser Asn
            20                  25                  30

Asn Pro Thr Gly Lys Thr Thr Asp Asn Gly Gly Val Gly Lys Asn Arg
        35                  40                  45

Gly Ser Leu Pro Ala Ile Ser Ala Ser Asp Ser Asp Ser Ser Glu Glu
    50                  55                  60

Glu Ala Ile Val Glu Val Gln Arg Ile Lys Lys Ser Lys Ala Gln Lys
65                  70                  75                  80

Lys Ser Thr Lys Leu Ala Thr Thr Thr Gln Asn Asp Ser Asn Glu Ser
                85                  90                  95

Asn Ile Val Thr Gln Pro Gly Met Gly Met Ser Ala Asn Val Ser Thr
            100                 105                 110

Ile Asn Val Leu Pro Pro Thr Val Thr Met Pro Leu Gln Thr Thr Gln
        115                 120                 125

Ser Ser Pro Gly Pro Ala Val Asp Gln Ser Gly Glu Thr Lys Leu Gly
    130                 135                 140

Arg Ser Ser Asn Val Ser Gly Lys Glu Ala Ala Met Gln Ala Pro Ala
145                 150                 155                 160

Val Asp Arg Ser Glu Ile Thr Asp Asn Pro Arg Tyr Asp Pro Thr Thr
                165                 170                 175

Ser Thr Gly Thr Thr Ser Cys Pro Leu Cys Phe Met Thr Leu Ser Ser
            180                 185                 190
```

-continued

```
Val Pro Asp Leu Leu Leu His Ile Ser Met Arg His Ala Pro Ile Asp
        195                 200                 205

Ser Phe Ser Thr Thr Ala Pro Gln Ile Gln Asp Ala Glu Arg Gln Phe
    210                 215                 220

Ile Thr Ile Trp Ser Ala His Asn Ala Ala Ala Leu Ser Ser Leu Ser
225                 230                 235                 240

Thr Gly Leu Thr Thr Ser Ser Ser Phe Leu Ser Lys Val Pro Pro Arg
                245                 250                 255

Leu Phe Val Phe Asp Asp Gly Ile Cys Ser Ser Phe Arg Phe Met Thr
            260                 265                 270

Ala Val Glu Ala Arg Tyr Leu Pro Glu Val Arg Gly Tyr Ala Trp Tyr
        275                 280                 285

Asp Glu Ile Tyr Asp Ile Ile Leu Pro Phe Pro Ala Ser Ala Val Val
    290                 295                 300

Arg Ile Val Leu Asp Thr Asp Trp Ala Met Val Ser Asp Glu Thr Leu
305                 310                 315                 320

Pro Ile Lys Leu Thr Thr Leu Leu Pro Thr Leu Ser Asn Val Gly Leu
                325                 330                 335

Leu Arg Gln Val Leu Thr Val Leu Ser Asp Asn Ser Lys Tyr Asn Pro
            340                 345                 350

Val Trp Ala Arg Ala Asn Val Ile Val Met Gly Val Lys Phe Ile Leu
        355                 360                 365

Ala Asn Leu Val Ile Asn Arg Ser Ser Ser Trp Ala Gln Asp Ser Thr
    370                 375                 380

Pro Ser Val Ser Gly Arg Leu Leu Arg Thr Val Pro Gly Lys Pro Glu
385                 390                 395                 400

Tyr Trp Pro Leu Met Tyr Pro Arg Arg Thr Leu Asn Ala Asn Val Ser
                405                 410                 415

Lys Ile Ser Arg Phe Val Glu Gln Thr Gln Ala Glu Arg Thr Gly Arg
            420                 425                 430

Val Asp Arg Ala Met Leu Tyr Gln Gly Glu Lys Val Ile Tyr Thr Asp
        435                 440                 445

Val Ala Glu Thr Cys Asp Thr Leu Thr Val Arg Leu Arg Asp Met Trp
    450                 455                 460

Thr Gly Lys Ile Phe Lys Met His Tyr Thr His Ser Asp Ile Ala Leu
465                 470                 475                 480

Ala Leu Ser Glu Cys Ala Arg Val Val Ser Phe Ser Ala Val Met Ala
                485                 490                 495

Leu Ser Pro Arg Thr Ile Leu Pro Cys Arg Ala Thr Thr Asp Glu Arg
            500                 505                 510

Lys Leu Ala Gln Val Leu Asn Ile Ala Arg Leu Gly Asp Leu Arg Leu
        515                 520                 525

Arg Ile Glu Pro Ile Ile Gln Ser Ala Ala Asp Thr Leu Arg Ser Val
    530                 535                 540

Thr Met Leu Glu Ile Asn Pro Lys Ile Leu Thr Ala Val Leu Asn Arg
545                 550                 555                 560

Ile Cys Glu Asn Gln Thr Gln Ser Val Thr Val Thr Gly Thr Ile Leu
                565                 570                 575

Arg Leu Leu Ser Ser Ala Thr Thr Asp Ser Ser Ala Phe Trp Thr Cys
            580                 585                 590

Ile Ala Ser Trp Leu Tyr Asn Gly Ile Val Thr Thr Thr Leu Arg Gln
        595                 600                 605
```

-continued

```
Gln Asp Tyr Pro Asn Pro Thr Ala Ser Ile Thr Asp Tyr Thr Ala Leu
    610                 615                 620

Trp Ser Ala Leu Ile Val Ser Leu Val Ser Pro Leu Thr Asn Asp Pro
625                 630                 635                 640

Asn Ala Pro Val Lys Ile Phe Met Thr Met Ala Asn Leu Phe Asn Gly
                645                 650                 655

Tyr Glu Arg Ile Pro Met Asn Asn Ala Ser Met Thr Gln Gly Thr Pro
            660                 665                 670

Pro Trp Ala Phe Asn Asn Pro Asn Lys Trp Pro Ala Cys Phe Ile Gln
        675                 680                 685

Pro Arg Asn Ile Asn Gln Asn Ile Ala Pro Phe Met Arg Ala Trp Ala
    690                 695                 700

Asp Leu Ile His Arg Tyr Trp Pro Gln Pro Gly Val Val Asn Tyr Gly
705                 710                 715                 720

Ser Pro His His Leu Gly Ala Thr Glu Leu Leu Val Glu Asp Gly Gln
                725                 730                 735

Ile Val Thr Pro Leu Pro Val Gln Pro Gln Gln Phe Glu Tyr Ala Ala
            740                 745                 750

Leu Asp Arg Asp Asn Glu Met Ser Thr Trp Ile Asn Gln Val Cys Asn
        755                 760                 765

Phe Phe Ile Arg Cys Ile Asn Gly Thr Asp Leu Arg Thr Ala Ser Asn
    770                 775                 780

Gln Ala Thr Gln Gln Ala Leu Ile Ser Ala Ile Ser Gln Leu Lys Thr
785                 790                 795                 800

Ser Pro Ser Leu Thr Tyr Gly Tyr Met Ser Arg Tyr Leu Pro Tyr Glu
                805                 810                 815

Leu Ala Met Ile Ser Pro Thr Leu Ala Leu Pro Pro Phe Gln Ile Pro
            820                 825                 830

Phe Gln Arg Leu Asn Val Asn Asp Ile Val Tyr Gln Ile Gly Val Arg
        835                 840                 845

Arg His Val Val Arg Asp Gln Val Glu Pro Ala Leu Asp Thr Ser Ser
    850                 855                 860

Thr Leu Glu Thr Ile Gly Gln Leu Ile Glu Ile Asp Ala Gln Ala Leu
865                 870                 875                 880

Leu Val Ser Leu Leu Ser Gly Thr Met Asn Ala Lys Val Leu Pro Ser
                885                 890                 895

Val His Tyr Ala Glu Lys Ile Thr Pro Leu Tyr Met Asp Asp Asp Phe
            900                 905                 910

Phe Ala Pro His Gln Arg Ala Val Val Val Ser Glu Ala Tyr Ser Leu
        915                 920                 925

Val Arg Thr Ile Ile Ser Gln Ile Ser Asp Thr Arg Gly Pro Gln Leu
    930                 935                 940

Asn Pro Leu Ala Trp Ile Pro Ala Pro Asn Ala Ser Ser Pro Val Ser
945                 950                 955                 960

Ala Glu Val Ala Arg Leu Val Asn Asp Met Ile Lys Glu Ala Phe Asp
                965                 970                 975

Met Pro Gly Glu Leu Leu Glu Gly Leu Ile Gly Tyr Gly Asp Pro Arg
            980                 985                 990

Tyr Thr Gln Val Glu Ile Val Ala  Gln Arg Cys Arg Ala  Ala Pro Leu
        995                  1000                 1005

Arg Phe  Glu Pro Leu Ile Pro  Pro Ser Val Leu Ala  Gln Glu Leu
    1010                 1015                 1020

Gln Leu  Val Glu Asn Val Ile  Thr Ala Glu Pro Asn  Leu Phe Gly
```

```
    1025                1030                1035

Leu Ala  Thr Gly Asp Leu Tyr  Leu Glu Arg Ile Asp  Thr Ser Ala
    1040                1045                1050

Gly Phe  Ser Gly Leu Asn Val  Ile Gly Trp Glu Gln  Trp Asp Ala
    1055                1060                1065

Asn Thr  Pro Gly Val Ile Val  Ala Gly Ser Ser Leu  Leu Ile Cys
    1070                1075                1080

Ser Gly  Phe Asn Gly Val Asp  Pro Met Ile Met Asp  Ala Asp Gly
    1085                1090                1095

Val Glu  Arg Pro Ile Thr Gly  Arg Trp Val Val Thr  Leu Glu Ala
    1100                1105                1110

Trp Arg  Ser Ser Val Val Thr  Val Gln Lys Leu Leu  Leu Pro Arg
    1115                1120                1125

Ile Arg  Ala Gly Lys Leu Ala  Val Arg Ile Leu Val  Gly Ile Phe
    1130                1135                1140

Pro Tyr  Thr Ile Asn Tyr Tyr  Glu Pro Ala Val Gly  Ile Asp Glu
    1145                1150                1155

Trp Lys  Leu Leu Ser Asp Trp  Ala Ser Met Cys Glu  Pro Thr Gly
    1160                1165                1170

Ile Pro  Ala Ile Pro Phe Thr  Ala Pro Val Pro Ser  Asp Val Ser
    1175                1180                1185

Val Val  Thr Ala Ala Cys Val  Arg Tyr Leu Arg Cys  Ser Thr Phe
    1190                1195                1200

Asn Glu  Gly Ser Leu Met Ala  Thr Asn Ala Gly Ser  Pro Arg Thr
    1205                1210                1215

Val Phe  Gly Gln Ser Val Glu  Phe Asp Ile Gly Arg  Trp Met Gln
    1220                1225                1230

Leu Cys  Asp Leu Asn Thr Gly  Val Asp Glu Ile Gln  Leu Pro Asn
    1235                1240                1245

Met Ile  Glu Phe Tyr Gln Ile  Phe Arg Arg Tyr Asn  Ile Thr Gln
    1250                1255                1260

Thr Glu  Leu Thr Gln Val Val  Thr Leu Thr Gly Thr  Leu Thr His
    1265                1270                1275

Pro Val  Leu Asn
    1280


<210> SEQ ID NO 30
<211> LENGTH: 1290
<212> TYPE: PRT
<213> ORGANISM: Piscine reovirus

<400> SEQUENCE: 30

Met Ala Thr Leu Tyr Gly Leu Arg Ile Thr Arg Leu Lys Asn Leu Pro
1               5                   10                  15

Leu Leu Glu Arg Asp Thr Glu Glu Tyr Thr Tyr Lys Glu Ile Ile Thr
            20                  25                  30

Phe Leu Thr Thr Asp Val Val Lys Arg Leu Arg Gln Phe Gln Asn Gly
        35                  40                  45

Asp Arg Glu Cys Tyr Ala Val Gln Leu Leu Phe Pro Leu Thr Gly Trp
    50                  55                  60

Cys Pro Ser Val Asp Val Val Asp Gly Thr Ser Tyr Asn Thr Leu Gly
65                  70                  75                  80

Lys Leu Ile Asn Leu Ile Gln Thr Ser Cys Gly Leu Leu Ala Arg Gln
                85                  90                  95
```

-continued

```
Leu Asn Val Arg Tyr Pro Leu Val Gly Ala Ala Asn Ser Ile Val Asn
            100                 105                 110

Ser Leu Val Ile Thr Gln Leu Val Asp Cys Ala Ile Arg His Glu Ser
        115                 120                 125

Thr Ala Ala Leu Ile Glu His Leu Phe Asp Asp Asn Gly Gln Ile Ser
    130                 135                 140

Ser Leu Thr Val His Ala Thr Thr Trp Asp Glu Val Lys Leu Ser Lys
145                 150                 155                 160

Asn Met Thr Val Arg Arg Arg Val Val Glu Cys Val Ala Gly Leu Lys
                165                 170                 175

Tyr Trp Leu Phe Arg Asn Val Lys Gly Ala Lys Ser Phe Glu Thr Trp
            180                 185                 190

Gly Lys Asp Tyr Pro Gly Tyr Ala Asn Val His Phe Phe Asp Asp Ser
        195                 200                 205

Ala Gly Lys Gln Ala Ala Ile Arg His Ile Gly Asn Asp Val His Ile
    210                 215                 220

Phe Gln His Phe Asp Asn Pro Thr Tyr Ala Pro His Leu Tyr Val Pro
225                 230                 235                 240

Leu Glu Gly Asn Tyr Ser Arg Asp Met Tyr Thr Asp Ser Phe Ser Thr
                245                 250                 255

Leu Val Gln Met Glu Cys Val Val Asp Gln Ala Arg Ala Asn Ser Asn
            260                 265                 270

Ser Gly Leu Lys Met Val Ser Arg Arg Phe Ile Glu Val Met Lys Cys
        275                 280                 285

Ile Gln Arg Pro Met Gly Glu Thr Gly Val Ser Ile Leu Ser Lys Leu
    290                 295                 300

Asp Glu Ile Gly Thr Val Leu Ala Asn Gly Gly Gln Phe Glu Leu Ala
305                 310                 315                 320

Thr Leu Asp Leu Ser Arg Arg Glu Val Ile His Ser Met Ile Asp Thr
                325                 330                 335

Ile Ser Asp Thr Pro Asn Ser Ser Arg Ala Ile Pro Phe Asp Ala Thr
            340                 345                 350

Arg Leu Val Ile Phe Leu Asp Thr Ala Tyr Thr Gly Pro Met Pro Ser
        355                 360                 365

Thr Asp Phe Asn Val Ser Thr Tyr Glu Phe Gly Phe Ser Leu Ile Gly
    370                 375                 380

Ser Val Ser Gly Lys Ala Phe Ser Arg Pro Ile Arg Tyr Ser Pro Asn
385                 390                 395                 400

Tyr Lys Asp Asp Leu Gly Asp Leu His Asp Val Lys Glu Leu Leu Arg
                405                 410                 415

Thr Phe Val Lys Arg Lys Asp Asp Val Thr Ile Ser Asn Ile Trp Asp
            420                 425                 430

Gly Phe Pro Leu Val Asp Phe Ala Lys Phe Gly Asn Ala Ala Thr Thr
        435                 440                 445

Pro Val Asp Pro Arg Leu Arg Lys Glu Phe Pro Asn Asp Tyr Phe Asp
    450                 455                 460

Arg Glu Gln Ser Ile Asn Arg Met Leu Phe Arg Gly Tyr Arg Lys Thr
465                 470                 475                 480

Ile Asp Arg Ser Trp Ala Lys Asp Gln Ala Val Leu Glu Thr Ile Phe
                485                 490                 495

Ser Ile Ala Gly Asn Trp Leu Thr Ala Asn Lys Ser Tyr Thr Ala Ala
            500                 505                 510

Tyr Phe Gly Ala Ser Gly Ile His Pro Asn Asp Asp Gln Pro Leu Val
```

-continued

```
        515                 520                 525

Ile Asp Pro Trp Ser Lys Gly Thr Ile Phe Gly Val Pro Ala Pro Ser
    530                 535                 540

Ser Lys Val Ser Gln Tyr Gly Tyr Asp Val Ser Asn Gly Val Ile Thr
545                 550                 555                 560

Asp Leu Thr Arg Pro Ser Pro Ser Gly Thr Phe Ser Phe Ile Tyr Cys
                565                 570                 575

Asp Val Asp Gln Val Gln Asp Ala Gly Asp Asp Leu Gly Val Cys Tyr
            580                 585                 590

Gln Ile Val Arg Ser Leu Phe Asp Thr Ile Asn Asp Ala Leu Thr Thr
        595                 600                 605

Gly Gly Ser Phe Val Met Lys Ile Asn Phe Pro Thr Arg Gln Ile Met
    610                 615                 620

Asp Tyr Leu Val Glu Val Val Ala Pro Lys Phe Thr Asp Gly Val Leu
625                 630                 635                 640

Ile Lys Pro Val Val Ser Asn Asn Leu Glu Leu Phe Val Gly Phe Phe
                645                 650                 655

Cys Lys Val Asp Asn Arg Gly Cys His Trp Asn Ser Asp Cys Ser Arg
            660                 665                 670

Phe Met Phe Arg Leu His Asn Arg Tyr Asn His Leu Asp His Ala Cys
        675                 680                 685

Asp Tyr Ile Pro Ile Ile Gly Asn Ala Arg Glu His Pro Arg Ala Ile
    690                 695                 700

Ser Arg Gln Glu Phe Ala Ile Arg Asn Pro Thr Ser Ser Ser Asp Thr
705                 710                 715                 720

Leu Ser Gln Glu Ile Glu Leu Ser Leu Gly Leu Phe Ser Gln Gln Cys
                725                 730                 735

Ala Ala Asn Thr Ile Thr Ile Ser Arg Asn Leu Leu His Gly Met Thr
            740                 745                 750

Glu Ile Leu Val Ser Gly Val Val Thr Ala Ser Ser Leu Asn Arg Cys
        755                 760                 765

Glu Arg Leu Asp Tyr Ser Pro Thr Ile Asp Ser Thr Thr Ile Leu His
    770                 775                 780

Gln His Arg Glu Ile Ala Thr Ala Ser Pro Gln Leu Phe Gln Phe Glu
785                 790                 795                 800

Ala Ser Glu Trp Thr Leu Leu Ala Met Gly Tyr Asn Glu Leu Ala Ala
                805                 810                 815

Arg Phe Val Asn Gly Ser Ala Lys Ser Leu Val Asp Val Gly Ser Gly
            820                 825                 830

Pro Glu Gly Arg Ser Ile Asn Tyr Val Asp Ser Asp Ile Lys Val Thr
        835                 840                 845

Leu Phe Asp Gln Arg Thr Pro His Ile Asn Val Asp Trp Phe Ala Asn
    850                 855                 860

Val Glu Tyr Ile Gln Gly Asp Tyr Leu Gln Arg Arg Asp Trp Arg Gly
865                 870                 875                 880

Cys Thr Phe Asp Thr Ala Ile Cys Ile Phe Ser Phe Gly Ala Ala Thr
                885                 890                 895

Ala Gly Ser Pro Thr Gly Met Ile Glu Tyr Leu Thr Glu Leu Leu Glu
            900                 905                 910

Ile Leu Lys Asp Ala Gly Cys Thr Arg Ile Ile Ile Gln Leu Asn Cys
        915                 920                 925

Pro Leu Met Thr Lys Pro Thr Gly Val Val Ser Lys Leu Glu Ile Asp
    930                 935                 940
```

-continued

Val Ile Asn Asp Asp Tyr Tyr Phe Ile Lys Gln Gly Arg Val Glu Pro
945 950 955 960

Tyr Ala Ser Pro Gln Asp Ile Leu Gly Ala Ile Thr Gln Ala Leu Pro
965 970 975

Gln Ser Thr Val Gln Ile Lys Thr Leu Asp Asp Glu Leu Ser Trp Phe
980 985 990

Pro Arg Ile Ile Ser Glu Gly Phe Arg Val Thr Thr Glu Ala Met Arg
995 1000 1005

Asp Ala Ile Thr Leu Ser Lys Leu Leu Pro Leu Phe Leu Ile Glu
1010 1015 1020

Thr Ser Lys Thr Leu Phe Arg Pro Ala Lys Tyr Ile Gly Leu Val
1025 1030 1035

Asp Glu Val Ile Thr Ala Thr Trp Thr Val Thr Asp Pro Phe Val
1040 1045 1050

Asp Val Ser Val Tyr Leu Glu Asp Thr Ser Val Gly Phe Phe Asn
1055 1060 1065

Thr Ile Asp Asn Glu Ile Ile Gly Val Glu Val Lys Ala Val Phe
1070 1075 1080

Asp Gly Arg Gly Thr Tyr Arg Gly Thr Phe Ser Thr Asp Lys Ala
1085 1090 1095

Gly Val Val Thr Phe Glu Gln Thr Glu Lys Asp Gly Thr Ser Thr
1100 1105 1110

Ile Leu Gly Ser Phe Leu Cys Val Thr Gly Pro Asn Ala Val Ala
1115 1120 1125

Ile Thr Trp Pro Ala Asn Glu Val Val Gly Asp Asn Pro Asn Val
1130 1135 1140

Ala Ser Leu Thr Asn Asn Thr Gly Tyr Glu Leu Ile Val Ala Tyr
1145 1150 1155

Glu Tyr Asp Gly Thr Trp Ile Gly Val Asn Ala Tyr Lys Ala Asn
1160 1165 1170

Val Tyr Glu Asp Ala Ala Gly Asp Asp Lys Met Glu Tyr Tyr His
1175 1180 1185

Val Val Gly Glu Glu Lys Leu Ala Trp Ala Leu Val Asp His His
1190 1195 1200

Tyr Gly Ser Pro Gly Ala Arg Val Val Ile Pro Phe Val Trp Pro
1205 1210 1215

Asp Val Thr Ala Leu Pro Gly Asp Val Leu Val Ala Pro Pro Tyr
1220 1225 1230

Ala Gly Asp Trp Leu Val Asn Val Asp Gly Asn Leu Thr Ala Glu
1235 1240 1245

Leu His Val Asp Glu Pro Asp Glu Ile Pro Ala Leu Trp Thr Leu
1250 1255 1260

Met Thr Arg Ser Val Ala Asn Asn Gly Ser Ser Leu Ser Tyr Ile
1265 1270 1275

Gly Gln Ala Gly Ile Tyr Thr Phe Leu Lys Leu Pro
1280 1285 1290

<210> SEQ ID NO 31
<211> LENGTH: 1286
<212> TYPE: PRT
<213> ORGANISM: Piscine reovirus

<400> SEQUENCE: 31

Met Glu Lys Pro Lys Ala Leu Val Asn Gln Leu Pro Glu Asp Leu Glu

-continued

```
1               5                   10                  15

Asn Leu Ser Val Ala Leu Ser Gly Thr Ile Glu Leu Thr Ala Asp Ile
            20                  25                  30

Trp Thr Asn Ala Ser Lys Thr Phe Arg Thr Thr Gln Arg His Glu Val
        35                  40                  45

Tyr Asp Ile Ile Asn Lys Ile Glu Phe Ile Asp Ser Phe Leu Val Pro
    50                  55                  60

Ser Ser Leu Phe Gln Pro Pro Pro His Lys Arg Tyr Trp Asp Val Asp
65                  70                  75                  80

Val Arg Gln Arg Val Val Arg Val Pro Lys Cys Ala Val Pro Asp Asp
                85                  90                  95

Val Tyr Leu Pro His Ala Asn Leu Thr Asp Val Leu Glu Ile Asn Thr
            100                 105                 110

Glu Ser Ile His Lys Tyr Gly Gln Leu Arg Lys Glu Ile Gln Ala Ala
        115                 120                 125

Ala Lys Arg Leu Asp Pro Thr Ala Arg Ile Ala Glu Thr Phe Tyr Asn
    130                 135                 140

Leu Ser Val Tyr Gln Ala Asn Gln Ile Lys Phe Pro Leu Glu Arg Phe
145                 150                 155                 160

Leu Leu Cys Leu Val Val Ser Tyr Ala His Glu Leu Ser Pro Ser Pro
                165                 170                 175

Leu Leu Ile Asp Glu Gln Asn Val Asn Phe Leu Thr Ile Glu Ala Asn
            180                 185                 190

Pro Ala Leu Ser Ala Leu Lys Thr Ile Met Leu His Phe Met Glu Tyr
        195                 200                 205

Gly Lys Tyr Lys Pro Pro Phe Leu Lys Thr Ser Arg Asp Ile Val Phe
    210                 215                 220

Ala Leu Tyr Asp Asp Lys Arg Pro Leu Ser Ser Gln Ile Ala Pro Leu
225                 230                 235                 240

Met Ile Asp Leu Val Asn Tyr Ala Ile Val Ile Tyr Ser Cys Asn Ile
                245                 250                 255

Ser Arg Leu Ile Ser Val Pro Thr Val Arg Met Met Leu Lys Ala Ala
            260                 265                 270

Gly Thr Thr Ser Tyr Asn His Thr Gln Leu Lys Leu Lys Lys Ile Ile
        275                 280                 285

Pro Ala Ala Ser Leu Leu Ser Val Tyr His Gly Glu Thr Val Gly Arg
    290                 295                 300

Val Pro Ile Val Val Trp Glu Glu Pro Arg Glu Glu Tyr Arg Phe Arg
305                 310                 315                 320

Leu Asp Gly Ala Arg Asp Leu Pro Arg Gly Trp Lys Asn Glu Leu Gln
                325                 330                 335

Gly Ala Lys Lys Ala Ile Glu Asp Ala Ser Asp Leu Ala Ser Ser Tyr
            340                 345                 350

Gly Met Thr Ala Glu Phe Glu Glu Leu Arg Ser Gln Tyr Ser Lys Ile
        355                 360                 365

Ser Val His Asn Gly Val Gly Met Lys Met Ile Arg Asp Ala Leu Ala
    370                 375                 380

Gly Val Ser Ser Val Phe Ile Thr Arg Thr Pro Thr Asp Thr Val Leu
385                 390                 395                 400

Gln Glu Tyr Val His Ala Pro Val Ile Glu Arg Pro Ile Pro Pro Gln
                405                 410                 415

Asp Trp Thr Asp Pro Val Gly Val Val Lys Tyr Leu Lys Asn Asp Thr
            420                 425                 430
```

-continued

```
Gln His Tyr Val Ala Arg Asn Leu Tyr Ala Thr Trp Arg Glu Ala Ala
        435                 440                 445

Val Gln Val Ala Asn Asn Pro Asp Asn Trp Asp Pro Asn Thr Gln Ala
    450                 455                 460

Ile Leu Arg Ser Gln Tyr Val Thr Pro Arg Gly Gly Ser Gly Ser Ser
465                 470                 475                 480

Val Lys Lys Val Leu Thr Asp Lys Gly Val Ile Leu Lys Asn Phe Ser
                485                 490                 495

Lys Ser Gly Ala Lys Ser Ser Thr Lys Ile Val Gln Ala Ala Gln Leu
            500                 505                 510

Ala Ser Ile Pro Phe Thr Gln Tyr Gln Asp Thr Ile Met Ala Pro Val
        515                 520                 525

Ser His Gly Val Arg Ile Gln Val Gln Arg Arg Ser Arg Thr Ile Met
    530                 535                 540

Pro Phe Ser Val Pro Gln Gln Gln Val Ser Ala Pro His Thr Leu Cys
545                 550                 555                 560

Gly Asn Tyr Ile Asn Lys Phe Leu Asn Lys Ser Thr Thr Ser Gly Ser
                565                 570                 575

Asn Val Thr Glu Lys Val Ile Pro Leu Gly Ile Phe Ala Ser Ser Pro
            580                 585                 590

Pro Thr Arg Ala Val Asn Ile Asp Ile Lys Ala Cys Asp Ser Ser Ile
        595                 600                 605

Thr Trp Gly Phe Phe Leu Ser Val Ile Cys Gly Ala Met His Glu Gly
    610                 615                 620

Met Asp Gly Ile Asn Val Gly Thr Pro Phe Leu Gly Val Pro Ala Thr
625                 630                 635                 640

Leu Val Glu Asp Gly Leu Asp Leu Gly Ile Val Gly Thr Arg Ser Ile
                645                 650                 655

Ser Gly Met Gln Asn Met Val Gln Lys Leu Ser Gln Leu Tyr Glu Arg
            660                 665                 670

Gly Phe Glu Tyr Glu Val Lys Asp Ala Phe Ser Pro Gly Asn Ala Phe
        675                 680                 685

Thr His His Thr Thr Thr Phe Pro Ser Gly Ser Thr Ala Thr Ser Thr
    690                 695                 700

Glu His Thr Ala Asn Asn Ser Thr Met Met Lys Thr Phe Leu Met His
705                 710                 715                 720

Trp Leu Pro Asn His Thr Lys Asp Leu Glu Leu Ile Asp Phe Val Lys
                725                 730                 735

Lys Leu Asp Val Asn Arg Asn Tyr Val Cys Gln Gly Asp Asp Gly Ile
            740                 745                 750

Met Ile Leu Pro Thr Asn Asp Gly Arg Pro Ile Ser Ser His His Val
        755                 760                 765

Glu Ser Met Leu Glu Leu Leu Ser Val Phe Gly Lys Glu Ser Gly Trp
    770                 775                 780

Val Phe Asp Ile Glu Phe Asn Gly Ser Ala Glu Tyr Leu Lys Leu Leu
785                 790                 795                 800

Phe Leu Asn Gly Cys Arg Ile Pro Asn Val Gly Arg His Pro Val Val
                805                 810                 815

Gly Lys Glu Arg Ala Ser Arg Asp Gln Asp Val Ile Trp Pro Gly Gly
            820                 825                 830

Ile Asp Ala Phe Ile Gly Met Tyr Asn Asn Gly Val Glu Asp Gln Phe
        835                 840                 845
```

-continued

```
His Trp Arg Arg Trp Leu Lys Phe Ser Trp Ser Met Ala Cys Phe Leu
    850                 855                 860

Ser Ser Lys Ala Val Phe Ile Lys Gly Lys Ser Asp Val Ile Gln Tyr
865                 870                 875                 880

Pro Ser Trp Ser Phe Val Tyr Leu Gly Leu Pro Pro Ile Arg Ile Phe
                885                 890                 895

Asp Ser Pro Pro Trp Ile Phe Ser Pro Tyr Thr Pro Gly Gly Asp Leu
            900                 905                 910

Gly Met Tyr Ser Ile Met Val Thr Gly Lys Lys Tyr Ile Val Asp Arg
        915                 920                 925

Met Gln Ser Ser Gly Tyr Gln Lys Asp Asn Thr Asp Leu Ser Asn Glu
    930                 935                 940

Ser Thr Phe Phe Arg Gly Tyr Asp Tyr Val Lys Phe Met Asn Asp Cys
945                 950                 955                 960

Gly Val Leu Pro Gly Tyr Tyr Met Ser Gln Ile Pro Arg Ser Pro Asp
                965                 970                 975

Lys Thr Lys Arg Lys Val Ile Gly Pro Glu Ser Arg Asp Leu Ile Asp
            980                 985                 990

Ser Leu Arg Asn Tyr Leu Phe Ser  Asp Gln Lys Leu Thr  Ile Arg Val
        995                 1000                1005

Asn Tyr  Gly His Arg Ile Val  Thr Asp Tyr Pro Gly  Arg Leu Pro
    1010                 1015                 1020

Arg Lys  Leu Pro Ser Leu Asp  Asp Val Pro Gln Arg  Trp Phe Asp
    1025                 1030                 1035

Thr Ala  Val Glu Ala Asp Met  Ala Ser Thr Tyr Glu  Ile Glu Ala
    1040                 1045                 1050

Met Asp  Val His Leu Leu Arg  Gly Gln Phe Ser Arg  Tyr Gln Ser
    1055                 1060                 1065

Phe Ser  Lys Val Leu Glu Ala  Tyr Leu Ser Val Asp  Trp Glu Leu
    1070                 1075                 1080

Thr Asp  Leu Asn Ile Pro Ala  Gly Leu Ser Leu Asp  Val Pro Leu
    1085                 1090                 1095

Val Ala  Gly Cys Asp Pro Thr  Asn Gly Glu Pro Tyr  Tyr Lys Met
    1100                 1105                 1110

Met Gly  Leu Gly Pro Met Met  Glu Ser Ile Gln Thr  Tyr Phe His
    1115                 1120                 1125

Gly Thr  Val Phe Met Ser Arg  Ala Val Ser Gly Leu  Asp Val Glu
    1130                 1135                 1140

Ser Ile  Asp Val Ala Leu Leu  Lys Met Lys Ala Leu  Lys Val Pro
    1145                 1150                 1155

Thr Glu  Val Ile Thr Gly Phe  Leu Met Thr Cys Gly  Leu Ser Lys
    1160                 1165                 1170

Pro Lys  Ala Ser Thr Val Ala  Thr Lys Ile Asn Phe  Gln Asp Met
    1175                 1180                 1185

Lys Thr  Val Gln Val Ala Lys  Leu Thr Gly Leu Asn  Val Ser Asp
    1190                 1195                 1200

Lys Trp  Met Ser Met Asn Phe  Asp Arg Leu Leu His  Ser Tyr Val
    1205                 1210                 1215

Asp Val  Lys Thr Tyr Val Ser  Asp Ser Ser Asn Gln  Ile Arg Leu
    1220                 1225                 1230

Pro Gly  Gly Ala Gly Trp Leu  Arg Gly Val Ile Arg  Phe Leu Gly
    1235                 1240                 1245

Ala Gly  Val Val Met Thr Arg  Val Gly Pro Pro Gln  Pro Val Arg
```

-continued

```
    1250                1255                1260

Ile Ser  Ile Ile Tyr Gly Gly  Gly Ala Arg Leu His  Ser Lys Phe
    1265                1270                1275

Leu Asn  Trp Met Val Ser Asp  Phe
    1280                1285


<210> SEQ ID NO 32
<211> LENGTH: 687
<212> TYPE: PRT
<213> ORGANISM: Piscine reovirus

<400> SEQUENCE: 32

Met Gly Asn Tyr Gln Thr Ser Asn Asn Gln Phe Trp Val Thr Gly Asp
1               5                   10                  15

Gly Asn Asp Phe Ser Ala Glu Gly Gly Leu Asp Ser Thr Asn Ala Ala
            20                  25                  30

Ser Leu Asp Phe Lys Ala Gly Lys Thr Asn Pro Gly Gly His Met Tyr
        35                  40                  45

Val Ile Ser Gly Asp Asn Thr Ser Asp Val Val Lys Trp Asp Ser Leu
    50                  55                  60

Thr Pro Leu Tyr Gly Ile Asp Gly Gln Met Val Val Val Leu Thr Ala
65                  70                  75                  80

Val Ala Met Ser Thr Phe Glu Lys Met Val Asn Leu Ile Glu Met Tyr
                85                  90                  95

Arg Pro Leu Leu Glu Ala Ser Gln Gln Met Ala Cys Tyr Arg Asp Trp
            100                 105                 110

Lys Lys Asp Ile Val Leu Leu Asp Gly Tyr Val Gly Ser Thr Pro Gln
        115                 120                 125

Ser Ala Val Thr Asn Phe Val Thr Gly Ala Ser Val Ile Asn Leu Arg
    130                 135                 140

Glu Leu Arg Ser Leu Gly Lys Met Tyr Gln Asn Ile Leu Gly Val Ile
145                 150                 155                 160

Ala Asn Tyr Asp Arg Asp Ile Gln Val Ala Leu Ser Leu Ile Pro His
                165                 170                 175

Ser Thr Pro Ile Gly Ser Leu Thr Ala Asp Met His Ser Ile Leu Arg
            180                 185                 190

Met Phe Ser Leu Ser Leu Lys Pro Thr Asn Val Cys Tyr Leu Tyr Pro
        195                 200                 205

Glu Ala Ala Leu Gln Val Ile Arg Ala Ile Ser Pro Thr Val Arg Asn
    210                 215                 220

Val Asp Thr Gln Gln Gly Gly Ser Ile Val Glu Thr Leu Asn Leu Phe
225                 230                 235                 240

Glu Pro Val Phe Asn Gly Thr Gly Pro Asn Gln Pro Pro Leu Thr Asp
                245                 250                 255

Gln Ser Glu Val Arg Ser Ile Ala Arg Ser Asp Ala Ser Leu Ala Gln
            260                 265                 270

Leu Ser Leu Ile Ser Ser Thr Glu Pro Ile Glu Ala Arg Ala Leu Lys
        275                 280                 285

Ser Gly Thr Pro Thr Lys Thr Tyr Asp Ile Arg Leu Val Asp Pro Leu
    290                 295                 300

Thr Thr Pro Trp Val Ser Lys Ala Tyr Ala Leu Ala Glu Lys Thr Ala
305                 310                 315                 320

Arg Ile Gln Phe Thr Asp Ser Gly Arg Lys Thr Trp Tyr Thr Ala Val
                325                 330                 335
```

-continued

```
Gly Lys Gly Thr Leu Ala Leu His Leu Asp Asp Ile Thr Ser Met Ser
            340                 345                 350

Ile Thr Met Asp Leu Gly Gly Glu Ser Tyr Tyr Tyr Lys Thr Leu Ala
        355                 360                 365

Asn Asp Ala Ala Glu Thr Val Asp Pro Glu Ser Ala Thr Val Ala Phe
    370                 375                 380

Ile Leu Phe Ser Val Thr Arg Pro Leu Glu Glu Ile Thr Thr Ala Ser
385                 390                 395                 400

Glu Leu Gln Thr Gly Lys Ile Val Ala Phe Glu Lys Leu Met Val Ala
                405                 410                 415

Asn Ser Ser Val Gln Gly Ala Lys Ile Ile Ala Asn Thr Ser Leu Lys
            420                 425                 430

Tyr Asn Phe Asp His Asn Ser Ile Ser Gly Asp Lys Ser Glu Leu Asn
        435                 440                 445

His Tyr Leu Leu Cys Gln Leu Leu Phe Asn Asn Leu Ser Ala Ser Thr
    450                 455                 460

Thr Tyr Thr Gln Gln Asp Ala Trp Ala Gly Lys Thr Thr Met Gln Ser
465                 470                 475                 480

Leu Asp Ser Asp Lys Val Thr Val Lys Gly Val Glu Val Asp Arg Val
                485                 490                 495

Ile Pro Ala Gly Ala Phe Gly Asn Tyr Thr Thr Ala Glu Gln Lys Ser
            500                 505                 510

Ser Leu Pro Asn Asp Leu His Ser Val Met Ala Thr His Leu Glu Arg
        515                 520                 525

Ala Ala Lys Ala Met Thr Ala Ile Asp Asp Glu Asp Gln Glu Gly Gly
    530                 535                 540

Ser Thr Val Ala Asn Ala Ile Phe Gly Ala Leu Ile Ser Lys Glu Ser
545                 550                 555                 560

Pro Val Ala Gly Pro Ile Pro Trp Lys Asn Ile Lys Phe Asp Glu Leu
                565                 570                 575

Arg Val Leu Ser Asp Lys Ala Ala Ser Ser Phe Lys Arg Asp Pro Ser
            580                 585                 590

Gln Ala Leu Ile Ser His Asp Pro Val Leu Gly Asp Ser Ala Val Met
        595                 600                 605

Thr Ser Leu Leu Gly Gly Ile Gly Asn Ala Val Lys Thr Lys Gly Leu
    610                 615                 620

Ser Ala Ala Cys Lys Asp Thr Lys Ser Ala Leu Thr Ala Ala Gln Ser
625                 630                 635                 640

Gly Arg Ser Val Arg Gln Thr Ile Leu Asp Lys Ile Glu Lys Leu Phe
                645                 650                 655

Pro Pro Gly Pro Arg Pro Ala Lys Lys Met Ile Glu Glu Gly Pro Ser
            660                 665                 670

Lys Lys Glu Ala Arg Arg Leu Gly Asp Ser Arg Arg Gly Gln Lys
        675                 680                 685


<210> SEQ ID NO 33
<211> LENGTH: 760
<212> TYPE: PRT
<213> ORGANISM: Piscine reovirus

<400> SEQUENCE: 33

Met Pro Ile Ile Asn Leu Pro Ile Glu Pro Thr Asp Gln Ser Ile Thr
1               5                   10                  15

Glu Phe Lys Thr Gln Ala Gln Thr Val Phe Ser Gly Cys Met Glu Asn
            20                  25                  30
```

-continued

```
Thr Asp Val Thr Phe Val Asp Tyr Leu Lys Arg Asp Val Lys Ile Phe
        35                  40                  45

Ile Val Asp Asn Arg Phe Leu Leu Pro Gln Ile Ala Lys Met Ile Asp
    50                  55                  60

Ser Ser Asp Leu Asp Glu Ile Ala Ser Gln Val Leu Asn Leu Pro Leu
65                  70                  75                  80

Leu Ser Glu Ala Cys Phe Ile Leu Leu Pro Pro Leu Ser Val Met Ala
                85                  90                  95

Lys Arg Leu Leu Ser Ser Ser Asp Ser Tyr Pro Asp Ile Phe Leu Thr
            100                 105                 110

Arg Val Pro Thr Arg Val Leu Lys Ala Gln Ser Asp Asn Ser Arg Ser
        115                 120                 125

Thr Ala Leu Leu Lys Phe Met Pro Lys Val Val Thr Ser Ser Thr Thr
    130                 135                 140

Ala Ser Asp Met Leu Thr Met Ser Val Gln Asn Ala Asp Val Tyr Thr
145                 150                 155                 160

Leu Thr Pro Asp Val Ile Gly Met Pro Leu Arg Arg Tyr Ala Glu Lys
                165                 170                 175

Ser His Tyr Pro Ser Ala Phe Asp Phe Gly Ser Ala His Pro Ser Asn
            180                 185                 190

Trp Arg Arg Ser Val Ile Lys Ala Ser Asn Ser Leu Leu Ile Pro Met
        195                 200                 205

Val Pro Val Met Ser Thr Ala Lys Thr Leu Tyr Leu Asp Ala Asp Phe
    210                 215                 220

Ser Thr Ser Asp Asp Arg Thr Gly Ile Phe Trp Arg Leu Ser Ala Ser
225                 230                 235                 240

Ala Arg Ile Arg Ala Arg Gln Arg Gly Val Ile Val Leu Pro Ser Met
                245                 250                 255

Ile Lys Thr Phe Tyr Glu Lys Glu Arg Gly Leu Lys Ser Ala Pro Val
            260                 265                 270

Gln Leu Arg Arg Glu His Lys Met Ala Ala Arg Leu Leu Arg Ile Pro
        275                 280                 285

Phe Gly Arg Val Pro Ser Glu Thr Ser Phe Arg Arg Asp Met Val Gln
    290                 295                 300

Cys Cys Asp Leu Leu Val Ser Thr Ser Val Leu Asn Lys Leu Leu Ser
305                 310                 315                 320

Pro Thr Glu Ala Gly Lys Ser Pro Pro Phe Asp Lys Tyr Val Phe His
                325                 330                 335

Gly Val Pro Val Glu Phe Ile Asn Arg Val Cys Pro Asp Ile Gly Thr
            340                 345                 350

Gln Ala Leu Gly Arg Asp Thr Asn Gly Tyr Leu Gln Glu Trp Leu Ile
        355                 360                 365

Met Leu Phe Leu Met Ser Asp Tyr Ile Thr Ser Thr Thr Ser Arg Arg
    370                 375                 380

Arg Leu Thr Leu Val Thr Asn Phe Asp Pro Met Arg Lys Trp Tyr Asp
385                 390                 395                 400

Ile Thr Leu Leu Lys Ile Thr Asn Thr Tyr Tyr Gln Cys Gln Glu Met
                405                 410                 415

Met Thr Pro Pro Ala Ile Ser Ser Phe Gly Val Cys Ser Gln Lys Gly
            420                 425                 430

Thr Phe Lys Ser Thr Leu Ser Ser Trp Leu Ser Gln Val Ile Val Arg
        435                 440                 445
```

-continued

```
Gly Val Asn Leu Phe Pro Glu Gly Ser Ile Val Asp Ser Asp Asp Leu
    450                 455                 460

Gly Ser Lys Leu Asp Pro Thr Phe Glu Ser Glu Trp Glu Thr Asn Val
465                 470                 475                 480

Ile Glu Lys Ile Gly Met Pro Val Ile Ile Arg Gly Leu Thr Glu Glu
                485                 490                 495

Gly Ala Phe Lys Ile Thr Thr Asp Thr Met Phe Asp Thr Tyr Ala Leu
            500                 505                 510

Phe Arg Gln Leu Tyr Asp Arg Met Ile Val Pro Val Ala Arg His Phe
        515                 520                 525

Phe Asp Tyr Ser Val Ala Ser Gly Arg Lys Met Ile Phe Ala His Cys
    530                 535                 540

Asp Ser Glu Phe Leu Asp Asn Ser Phe Pro Ser Pro Phe Tyr Arg Thr
545                 550                 555                 560

His Ile Thr Ile Asp Asn Tyr Gly Asn Ile Leu Asn Arg Pro Asn Arg
                565                 570                 575

Val Gly Gly Val Leu Ser Gln Tyr Val Leu Ala Glu Cys Tyr Arg Leu
            580                 585                 590

Met Ala Thr Ser Cys Lys Ser Arg Pro Ile Ala Lys Leu Leu Lys Ala
        595                 600                 605

Lys Leu Val Pro Trp Trp Glu Phe Asp Ser His Val Lys Arg Met Gly
    610                 615                 620

Gly Thr Pro Val His Tyr Ser Leu Gly Val Lys Ile Gln Pro Glu Leu
625                 630                 635                 640

Met Arg Asp Ala Gly Tyr Cys Gly His Leu Ile Asp His Ala Arg Val
                645                 650                 655

Glu Val Leu Gln Ala Met Trp Val Pro Glu Ala Val Asp Glu Ser Phe
            660                 665                 670

Phe His Asn Pro Pro Ser Met Pro Leu Thr Ile His Leu Ala Asp Ser
        675                 680                 685

Lys Tyr Asn Arg Tyr Glu Pro Ile Gly Glu His Asn Leu Asn Ile Pro
    690                 695                 700

Val Leu Ile Asp Thr Ser Thr Ser Tyr Leu Ser Glu Thr Tyr Leu Pro
705                 710                 715                 720

Ala Gly Val Val Phe Thr Pro Thr Lys Arg Phe Thr Val Glu Gly Cys
                725                 730                 735

Asp Phe Asn Cys Trp Arg Gly Asn Pro Ile Thr Phe Lys Gly Thr Leu
            740                 745                 750

Ser Trp Trp Ser Thr Ala Gly Glu
        755                 760
```

<210> SEQ ID NO 34
<211> LENGTH: 752
<212> TYPE: PRT
<213> ORGANISM: Piscine reovirus

<400> SEQUENCE: 34

```
Met Ala Glu Ser Ile Thr Phe Gly Gly Pro Ser Arg Lys Leu Asp Leu
1               5                   10                  15

Val Ala Ser Gly Ser Lys Pro Ile Thr Val Thr Val Thr Val Gly Asp
            20                  25                  30

Leu Gly Cys Ser Ile Tyr Gly Thr Val Pro Arg Gly Thr Asp Glu Phe
        35                  40                  45

Val Thr Ser Asp Arg Tyr Leu Ala Met Cys Arg His Leu Leu Val Phe
    50                  55                  60
```

-continued

```
Lys Pro Thr Leu Asn Asn Gly Thr Leu Thr His Tyr Thr Ala Phe Ser
65                  70                  75                  80

Ala Ile Arg Ser Met Ile Ser Pro Leu Gly Phe Gly Val Met Arg Asn
                85                  90                  95

Val Asp Val Val Glu Lys Gln Cys Ala Ile Ile Glu Ala Leu Glu Arg
            100                 105                 110

Arg Gly Met Leu Asn Glu Val Lys Asp Ala Ala Ala Glu Leu Pro Leu
        115                 120                 125

Gln Leu Asp Val Thr Asp Thr Ser Thr His Val Asp Pro Ala Ile Ile
    130                 135                 140

Asp Ser Leu Pro Pro Leu Ile Gln Asn Glu Val Ala Ala Gly Leu Thr
145                 150                 155                 160

Pro Leu Glu Leu Pro Ala Ile Thr Met Val Gln Thr Ala Pro Leu Ile
                165                 170                 175

Thr Pro Ala Leu Gly Met Glu Asn Asp Asp Phe Asn Leu Ser Arg Tyr
            180                 185                 190

Phe Phe Ala Ser Gly Phe Ile Asp Gln Ala Ser Arg Ile Gly Gly Thr
        195                 200                 205

Val Asn Asp Glu Tyr Val Lys Gly Phe Met Gln Ala Leu Pro Arg Phe
    210                 215                 220

Asn Asp Asp Gly Ser Ile Arg Val Asp Cys Asp Val Leu Thr Cys Leu
225                 230                 235                 240

Cys Ser Arg Asp Glu Asp Leu Ser Val Leu Thr Pro Leu Ser Val Asn
                245                 250                 255

Thr Thr Ala Val Ser Asp Met Phe Glu Leu Ser His Asp His Gln Pro
            260                 265                 270

Met Ala Tyr Leu Arg Thr Val Tyr Val Glu Asp Tyr Ile Ala Ser His
        275                 280                 285

Leu Glu Ser Leu Lys Asn Arg Glu Thr Ala Thr Pro Leu Val Leu Lys
    290                 295                 300

Leu Ser Ala Val Asn Ser Val Thr Pro Lys Ala Leu Ile Ala Leu Val
305                 310                 315                 320

Glu Ser Lys Ala Thr Asp Ser Ile Phe Asn Gln Ala Asp Lys Arg Trp
                325                 330                 335

Met Ile Gly Leu Asp Pro Met Phe Ser Glu Cys Trp Pro Gly Ala Ile
            340                 345                 350

Ala Leu Leu Ser Met Leu Phe Asp His Lys Val Asp Tyr Trp Ser Val
        355                 360                 365

Arg Cys Arg Phe Ile Leu Arg Ser Ala Leu Ile Gly Met Ser Asp Asp
    370                 375                 380

Asp Ala Arg Pro Arg Val Gln Met Met Arg Met His Tyr Ser Leu Thr
385                 390                 395                 400

Thr Pro Thr Thr Trp Tyr Ser Thr Arg Gly Val Tyr Ser Ala Glu Gly
                405                 410                 415

Arg Ser Lys Ile His Tyr Ala Ser Gly Asp Arg Met Arg Leu Gly Leu
            420                 425                 430

Arg Val Gly Glu Val Arg Asp Arg Gln Val Thr Met Leu Glu Asp Leu
        435                 440                 445

Ser Thr Ile His Ser Met Asp Val Ala Asn Met Lys Asp Gln Val Ile
    450                 455                 460

Gln Lys Asp Val Gln Leu Lys Ala Leu Thr Glu Ala Met Ser Gln Lys
465                 470                 475                 480
```

```
Asp Ser Leu Ile Asp Ser Leu Arg Ala Asp Val Ala Gly Leu Thr Glu
                485                 490                 495

Arg Ala Val Leu Val Gln Ala Glu His Leu Thr Thr Ile Ala Asp Met
            500                 505                 510

Glu Val Arg Arg Val Gln Ser Glu Asp Lys Ala Arg Ile Gly Ile Asp
        515                 520                 525

Ala Ala Asn Arg Arg Ala Gly Glu Ala Ile Glu Ser Ala His Leu Leu
    530                 535                 540

Thr Glu Glu Phe Ser Lys Cys Leu Ser Ser Asp Phe Leu Met Val Lys
545                 550                 555                 560

Pro Leu Pro Glu His Asn Gln Cys Pro Val Pro Leu Leu Glu Ser Val
                565                 570                 575

Trp Pro Ala Leu Cys Gln Arg Tyr Ile Gln Asn Met Gln Leu Val Asp
            580                 585                 590

Glu Ile Trp Thr Asn Lys Leu Ala Asp Ala Thr Asp Thr Ile Ala Thr
        595                 600                 605

Glu Met Ala Glu Glu Thr Met Arg Ile Ile Ala Glu Arg Asp Cys Gln
    610                 615                 620

Ala Met Val Met Pro Val Val Glu Ala Pro Lys Pro Gln Arg Lys Pro
625                 630                 635                 640

Arg Ile Tyr Glu Pro Ser Asp Asp Asp Leu Glu Arg Thr Ser Val Ser
                645                 650                 655

Ser Thr Ser Ser Glu Lys Lys Lys Arg Val Ile Trp Ser Arg Ser Ala
            660                 665                 670

Thr Arg Val Pro Arg Thr Asp Val Asp Phe Ser Ala Ile Thr Ala Ala
        675                 680                 685

Arg Arg Asp Glu His Phe Glu Leu Gly Met Pro Arg Glu Gly Arg Tyr
    690                 695                 700

Pro Val His Ser Gly Ile Pro Gly Ser Val Arg Ala Thr Met Thr Arg
705                 710                 715                 720

Gly Leu Ala Ile Asp Ser Met Ser Glu Phe Pro Lys Ile Ile Asp Phe
                725                 730                 735

Gly Gly Ser Asp Asp Trp Asp Val Gly Val Asn Asn Val Leu Arg Gly
            740                 745                 750


<210> SEQ ID NO 35
<211> LENGTH: 420
<212> TYPE: PRT
<213> ORGANISM: Piscine reovirus

<400> SEQUENCE: 35

Met Ala Arg Ala Ile Phe Ser Gly Ile Ser Ala Phe Phe Ala Asn Ala
1               5                   10                  15

Pro Tyr Val Gln Asp Gly Asp Thr Ile Lys His Ala Phe Leu Ser Gly
            20                  25                  30

Asp Ser Leu Phe Phe Gln Gly Thr Asn Thr Leu Tyr Pro Thr Leu Ser
        35                  40                  45

Thr Ser Tyr Gln Gly Asp Thr Asp Leu Pro Thr Pro Phe Thr Val Met
    50                  55                  60

Tyr Gln Thr Ala Met Val Arg Ser Ala Leu Phe Gln Val Pro Leu Phe
65                  70                  75                  80

Gly Gly Leu Trp Asn Ala Arg Ser Tyr Arg Asp Leu Val Phe Thr Ser
                85                  90                  95

Gln Ala Met Leu Asn Val Lys Thr Asn Thr Ser Val Thr Cys Pro Pro
            100                 105                 110
```

Pro Val Ile Pro Arg Pro Ala Tyr Val Tyr Asn Val Met Asn Asn Gln
115 120 125

Arg Phe Ala Gln Ser Ala Thr Ala Arg Asn Lys Val Tyr Val Asp Phe
130 135 140

Ser Ile Thr Thr Leu Phe Gln Met Asp Ile Asn Gly Phe Ala Leu Pro
145 150 155 160

Leu Leu Phe Asn Pro Asp Asp Asn Gly Ile Asp Val Thr Leu Ala Leu
165 170 175

Thr Ser Leu Val Gly Gln Ser Trp Ser Thr Ile Val Gly Ala Arg Tyr
180 185 190

Glu Ser Ala Gly Asn Ala Ala Met Asp Ile Asp Asn Pro Ile His Arg
195 200 205

Thr Asn Arg Ala Leu Met Leu Leu Tyr Leu Gly Ser Ala Cys Gly Tyr
210 215 220

Phe Asn Pro Thr Met Thr Trp Asn Gly Phe Tyr Phe Arg Gln Ala Gly
225 230 235 240

Lys Pro Gly Ser Trp Gly Ala Asp Leu Asp Pro Ile Leu Val Arg Gly
245 250 255

Asp Ser Ala Leu Ile Asn Arg Ala Thr Phe Val Arg Leu Asn Arg Trp
260 265 270

Val Val Phe Lys Asp Phe Leu Trp Gln Met Ser Arg Gly Thr Leu His
275 280 285

Ala Leu Val Leu Gly Gly Met Ile Cys Ala Val Glu Gln Pro Leu Arg
290 295 300

Gly Leu Ser Val Ile Ser Val Leu Ala Asn Thr Val Cys Ala Pro Trp
305 310 315 320

Thr Gly Val Asn Gly Arg Ala Gly Asp Glu Val Thr Thr Ile Gly Leu
325 330 335

Lys Tyr Val Ala Ile Glu Asn Leu Ile Arg Ser Gly Ser Tyr Thr Val
340 345 350

Ala Glu Gly Val Val Ala Asp Ala Gln Ile Ala Ala Trp Gly Val Arg
355 360 365

Asn Thr Asp His Met Asp Arg Val Arg Ala Ala Asp Asp Ala Asn Val
370 375 380

Leu Ala Gly Val Asn Ile Arg Arg Val Lys Pro Trp Asp Asn Gly Gly
385 390 395 400

Gly Phe Gln Arg Leu Ala Ala Val Arg Ala Leu Val Asn Leu Met Ala
405 410 415

Ala Asn Thr Arg
420

<210> SEQ ID NO 36
<211> LENGTH: 71
<212> TYPE: PRT
<213> ORGANISM: Piscine reovirus

<400> SEQUENCE: 36

Met Ala Thr Gln Leu Ser Met His Ser Phe Leu Ala Thr His Ser Phe
1 5 10 15

Ser Lys Gly Pro Thr His Cys Thr Pro His Phe Pro Gln Val Ile Lys
20 25 30

Glu Ile Leu Thr Ser Gln Pro His Leu Leu Leu Cys Ile Arg Leu Leu
35 40 45

Trp Ser Gly Leu Arg Tyr Phe Arg Tyr His Ser Ser Ala Asp Phe Gly

```
    50                  55                  60

Thr Gln Glu Ala Ile Gly Ile
65                  70


<210> SEQ ID NO 37
<211> LENGTH: 354
<212> TYPE: PRT
<213> ORGANISM: Piscine reovirus

<400> SEQUENCE: 37

Met Ser Asn Phe Asp Leu Gly Arg Gln Ala Asn Lys Pro Lys Thr Glu
1               5                   10                  15

Tyr His Leu Asn Ala Leu Pro Tyr Leu Lys Cys Gly Ile Lys Asn Ser
            20                  25                  30

Glu Ser Val Gly Ser Val Ile Ile Asn Phe Pro Ala Arg Phe Asp Thr
        35                  40                  45

Ala Lys Ser Val Ser Pro Leu Ser Ala Met Thr Asn Asp Gly Phe Leu
    50                  55                  60

Lys Phe Lys Asp Pro Ser Asp Ser Leu Ala Ser Arg Asp Arg Pro Ala
65                  70                  75                  80

Phe Asn Asp Tyr Val Arg Ala Leu Gln Pro Ser Pro Glu His Pro His
                85                  90                  95

His Phe Gln Ala Leu Asp Pro Ala Phe Thr Asp Glu Ile Leu Lys Thr
            100                 105                 110

Cys Asp Pro Thr Phe Asn Trp Thr Ser Ile Lys Ser Gly Asp Lys Tyr
        115                 120                 125

Tyr Leu Pro Ala Ile Ser Gln Ala Leu Val Tyr Arg Ala Ser Gly Phe
    130                 135                 140

Arg Phe Asn Ser Glu Lys His Leu Glu Gln Thr Gly Ser Leu Leu Pro
145                 150                 155                 160

Ile Ala Leu Gly Ile Ser Lys Ala Thr Cys Ala Leu Pro Val Leu Val
                165                 170                 175

Asp Ser Gly Thr Val Val Cys Pro Glu Glu Asn Val Ser Ala Leu Phe
            180                 185                 190

Ser Lys Asp Lys Leu Ser Ser Leu Asp Ile Gln Phe Gly Tyr Pro Lys
        195                 200                 205

Pro Lys Asn Gly Asn Asp Ser Thr Ala Tyr Thr Lys Ser Ile Asn Gly
    210                 215                 220

Tyr Gln Ile Gly Ala Tyr Gly Leu Lys Leu Pro Gly Gly His Phe Leu
225                 230                 235                 240

Lys Leu Ile His Ile Leu Asn Cys Met Cys Leu Lys Ala Asp Leu Asp
                245                 250                 255

Leu Leu Ser Gln Val Pro Ser Leu Ala Asp Ser Leu Asn Arg Gly Met
            260                 265                 270

Arg Cys Gly Tyr Ala Leu Leu Gln Tyr Val Ser Gln Phe Ala Thr Val
        275                 280                 285

Asp Arg Glu Leu Leu Leu Met Ser Phe Leu Leu Lys Glu Ala Asn Asp
    290                 295                 300

Pro Thr Phe His Glu Val Ala Ala Met Trp Lys Ser Val Arg Asp Gly
305                 310                 315                 320

Thr Ala Gln Met Asp Asp Val Arg Phe Asp Leu Gln Pro Phe Gly Ile
                325                 330                 335

Met Ala Ser Thr Ala Ser Leu Arg Asp Gly Val Arg Ile Met Ala Met
            340                 345                 350
```

Phe Cys

<210> SEQ ID NO 38
<211> LENGTH: 315
<212> TYPE: PRT
<213> ORGANISM: Piscine reovirus

<400> SEQUENCE: 38

```
Met His Arg Phe Thr Gln Glu Asp His Val Ile Ile Asn Ser Arg Leu
1               5                   10                  15

Asp Ala Ile Glu Glu Asp Asn Lys Arg Asn Phe Ala Ser Leu Lys Gln
            20                  25                  30

Ser Ile His Asn Asn Tyr Gly Leu Leu Arg Ser Leu Leu Gly Gly Gln
        35                  40                  45

Gly Arg Leu Asn Gly Lys Ile Gly Asp Leu Glu Lys Asp Val Asn Leu
    50                  55                  60

Ile His Leu Arg Val Val Ser Leu Glu His Ala Leu Asp Asp Leu Arg
65                  70                  75                  80

Ala Asp Phe Asp Ala Phe Thr Pro Thr Val Gly Pro Glu Ile Asp Asp
                85                  90                  95

Lys Leu Ala Pro Leu Gln Lys Gln Leu Lys Val Leu Asn Asp Gln Leu
            100                 105                 110

Thr Ile Met Asn Ser Glu Val Ala Val Leu Gly Lys Gly Ile Phe Gly
        115                 120                 125

Asp Tyr Gln Leu Thr Asp Leu Leu Gly His Thr Val Gly Gly Val Ala
    130                 135                 140

Ala Val Thr Thr Asn Ser Leu Thr Ser Ala Phe Arg Leu Ser Asp Arg
145                 150                 155                 160

Leu Pro Ala Thr Thr Val Gly Asp Phe Ser Leu Ser Thr Gly Val Gly
                165                 170                 175

Tyr Thr Phe Val Gly Thr Ala Pro Arg Pro Ile Leu Gln Val Glu Asp
            180                 185                 190

Phe Met Arg Gly Thr Cys Arg Met Asn Leu Thr Asp Thr Ala Leu Met
        195                 200                 205

Tyr Gly Gly Ser His Ile Pro Leu Leu Gln Gln Ser Leu Leu Gln Leu
    210                 215                 220

Glu Thr Thr Val Pro Pro Gly Pro Thr Asp Trp Lys Lys Leu Pro Gln
225                 230                 235                 240

Met Val Lys Gly Val Leu Trp Met Ser Leu Val Asp Tyr Glu Gly Ala
                245                 250                 255

Asn Val Val Pro Val Val Val Met Arg Lys Val Asn Ala Thr Val Thr
            260                 265                 270

Thr Val Ile Leu Pro Asp Met Val Gly Lys Gln Lys Leu Ile Ser Ser
        275                 280                 285

Phe Pro Trp Thr Thr Arg Ser Thr Phe Met Ser Pro Gly Met Glu Val
    290                 295                 300

Ile Ile His Gly Gly Asp Phe Val Ile Ile Ile
305                 310                 315
```

<210> SEQ ID NO 39
<211> LENGTH: 330
<212> TYPE: PRT
<213> ORGANISM: Piscine reovirus

<400> SEQUENCE: 39

```
Met Ala Asn His Arg Thr Ala Thr Thr Thr Asp Phe Ser Asp Phe Ile
```

-continued

```
1               5                   10                  15

Glu Ser Thr Leu His Gly Asn Ile Ile Phe Tyr Asp Asp Gln His Asn
            20                  25                  30

Thr Ser Ser Glu Trp Ile Pro Gly Thr Ser Lys Phe Val Arg Val Gly
        35                  40                  45

Ser Leu Arg Ile Cys Val Glu Cys Gly His Arg Val Gly Leu Ser His
    50                  55                  60

Asn Ala Lys Pro Val Met Val Thr His Gln Cys Asp Gly Asp Thr Leu
65                  70                  75                  80

Trp Asp His Ser Thr Pro Gly Asp Trp Thr Trp Ser Glu Trp Ser Tyr
                85                  90                  95

Phe Val Thr Ser Cys Ala Asn Ala Leu Ser Ala Asn Ala Asp Ala Tyr
            100                 105                 110

Leu Arg Ile Leu Asn Asp Lys Trp Thr Glu Asp Asn Ser Arg Gly Ser
        115                 120                 125

Asn Asp Arg Pro Asp Arg Arg Gly Val Ile Glu Ala Lys Arg Arg Leu
    130                 135                 140

Arg Asp Asp Met Arg Gly Ile Met Lys Lys Lys Thr Ala Gly Asp Leu
145                 150                 155                 160

Gly Leu Thr Gly Trp Leu Ile Leu Asp Pro Asp Glu Leu Glu Ser Phe
                165                 170                 175

Pro Asp Tyr Ser Thr Glu Met Thr Gln Leu Gln Glu Asp Met Glu Glu
            180                 185                 190

Leu Asn Pro Val Glu Gln Lys Thr Gly Asn Gly Gly Lys Ala His Val
        195                 200                 205

Ala Ala Ala Asn Gln Phe Pro His Lys Val Ile Leu Arg Pro Ala Tyr
    210                 215                 220

Gly Thr Val Pro Ile Val Met Tyr Leu Asp Thr Arg Glu Asp His Asn
225                 230                 235                 240

Ala Tyr Leu Cys Leu Ser Leu Lys Thr Lys Ala His Met Val Asn Met
                245                 250                 255

Ile Arg Arg Met Cys Tyr Ser Gly Met Pro Ala Asn Ile Ile Lys Met
            260                 265                 270

Thr Gln Gly Met Ala Leu Ser Gly Met Glu Glu Met Thr Phe Arg Ser
        275                 280                 285

Gly His Arg Leu Phe Gly His Met His Ser Gly His Thr Ile Pro Val
    290                 295                 300

Lys Gly Thr Ser Ser Leu Thr Leu Thr Ser Gly Lys Cys Ser His Thr
305                 310                 315                 320

Cys Gln Asn Leu Leu Lys Trp Ser Ser Ala
                325                 330
```

<210> SEQ ID NO 40
<211> LENGTH: 124
<212> TYPE: PRT
<213> ORGANISM: Piscine reovirus

<400> SEQUENCE: 40

```
Met Thr Thr Asn Ile Thr Leu Gln Ala Ser Gly Ser Leu Val Pro Ala
1               5                   10                  15

Ser Leu Leu Gly Ser Val Pro Phe Glu Tyr Val Leu Asn Ala Gly Ile
            20                  25                  30

Gly Leu Val Cys Leu Ile Met Leu Ser Leu Leu Trp Ser Leu Ile Asn
        35                  40                  45
```

-continued

```
Ala Thr Ala Ile Arg Cys Gly Ile Ile Leu His Pro Glu Ile Gly His
    50                  55                  60

Gly Val Asn Gly Ala Ile Ser Ser Leu Val Ala Gln Met Pro Phe Leu
65                  70                  75                  80

Arg Thr Gln Thr Leu Thr Ser Glu Ser Ser Met Thr Asn Gly Gln Lys
                85                  90                  95

Thr Thr Val Ala Val Gln Thr Thr Asp Gln Thr Asp Ala Glu Ser Leu
            100                 105                 110

Lys Leu Ser Asp Ala Leu Glu Thr Ile Cys Val Ala
        115                 120


<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41

catactccaa gatcatcgcc agca                                            24


<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 42

His His His His His His
1               5


<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

cccttaaggg c                                                          11


<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

gcccttggtg aaggg                                                      15
```

PISCINE REOVIRUS DIAGNOSTIC COMPOSITIONS

This application claims the benefit of and priority to, U.S. provisional patent application Ser. No. 61/325,047 filed Apr. 16, 2010, and U.S. provisional patent application Ser. No. 61/380,594 filed Sep. 7, 2010, the disclosures of all of which are hereby incorporated by reference in their entireties for all purposes.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All publications, patent applications, patents, and other references mentioned herein are incorporated by reference in their entirety. The patent and scientific literature referred to herein establishes knowledge that is available to those skilled in the art. The issued patents, applications, and other publications that are cited herein are hereby incorporated by reference to the same extent as if each was specifically and individually indicated to be incorporated by reference. In the case of inconsistencies, the present disclosure will prevail.

BACKGROUND

Fish are an increasingly important source of food and income; global annual consumption projected to rise from 110 million tons in 2010 to more than 200 million tons in 2030. Whereas rates of wild fish capture are flat or declining due to overfishing and loss of habitat, the global mariculture harvest is growing at a rate in excess of 8% per annum. However, the emergence of infectious diseases in aquaculture threatens production and may also impact wild fish populations. Atlantic salmon (*Salmo salar* L.) are amongst the most popular of farmed fish, accounting for annual production of more than 1 million tons. Atlantic salmon mariculture has been associated with epidemics of infectious diseases that threaten not only local production, but also wild fish coming into close proximity to marine pens, or fish escaping from them. Heart and skeletal muscle inflammation (HSMI) is a frequently fatal disease of farmed Atlantic salmon. First recognized in one farm in Norway in 1999 (Kongtorp et al., J Fish Dis 27, 351-358 (2004)), HSMI was subsequently implicated in outbreaks in other farms in Norway and the United Kingdom (Ferguson et al., J Fish Dis 28, 119-123 (2005)). Although pathology and disease transmission studies indicated an infectious basis, efforts to identify an agent were unsuccessful.

HSMI is transmissible but the causal agent has not been previously isolated. HSMI is an important disease that threatens aquaculture. Identification of the causative agent of this disease can enable diagnosis of infection, containment of infection and development of vaccines to prevent disease.

There is a need for a diagnostic test, a vaccine or and a method of treating animals having HSMI. This invention addresses these needs.

SUMMARY OF THE INVENTION

The invention relates to Piscine reovirus (PRV), a novel orthoreovirus-like virus associated with Salmon HSMI, and isolated nucleic acids sequences and peptides thereof. The invention is also related to antibodies against antigens derived from PRV and method for generating such antibodies. The invention is also related to immunogenic compositions for inducing an immune response against PRV in an animal.

In one aspect, the invention provides an isolated nucleic acid having a sequence selected from the group consisting of: SEQ ID NOs: 1-10.

In another aspect, the invention provides an isolated nucleic acid comprising 10 consecutive nucleotides having a sequence selected from the group consisting of: SEQ ID NOs: 1-10.

In still a further aspect, the invention provides an isolated nucleic acid which is a variant of any one of SEQ ID NOs: 1-10 and has at least about 85% identity to SEQ ID NO: 1-10. In one embodiment, the variant has at least about 90%, about 95.5%, about 96%, about 96.5%, about 97%, about 97.5%, about 98%, about 98.5%, about 99%, about 99.5% or about 99.9% identity to that of any one of SEQ ID NO: 1-10. In one embodiment, the identity is determined by analysis with a sequence comparison algorithm. In one embodiment, the sequence comparison algorithm is FASTA version 3.0t78 using default parameters.

In another aspect, the invention provides an isolated nucleic acid complementary to a sequence selected from the group consisting of: SEQ ID NOs: 1-10.

In still another aspect, the invention provides an isolated nucleic acid comprising 10 consecutive nucleotides complementary to a sequence selected from the group consisting of: SEQ ID NOs: 1-10

In still a further aspect, the invention provides an isolated nucleic acid which is a complementary to a variant of any one of SEQ ID NOs: 1-10 and wherein the variant has at least about 85% identity to SEQ ID NO: 1-10. In one embodiment, the variant has at least about 90%, about 95.5%, about 96%, about 96.5%, about 97%, about 97.5%, about 98%, about 98.5%, about 99%, about 99.5% or about 99.9% identity to that of any one of SEQ ID NO: 1-10. In one embodiment, the identity is determined by analysis with a sequence comparison algorithm. In one embodiment, the sequence comparison algorithm is FASTA version 3.0t78 using default parameters.

In yet another aspect, the invention provides an isolated polypeptide having a sequence selected from the group consisting of: SEQ ID NOs: 29-40.

In still a further aspect, the invention provides an isolated polypeptide comprising 8 consecutive amino acids having a sequence selected from the group consisting of: SEQ ID NOs: 29-40.

In yet another aspect, the invention provides an isolated polypeptide which is a variant of any one of SEQ ID NOs: 29-40 and has at least about 85% identity to SEQ ID NO: 29-40. In one embodiment, the variant has at least about 90%, about 95.5%, about 96%, about 96.5%, about 97%, about 97.5%, about 98%, about 98.5%, about 99%, about 99.5% or about 99.9% identity to that of any one of SEQ ID NO: 29-40. In another embodiment, the identity is determined by analysis with a sequence comparison algorithm. In still a further embodiment, the sequence comparison algorithm is FASTA version 3.0t78 using default parameters.

In yet another aspect, the invention provides an isolated diagnostic antibody that specifically binds to a polypeptide encoded by the nucleotide sequence shown in any one of SEQ ID NO: 1-10.

In still another aspect, the invention provides an isolated diagnostic antibody that specifically binds to a polypeptide having the sequence of any of SEQ ID NO: 29-40. In one embodiment, the diagnostic antibody is a polyclonal antibody. In another embodiment, the diagnostic antibody is a monoclonal antibody.

In yet another aspect, the invention provides an oligonucleotide probe comprising from about 10 nucleotides to about 50 nucleotides, wherein at least about 10 contiguous nucleotides are at least 95% complementary to a nucleic acid target region within a nucleic acid sequence selected from the group consisting of: SEQ ID NO: 1-10. In one embodiment, the probe is at least about 95.5%, about 96%, about 96.5%, about 97%, about 97.5%, about 98%, about 98.5%, about 99%, about 99.5% or about 99.9% complementary to SEQ ID NO: 1-10. In still a further embodiment, the oligonucleotide probe consists essentially of from about 10 to about 50 nucleotides.

In another aspect, the invention provides a synthetic nucleic acid which has a sequence consisting of from about 10 to about 30 consecutive nucleotides from a nucleic acid sequence selected from the group consisting of: SEQ ID NOS: 1-10.

In still a further aspect, the invention provides a method for determining the presence or absence of PRV in a biological sample, the method comprising: a) contacting nucleic acid from a biological sample with at least one primer which is a synthetic nucleic acid which has a sequence consisting of from about 10 to about 30 consecutive nucleotides from a nucleic acid sequence selected from the group consisting of: SEQ ID NOS: 1-10, b) subjecting the nucleic acid and the primer to amplification conditions, and c) determining the presence or absence of amplification product, wherein the presence of amplification product indicates the presence of RNA associated with PRV in the sample.

In still a further aspect, the invention provides a synthetic nucleic acid which has a sequence consisting of from about 10 to about 30 consecutive nucleotides from a nucleic acid sequence which is complementary to a nucleic acid sequence selected from the group of sequences consisting of SEQ ID NO: 1-10.

In still a further aspect, the invention provides a method for determining the presence or absence of PRV in a biological sample, the method comprising: a) contacting nucleic acid from a biological sample with at least one primer which is a synthetic nucleic acid which has a sequence consisting of from about 10 to about 30 consecutive nucleotides from a nucleic acid sequence selected from the group consisting of: SEQ ID NOS: 1-10, b) subjecting the nucleic acid and the primer to amplification conditions, and c) determining the presence or absence of amplification product, wherein the presence of amplification product indicates the presence of RNA associated with PRV in the sample.

In still a further aspect, the invention provides a primer set for determining the presence or absence of PRV in a biological sample, wherein the primer set comprises at least one synthetic nucleic acid sequence selected from the group consisting of: a) a synthetic nucleic acid which has a sequence consisting of from about 10 to about 30 consecutive nucleotides from a nucleic acids sequence selected from the group of sequences consisting of SEQ ID NO: 1-10, and b) a synthetic nucleic acid which has a sequence consisting of from about 10 to about 30 consecutive nucleotides from a nucleic acids sequence which is complementary to a nucleic acid sequence selected from the group of sequences consisting of SEQ ID NO: 1-10.

In still another aspect, the invention provides a method for determining whether or not a sample contains PRV, the method comprising: a) contacting a biological sample with an antibody that specifically binds a polypeptide encoded by the nucleic sequence acid of any one of SEQ ID NO: 1-10, and b) determining whether or not the antibody binds to an antigen in the biological sample, wherein binding indicates that the biological sample contains PRV. In one embodiment, the determining comprises use of a lateral flow assay or ELISA.

In still another aspect, the invention provides a method for determining whether or not a biological sample has been infected by PRV, the method comprising: a) determining whether or not a biological sample contains antibody that specifically binds a polypeptide encoded by the nucleic sequence acid of any one of SEQ ID NO: 1-10.

In a further aspect, the invention provides an interfering RNA (iRNA) comprising a sense strand having at least 15 contiguous nucleotides complementary to the anti-sense strand of a gene from a virus comprising a nucleic acid sequence selected from the group of sequences consisting of SEQ ID NO: 1-10.

In another aspect, the invention provides an interfering RNA (iRNA) comprising an anti-sense strand having at least 15 contiguous nucleotides complementary to the sense strand of gene from a virus comprising a nucleic acid sequence selected from the group of sequences consisting of SEQ ID NO: 1-10.

In still another aspect, the invention provides a method for reducing the levels of a viral protein, viral mRNA or viral titer in a cell in an animal comprising: administering an iRNA agent to an animal, wherein the iRNA agent comprises a sense strand having at least 15 contiguous nucleotides complementary to gene from a PRV comprising a nucleic acid sequence selected from the group of sequences consisting of SEQ ID NO: 1-10 and an antisense strand having at least 15 contiguous nucleotides complementary to the sense strand. In one embodiment, the method further comprises co-administering a second iRNA agent to the animal, wherein the second iRNA agent comprises a sense strand having at least 15 or more contiguous nucleotides complementary to second gene from the PRV comprising a nucleic acid sequence selected from the group of sequences consisting of SEQ ID NO: 1-10 and an antisense strand having at least 15 or more contiguous nucleotides complementary to the sense strand.

In another aspect, the invention provides a method of reducing the levels of a viral protein from at least one gene of a PRV in a cell in an animal, the method comprising administering an iRNA agent to an animal, wherein the iRNA agent comprises a sense strand having at least 15 or more contiguous nucleotides selected from the group of sequences consisting of SEQ ID NO: 1-10 complementary to a gene from a PRV and an antisense strand having at least 15 or more contiguous nucleotides complementary to the sense strand of a nucleic acid sequence selected from the group of sequences consisting of SEQ ID NO: 1-10.

In one embodiment, the sample used in conjunction with any of the methods described herein is from a teleost.

In one embodiment, the sample used in conjunction with any of the methods described herein is from a salmon.

In yet another aspect, the invention provides an isolated virus comprising any one of the nucleic acid sequences of SEQ ID NOS: 1-10.

In still another aspect, the invention provides an isolated virus comprising a polypeptide encoded by the nucleic sequence acid of any one of SEQ ID NO: 1-10.

BRIEF DESCRIPTION OF THE FIGURES

FIG. 3. Graphical representation of group differences in the log ratio of virus load normalized to a salmon host gene. Nonparametric approaches were used to determine statistical significance for comparisons of the relative viral load among healthy and HSMI-affected farmed fish. Log transformations, which did not normalize log ratio distributions, were nonetheless performed for all samples after calculating L1 (virus)/EF1A (housekeeping) ratios to aid in graphical representation.

FIG. 4. In situ hybridization was performed using locked nucleic acid (LNA) probes targeting the L2 segment of the Piscine reovirus. Sections were permeabilized using proteinase K followed by hybridization with digoxigenin (DIG)-labeled LNA probes. Sections were incubated with a mouse monoclonal anti-DIG-horse radish peroxidase and stained using a Tyramide Signal Amplification System. Sections were counterstained with Meyer's hematoxylin solution.

FIG. 18. A schematic illustration for a method for generating antibodies against σ1, σ3 and μ1C.

FIG. 19. Peptide antigen.

DETAILED DESCRIPTION

Figure 1:
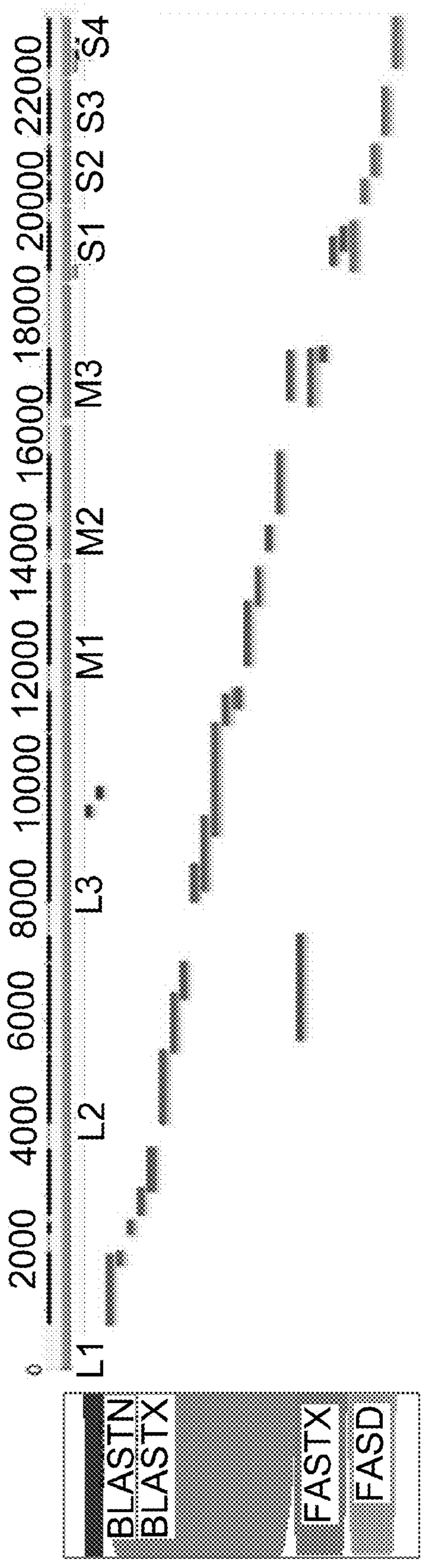
FIG. 1. Piscine reovirus (PRV) sequence obtained by pyrosequencing. Assembled sequence data mapped against the concatenated sequences of PRV. Genomic regions identified by BLASTN, BLASTX, FASTX, and FASD are shown in red, blue, green, and orange respectively.

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, "PRV" refers to isolates of the Piscine reoviruses described herein.

As used herein, the term "animal" refers to a vertebrate, including, but not limited to a teleost (e.g. salmon).

As used herein, the term "PRV polypeptide" includes a PRV polypeptide, a PRV polypeptide fragment or a PRV polypeptide variant, or a polypeptide substantially identical to a PRV polypeptide.

As used herein, the term "antibody" refers to a diagnostic antibody that binds to a PRV polypeptide, a PRV polypeptide fragment or a PRV polypeptide variant, or a polypeptide substantially identical to a PRV polypeptide and does not inhibit, neutralize or reduce the activity or function of a PRV polypeptide or a PRV. The term antibody specifically excludes antibodies which bind a PRV polypeptide, a PRV polypeptide fragment or a PRV polypeptide variant, or a polypeptide substantially identical to a PRV polypeptide and which inhibit, neutralize or reduce the activity or function of the polypeptide or the PRV.

Mariculture, aquaculture in marine environments, is an increasingly important source of dietary protein for human consumption. HSMI appears 5 to 9 months after fish are transferred from fresh water to ocean pens (Kongtorp et al., J Fish Dis 27, 351-358 (2004)), but outbreaks have been recorded as early as 14 days following seawater transfer. Affected fish are anorexic and display abnormal swimming behavior. Autopsy findings typically include a pale heart, yellow liver, ascites, swollen spleen and petechiae in the perivisceral fat. The pathology is further characterized by epi-, endo- and myocarditis, myocardial necrosis, myositis and necrosis of red skeletal muscle, and up to 20% mortality (Kongtorp et al., Dis Aquat Organ 59, 217-224 (2004)). While mortality is variable (up to 20%), morbidity may be very high in affected cages. HSMI is diagnosed on the basis of histopathology. The major pathological changes occur in the myocardium and red skeletal muscle, where extensive inflammation and multifocal necrosis of myocytes are evident.

Disease can be induced in naïve fish by experimental injection with tissue homogenate from HSMI diseased fish or by cohabitation with fish with HSMI (Kongtorp et al., J Fish Dis 27, 351-358 (2004)). Virus-like particles have been observed (Watanabe, K. et al., Dis Aquat Organ 70, 183-192 (2006)); however, efforts to implicate an infectious agent by using culture, subtractive cloning and consensus polymerase chain reaction have been unsuccessful.

In one aspect, the present invention shows that HSMI is associated with infection with a novel reovirus termed Piscine reovirus (PRV). PRV was identified through high-throughput pyrosequencing of serum and heart tissue of experimentally infected fish using novel frequency analysis methods as well as standard alignment methods. In another aspect, the present invention provides PRV nucleic acid sequences.

In other aspects, the invention is directed to expression constructs, for example plasmids and vectors, and isolated nucleic acids which comprise PRV nucleic acid sequences of SEQ ID NOs: 1-10, fragments, complementary sequences, and/or variants thereof.

The nucleic acid sequences and polypeptides described herein may be useful for multiple applications, including, but not limited to, generation of diagnostic antibodies and diagnostic nucleic acids.

In another aspect, the invention is directed to a polypeptide comprising the amino acid sequence of any one of SEQ ID NOs: 29-40.

In one aspect, the invention provides an isolated PRV nucleic acid having the sequence of any of SEQ ID NOs: 1-10, or a fragment thereof.

In another aspect, the invention provides an isolated PRV nucleic acid which comprises consecutive nucleotides having a sequence selected from the group consisting of any of SEQ ID NOs: 1-10, or a fragment thereof.

In another aspect, the invention provides an isolated PRV nucleic acid which comprises consecutive nucleotides having a sequence selected from a variant of any of SEQ ID NOs: 1-10 or a fragment thereof. In one embodiment, the variant has at least about 85% identity to SEQ ID NOs: 1-10, or a fragment thereof. In one embodiment of the above aspect of the invention, the variant has at least about 90%, about 95.5%, about 96%, about 96.5%, about 97%, about 97.5%, about 98%, about 98.5%, about 99%, about 99.5% or about 99.9% identity to that of any one of SEQ ID NOs: 1-10, or a fragment thereof.

In one aspect, the invention provides an isolated PRV nucleic acid complementary to a PRV nucleic acid sequence in any of SEQ ID NOs: 1-10, or a fragment thereof.

In another aspect, the invention provides an isolated PRV nucleic acid which comprises consecutive nucleotides complementary to a PRV nucleic acid sequence in any of SEQ ID NOs: 1-10, or a fragment thereof.

In another aspect, the invention provides an isolated PRV nucleic acid which comprises consecutive nucleotides complementary to a PRV nucleic acid sequence in any of SEQ ID NOs: 1-10, or a fragment thereof. In one embodiment, the variant has at least about 85% identity to SEQ ID NOs: 1-10, or a fragment thereof. In one embodiment of the above aspect of the invention, the variant has at least about 90%, about 95.5%, about 96%, about 96.5%, about 97%, about 97.5%, about 98%, about 98.5%, about 99%, about 99.5% or about 99.9% identity to that of any one of SEQ ID NOs: 1-10, or a fragment thereof.

In another aspect, the invention provides an isolated PRV nucleic acid having a sequence substantially identical to a PRV nucleic acid sequence in any of SEQ ID NOs: 1-10, or a fragment thereof.

In another aspect, the invention provides an isolated PRV nucleic acid having a sequence substantially identical to a sequence complementary to a PRV nucleic acid sequence in any of SEQ ID NOs: 1-10, or a fragment thereof.

In another aspect, the invention provides an oligonucleotide probe which comprises from about 10 nucleotides to about 50 nucleotides, wherein at least about 10 contiguous nucleotides are at least 95% complementary to a nucleic acid target region within a PRV nucleic acid sequence in any of SEQ ID NOs: 1-10, wherein the oligonucleotide probe hybridizes to the nucleic acid target region under moderate to highly stringent conditions to form a detectable nucleic acid target:oligonucleotide probe duplex. In one embodiment, the oligonucleotide probe is at least about 95.5%, about 96%, about 96.5%, about 97%, about 97.5%, about 98%, about 98.5%, about 99%, about 99.5% or about 99.9% complementary to SEQ ID NOs: 1-10. In another embodiment the oligonucleotide probe consists essentially of from about 10 to about 50 nucleotides.

Polynucleotides homologous to the sequences illustrated in the SEQ ID NOs 1-10 can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations.

In certain aspects, the invention is directed to primer sets comprising isolated nucleic acids as described herein, which primer set are suitable for amplification of nucleic acids from samples which comprises Piscine reoviruses represented by any one of SEQ ID NO: 1-10, or variants thereof. Primer sets can comprise any suitable combination of primers which would allow amplification of a target nucleic acid sequences in a sample which comprises Piscine reoviruses represented by any one of SEQ ID NO: 1-10, or variants thereof. Amplification can be performed by any suitable method known in the art, for example but not limited to PCR, RT-PCR, transcription mediated amplification (TMA).

Hybridization conditions: As used herein, the phrase "stringent hybridization conditions" refers to conditions under which a probe, primer or oligonucleotide will hybridize to its target sequence, and can hybridize, for example but not limited to, variants of the disclosed polynucleotide sequences, including allelic or splice variants, or sequences that encode orthologs or paralogs of presently disclosed polypeptides. The precise conditions for stringent hybridization are typically sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Nucleic acid hybridization methods are disclosed in detail by Kashima et al. (1985) Nature 313:402-404, and Sambrook et al. (1989) Molecular Cloning: A Laboratory Manual, 2nd Ed., Cold Spring Harbor Laboratory, Cold Spring Harbor, N.Y ("Sambrook"); and by Haymes et al., "Nucleic Acid Hybridization: A Practical Approach", IRL Press, Washington, D.C. (1985), which references are incorporated herein by reference.

In general, stringency is determined by the temperature, ionic strength, and concentration of denaturing agents (e.g., formamide) used in a hybridization and washing procedure. The degree to which two nucleic acids hybridize under various conditions of stringency is correlated with the extent of their similarity. Numerous variations are possible in the conditions and means by which nucleic acid hybridization can be performed to isolate nucleic sequences having similarity to the nucleic acid sequences known in the art and are not limited to those explicitly disclosed herein. Such an approach may be used to isolate polynucleotide sequences having various degrees of similarity with disclosed nucleic acid sequences, such as, for example, nucleic acid sequences having 60% identity, or about 70% identity, or about 80% or greater identity with disclosed nucleic acid sequences.

Stringent conditions are known to those skilled in the art and can be found in Current Protocols In Molecular Biology, John Wiley & Sons, N.Y. (1989), 6.3.1-10.3.6. In certain embodiments, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6× sodium chloride/sodium citrate (SSC), 50 mM Tris-HCl (pH 7.5), 1 nM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. Another non-limiting example of stringent hybridization conditions are hybridization in 6× sodium chloride/sodium citrate (SSC) at about 45° C., followed by one or more washes in 0.2× SSC, 0.1% SDS at 50-65° C. Examples of moderate to low stringency hybridization conditions are well known in the art.

Stability of DNA duplexes is affected by such factors as base composition, length, and degree of base pair mismatch. Hybridization conditions may be adjusted to allow DNAs of different sequence relatedness to hybridize. The melting temperature (Tm) is defined as the temperature when 50% of the duplex molecules have dissociated into their constituent single strands. The melting temperature of a perfectly matched duplex, where the hybridization buffer contains formamide as a denaturing agent, may be estimated by the following equation: DNA-DNA: Tm(° C.)=81.5+16.6(log [Na+])+0.41(% G+C)−0.62(% formamide)−500/L (1) DNA-RNA: Tm(° C.)=79.8+18.5(log [Na+])+0.58(% G+C)+0.12(% G+C)$^2$−0.5(% formamide)−820/L (2) RNA-RNA: Tm(C)=79.8+18.5(log [Na+])+0.58(% G+C)+0.12(% G+C)$^2$−0.35(% formamide)−820/L (3), where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson et al. (1985) supra). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments. The stringency can be adjusted either during the hybridization step or in the post-hybridization washes. Salt concentration, formamide concentration, hybridization temperature and probe lengths are variables that can be used to alter stringency. As a general guidelines high stringency is typically performed at Tm-5° C. to Tm-20° C., moderate stringency at Tm-20° C. to Tm-35° C. and low stringency at Tm-35° SC to Tm-50° C. for duplex>150 base pairs. Hybridization may be performed at low to moderate stringency (25-50° C. below Tm), followed by post-hybridization washes at increasing stringencies. Maximum rates of hybridization in solution are determined empirically to occur at Tm-25° C. for DNA-DNA duplex and Tm-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point (Tm) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. In certain embodiments, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas in certain embodiments high stringency hybridization may be obtained in the presence of at least about 35% formamide, and in other embodiments in the presence of at least about 50% formamide. In certain embodiments, stringent temperature conditions will ordinarily include temperatures of at least about 30° C., and in other embodiment at least about 37° C., and in other embodiments at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed. In a certain embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide. In another embodiment, hybridization will occur at 42 C in 250 mM NaCl, 25 mM trisodium citrate, 1% SDS, 50% formamide. Useful variations on these conditions will be readily apparent to those skilled in the art.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps can be less than about 30 mM NaCl and 3 mM trisodium citrate, and in certain embodiments less than about 15 mM NaCl and 1.5 mM trisodium citrate. For example, the wash conditions may be under conditions of 0.1×SSC to 2.0×SSC and 0.1% SDS at 50-65° C., with, for example, two steps of 10-30 min. One example of stringent wash conditions includes about 2.0×SSC, 0.1% SDS at 65° C. and washing twice, each wash step being about 30 min. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homolog, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art.

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid. It may be desirable to select conditions for a particular assay such that a higher signal to noise ratio, that is, about 15× or more, is obtained. Accordingly, an animal nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a calorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, including any of the nucleic acid sequences disclosed herein, and fragments thereof under various conditions of stringency (See, for example, Wahl and Berger (1987) Methods Enzymol. 152: 399-407; and Kimmel (1987) Methods Enzymol. 152: 507-511). With regard to hybridization, conditions that are highly stringent, and means for achieving them, are well known in the art. See, for example, Sambrook et al. (1989) "Molecular Cloning: A Laboratory Manual" (2nd ed., Cold Spring Harbor Laboratory); Berger and Kimmel, eds., (1987) "Guide to Molecular Cloning Techniques", In Methods in Enzymology:152: 467-469; and Anderson and Young (1985) "Quantitative Filter Hybridisation." In: Hames and Higgins, ed., Nucleic Acid Hybridisation, A Practical Approach. Oxford, IRL Press, 73-111.

Primers and Probes

The isolated nucleic acid of the invention which can be used as primers and/or probes can comprise about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 consecutive nucleotides from any one of SEQ ID NO: 1-10, or sequences complementary to any one of SEQ ID NO: 1-10. The isolated nucleic acid of the invention which can be used as primers and/or probes can comprise from about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 and up to about 20, 25, 30, 35, 40, 45, 50, 55, 60, 65, 70, 75, 80, 85, 90, 95 and 100 consecutive nucleotides from any one of SEQ ID NO: 1-10, or sequences complementary to any one of SEQ ID NO: 1-10. The invention is also directed to primer and/or probes which can be labeled by any suitable molecule and/or label known in the art, for example but not limited to fluorescent tags suitable for use in Real Time PCR amplification, for example TaqMan, cybergreen, TAMRA and/or FAM probes; radiolabels, and so forth. In certain embodiments, the oligonucleotide primers and/or probe further comprises a detectable non-isotopic label selected from the group consisting of: a fluorescent molecule, a chemiluminescent molecule, an enzyme, a cofactor, an enzyme substrate, and a hapten.

In yet a further aspect, the invention provides a synthetic nucleic acid which has a sequence consisting of from about 10 to about 30 consecutive nucleotides from a nucleic acid sequence selected from the group of sequences consisting of SEQ ID NO: 1-10.

In yet a further aspect, the invention provides a synthetic nucleic acid which has a sequence consisting of from about 10 to about 30 consecutive nucleotides from a nucleic acid consisting of consecutive nucleotides having a sequence which is a variant of any one of SEQ ID NOS 1-10 having at least about 95% identity to SEQ ID NO: 1-10. In one embodiment, the variant has at least about 95.5%, about 96%, about 96.5%, about 97%, about 97.5%, about 98%, about 98.5%, about 99%, about 99.5% or about 99.9% identity to SEQ ID NO: 1-10.

In another aspect, the invention provides a composition comprising one or more nucleic acids having a sequence consisting of from about 10 to about 30 consecutive nucleotides from a nucleic acids sequence selected from the group of sequences consisting of SEQ ID NO: 1-10.

In another aspect, the invention provides a composition comprising one or more nucleic acids having a sequence consisting of from about 10 to about 30 consecutive nucleotides from a nucleic acid consisting of consecutive nucleotides having a sequence which is a variant of any one of SEQ ID NOS 1-10 having at least about 95% identity to SEQ ID NO: 1-10. In one embodiment, the variant has at least about 95.5%, about 96%, about 96.5%, about 97%, about 97.5%, about 98%, about 98.5%, about 99%, about 99.5% or about 99.9% identity to SEQ ID NO: 1-10.

In yet another aspect, the invention provides a synthetic nucleic acid which has a sequence consisting of from about 10 to about 30 consecutive nucleotides from a nucleic acid sequence which is complementary to a nucleic acid sequence selected from the group of sequences consisting of SEQ ID NO: 1-10.

In yet another aspect, the invention provides a synthetic nucleic acid which has a sequence consisting of from about 10 to about 30 consecutive nucleotides complementary to a nucleic acid consisting of consecutive nucleotides having a sequence which is a variant of any one of SEQ ID NOS 1-10 having at least about 95% identity to SEQ ID NO: 1-10. In one embodiment, the variant has at least about 95.5%, about 96%, about 96.5%, about 97%, about 97.5%, about 98%, about 98.5%, about 99%, about 99.5% or about 99.9% identity to SEQ ID NO: 1-10.

In yet another aspect, the invention a composition comprising one or more synthetic nucleic acids which have a sequence consisting of from about 10 to about 30 consecutive nucleotides from a nucleic acid sequence which is complementary to a nucleic acid sequence selected from the group of sequences consisting of SEQ ID NO: 1-10.

In yet another aspect, the invention provides a composition comprising one or more synthetic nucleic acids which have a sequence consisting of from about 10 to about 30 consecutive nucleotides complementary to a nucleic acid consisting of consecutive nucleotides having a sequence which is a variant of any one of SEQ ID NOS 1-10 having at least about 95% identity to SEQ ID NO: 1-10. In one embodiment, the variant has at least about 95.5%, about 96%, about 96.5%, about 97%, about 97.5%, about 98%, about 98.5%, about 99%, about 99.5% or about 99.9% identity to SEQ ID NO: 1-10.

In other aspects the invention is directed to isolated nucleic acid sequences such as primers and probes, comprising nucleic acid sequences derived from any one of SEQ ID NO: 1-10. Such primers and/or probes may be useful for detecting the presence of the PRV of the invention, for example in samples of bodily fluids such as blood, saliva, or urine from an animal, and thus may be useful in the diagnosis of PRV infection. Such probes can detect polynucleotides of SEQ ID NO: 1-10 in samples which comprise PRV represented by SEQ ID NO: 1-10. The isolated nucleic acids which can be used as primer and/probes are of sufficient length to allow hybridization with, i.e. formation of duplex with a corresponding target nucleic acid sequence, a nucleic acid sequences of any one of SEQ ID NO: 1-10, or a variant thereof.

In one embodiment, the invention is directed to an isolated nucleic acid sequence comprising from about 10 to about 50 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 100 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 200 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 300 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 400 consecutive nucleotides from SEQ ID NO: 1 or a sequence complementary to any one of SEQ ID NO: 1-10. In one embodiment, the invention is directed to an isolated nucleic acid sequence comprising from about 10 to about 500 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 600 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 700 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 800 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 900 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 1000 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 1500 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 2000 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 2500 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 3000 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 3500 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 3600 consecutive nucleotides from any one of SEQ ID NO: 1-10 or a sequence complementary to any one of SEQ ID NO: 1-10. In one embodiment, the invention is directed to an isolated nucleic acid sequence comprising from about 10 to about 3621 consecutive nucleotides from any one of SEQ ID NO: 1-10 or a sequence complementary to any one of SEQ ID NO: 1-10.

In a further aspect, the invention provides a primer set for determining the presence or absence of the PRV in a biological sample, wherein the primer set comprises at least one synthetic nucleic acid sequence selected from the group consisting of: a synthetic nucleic acid which has a sequence consisting of from about 10 to about 30 consecutive nucleotides from a nucleic acids sequence selected from the group of sequences consisting of SEQ ID NO: 1-10, a synthetic nucleic acid which has a sequence consisting of from about 10 to about 30 consecutive nucleotides from a nucleic acids sequence which is complementary to a nucleic acid sequence selected from the group of sequences consisting of SEQ ID NO: 1-10. In one embodiment, the biological sample is derived from an animal suspected of having the PRV.

In an further aspect, the invention provides a method for determining the presence or absence of a PRV in a biological sample, the method comprising: a) contacting nucleic acid from a biological sample with at least one primer which is a nucleic acid sequence consisting of from about 10 to about 30 consecutive nucleotides from a nucleic acids sequence which is complementary to a nucleic acid sequence selected from the group of sequences consisting of SEQ ID NO: 1-10, b) subjecting the nucleic acid and the primer to amplification conditions, and c) determining the presence or absence of amplification product, wherein the presence of amplification product indicates the presence of RNA associated with PRV in the sample. In one embodiment, the biological sample is derived from a animal suspected of having a PRV.

In another aspect, the invention provides a method for determining the presence or absence of the PRV in a biological sample, the method comprising: a) contacting nucleic acid from a biological sample with at least one primer which is a synthetic nucleic acid which has a sequence consisting of from about 10 to about 30 consecutive nucleotides from a nucleic acids sequence selected from the group of sequences consisting of SEQ ID NO: 1-10, b) subjecting the nucleic acid and the primer to amplification conditions, and c) determining the presence or absence of amplification product, wherein the presence of amplification product indicates the presence of RNA associated with PRV in the sample.

In still a further aspect, the invention provides for an interfering RNA (iRNA) comprising a sense strand having at least 15 contiguous nucleotides complementary to a nucleic acid sequence of any of SEQ ID NO: 1-10.

In still another aspect, the invention provides a method of reducing the levels of a viral protein, viral mRNA or viral titer in a cell in an animal comprising: administering at least one iRNA agent to an animal, wherein the iRNA agent comprising a sense strand having at least 15 contiguous nucleotides complementary to gene from a PRV comprising any of SEQ ID NO: 1-10 and an antisense strand having at least 15 contiguous nucleotides complementary to the sense strand. In one embodiment, the iRNA agent is administered to an animal. In another embodiment, the iRNA agent is administered via nebulization to an animal. In yet another embodiment, the method further comprises co-administering a second iRNA agent to the animal, wherein the second iRNA agent comprising a sense strand having at least 15 or more contiguous nucleotides complementary to second gene from the PRV, and an antisense strand having at least 15 or more contiguous nucleotides complementary to the sense strand.

In another aspect, the invention provides a method of reducing the levels of a viral protein in a cell in an animal comprising the step of administering an iRNA agent to an animal, wherein the iRNA agent comprises a sense strand having at least 15 or more contiguous nucleotides complementary to a gene from a PRV comprising SEQ ID NO: 1-10 and an antisense strand having at least 15 or more contiguous nucleotides complementary to the sense strand.

In certain aspects, the invention is directed to iRNA molecules which target nucleic acids from PRV, for example but not limited to SEQ ID NO: 1-10, and variants thereof, and silence a target gene.

An "iRNA agent" (abbreviation for "interfering RNA agent") as used herein, is an RNA agent, which can down-regulate the expression of a target gene, e.g. a PRV gene. An iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded (ds) iRNA agent.

A "ds iRNA agent" (abbreviation for "double stranded iRNA agent"), as used herein, is an iRNA agent which includes more than one, and in certain embodiments two, strands in which interchain hybridization can form a region of duplex structure. A "strand" herein refers to a contiguous sequence of nucleotides (including non-naturally occurring or modified nucleotides). The two or more strands may be, or each form a part of, separate molecules, or they may be covalently interconnected, e.g. by a linker, e.g. a polyethyleneglycol linker, to form but one molecule. At least one strand can include a region which is sufficiently complementary to a target RNA. Such strand is termed the "antisense strand". A second strand comprised in the dsRNA agent which comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand" refers to one of the regions of the RNA molecule that is complementary to another region of the same RNA molecule.

iRNA agents as described herein, including ds iRNA agents and siRNA agents, can mediate silencing of a gene, e.g., by RNA degradation. For convenience, such RNA is also referred to herein as the RNA to be silenced. Such a gene is also referred to as a target gene. In certain embodiments, the RNA to be silenced is a gene product of a PRV gene.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

In the anti viral uses of the present invention, silencing of a target gene can result in a reduction in "viral titer" in the cell or in the animal, wherein "reduction in viral titer" refers to a decrease in the number of viable virus produced by a cell or found in an organism undergoing the silencing of a viral target gene. Reduction in the cellular amount of virus produced can lead to a decrease in the amount of measurable virus produced in the tissues of an animal undergoing treatment and a reduction in the severity of the symptoms of the viral infection. iRNA agents of the present invention are also referred to as "antiviral iRNA agents".

As used herein, a "PRV gene" refers to any one of the genes identified in the PRV genome.

In other aspects, the invention provides methods for reducing viral titer in an animal, by administering to an animal, at least one iRNA which inhibits the expression of a PRV gene.

In other aspects, the invention provides methods for identifying and/or generating anti-viral drugs. For example, in one aspect the invention provides methods for identifying drugs that bind to and/or inhibit the function of the PRV-encoded proteins of the invention, or that inhibit the replication or pathogenicity of the PRV of the invention. Methods of identifying drugs that affect or inhibit a particular drug target, such as high throughput drug screening methods, are well known in the art and can readily be applied to the proteins and viruses of the present invention.

In one aspect, the invention provides an isolated PRV polypeptide encoded by a PRV nucleic acid sequence in any of SEQ ID NOs: 1-10, or a fragment thereof.

The PRV polypeptides and amino acid sequences described herein may be useful for, inter alia, expression of PRV -encoded proteins or fragments, variants, or derivatives thereof, generation of diagnostic antibodies against PRV proteins, generation of primers and probes for detecting PRV and/or for diagnosing PRV infection, and screening for drugs effective against Piscine reoviruses as described herein.

In one embodiment, the PRV polypeptide fragment can be a polypeptide comprising about 8 consecutive amino acids of a PRV polypeptide described herein. In another embodiment, the fragment can be a polypeptide comprising about 10 consecutive amino acids of a PRV polypeptide described herein. In another embodiment, the fragment can be a polypeptide comprising about 14 consecutive amino acids of a PRV polypeptide described herein. In another embodiment, the fragment can be a polypeptide comprising about 16 consecutive amino acids of a PRV polypeptide described herein. In another embodiment, the fragment can be a polypeptide comprising about 18 consecutive amino acids of a PRV polypeptide described herein. In another embodiment, the fragment can be a polypeptide comprising about 20 consecutive amino acids of a PRV polypeptide described herein. In another embodiment, the fragment can be a polypeptide comprising about 21 or more consecutive amino acids of a PRV polypeptide described herein.

In yet another embodiment, the PRV polypeptide fragment can be a polypeptide comprising from about 8 to about 50, about 8 to about 100, about 8 to about 200, about 8 to about 300, about 8 to about 400, about 8 to about 500, about 8 to about 600, about 8 to about 700, about 8 to about 800, about 8 to about 900 or more consecutive amino acids from a PRV polypeptide.

In another aspect, the invention provides an isolated PRV polypeptide encoded by a nucleic acid which comprises consecutive nucleotides having a sequence selected from a PRV nucleic acid sequence in any of SEQ ID NOs: 1-10, or a fragment thereof.

In another aspect, the invention provides an isolated PRV polypeptide encoded by a nucleic acid which comprises consecutive nucleotides having a sequence selected from a variant of a PRV nucleic acid sequence in any of SEQ ID NOs: 1-10 or a fragment thereof. In one embodiment, the variant has at least about 85% identity to SEQ ID NOs: 1-10, or a fragment thereof. In one embodiment of the above aspect of the invention, the variant has at least about 90%, about 95.5%, about 96%, about 96.5%, about 97%, about 97.5%, about 98%, about 98.5%, about 99%, about 99.5% or about 99.9% identity to that of any one of SEQ ID NOs: 1-10, or a fragment thereof.

In one aspect, the invention provides an isolated PRV polypeptide encoded by a nucleic acid complementary a PRV nucleic acid sequence in any of SEQ ID NOs: 1-10, or a fragment thereof.

In another aspect, the invention provides an isolated PRV polypeptide encoded by a nucleic acid which comprises consecutive nucleotides a PRV nucleic acid sequence in any of SEQ ID NOs: 1-10, or a fragment thereof.

In another aspect, the invention provides an isolated PRV polypeptide encoded by a nucleic acid having a sequence substantially identical to a PRV nucleic acid sequence in any of SEQ ID NOs: 1-10, or a fragment thereof.

In another aspect, the invention provides an isolated PRV polypeptide encoded by a nucleic acid having a sequence substantially identical to a sequence complementary to a PRV nucleic acid sequence in any of SEQ ID NOs: 1-10, or a fragment thereof.

In one aspect, the invention provides an isolated PRV polypeptide having the sequence of any of SEQ ID NOs: 29-40, or a fragment thereof.

In another aspect, the invention provides an isolated PRV polypeptide which comprises consecutive amino acids having a sequence selected from the group consisting of any of SEQ ID NOs: 29-40, or a fragment thereof.

In another aspect, the invention provides an isolated PRV polypeptide which comprises consecutive amino acids having a sequence selected from a variant of any of SEQ ID NOs: 29-40, or a fragment thereof. In one embodiment, the variant has at least about 85% identity to SEQ ID NOs: 29-40, or a fragment thereof. In one embodiment of the above aspect of the invention, the variant has at least about 90%, about 95.5%, about 96%, about 96.5%, about 97%, about 97.5%, about 98%, about 98.5%, about 99%, about 99.5% or about 99.9% identity to that of any one of SEQ ID NOs: 1-10, or a fragment thereof.

In another aspect, the invention provides an isolated PRV polypeptide having a sequence substantially identical to a PRV amino acid sequence in any of SEQ ID NOs: 29-40, or a fragment thereof.

In one aspect, the invention provides an isolated PRV polypeptide encoded by a PRV nucleic acid sequence in any of SEQ ID NOs: 1-10, or a fragment thereof.

In one embodiment, the isolated PRV polypeptide fragment can be a polypeptide comprising about 8 consecutive amino acids of a PRV amino acid sequence of any of SEQ ID NOs: 29-40. In another embodiment, the fragment can be a polypeptide comprising about 10 consecutive amino acids of a PRV amino acid sequence of any of SEQ ID NOs: 29-40. In another embodiment, the fragment can be a polypeptide comprising about 14 consecutive amino acids of a PRV amino acid sequence of any of SEQ ID NOs: 29-40. In another embodiment, the fragment can be a polypeptide comprising about 16 consecutive amino acids of a PRV amino acid sequence of any of SEQ ID NOs: 29-40. In another embodiment, the fragment can be a polypeptide comprising about 18 consecutive amino acids of a PRV amino acid sequence of any of SEQ ID NOs: 29-40. In another embodiment, the fragment can be a polypeptide comprising about 20 consecutive amino acids of a PRV amino acid sequence of any of SEQ ID NOs: 29-40. In another embodiment, the fragment can be a polypeptide comprising about 21 or more consecutive amino acids of a PRV amino acid sequence of any of SEQ ID NOs: 29-40.

In yet another embodiment, the isolated PRV polypeptide fragment can be a polypeptide comprising from about 8 to about 50, about 8 to about 100, about 8 to about 200, about 8 to about 300, about 8 to about 400, about 8 to about 500, about 8 to about 600, about 8 to about 700, about 8 to about 800, about 8 to about 900 or more consecutive amino acids of a PRV amino acid sequence of any of SEQ ID NOs: 29-40.

In another aspect, the invention provides an isolated PRV polypeptide which comprises consecutive amino acids having a sequence selected from a PRV amino acid sequence of any of SEQ ID NOs: 29-40.

In another aspect, the invention provides an isolated PRV polypeptide which comprises consecutive nucleotides having a sequence selected from a variant a PRV amino acid sequence of any of SEQ ID NOs: 29-40, or a fragment thereof. In one embodiment, the variant has at least about 85% identity to any of SEQ ID NOs: 29-40, or a fragment thereof. In one embodiment of the above aspect of the invention, the variant has at least about 90%, about 95.5%, about 96%, about 96.5%, about 97%, about 97.5%, about 98%, about 98.5%, about 99%, about 99.5% or about 99.9% identity to any of SEQ ID NOs: 29-40, or a fragment thereof.

In another aspect, the invention provides an isolated PRV polypeptide substantially identical to variant a PRV amino acid sequence of any of SEQ ID NOs: 29-40, or a fragment thereof.

"Substantially identical," in the context of two nucleic acids or polypeptides, refers to two or more sequences or subsequences that have at least of at least 98%, at least 99% or higher nucleotide or amino acid residue identity, when compared and aligned for maximum correspondence, as measured using one of the following sequence comparison algorithms or by visual inspection. Thus, in certain embodiments, polypeptides that a substantially identical to the PRV polypeptides described herein can also be used to generate diagnostic antibodies that bind to the PRV polypeptides described herein.

"Percent identity" in the context of two or more nucleic acids or polypeptide sequences, refers to the percentage of nucleotides or amino acids that two or more sequences or subsequences contain which are the same. A specified percentage of amino acid residues or nucleotides can have a specified identity over a specified region, when compared and aligned for maximum correspondence over a comparison window, or designated region as measured using one of the following sequence comparison algorithms or by manual alignment and visual inspection. In one aspect, the invention provides a PRV polypeptide which is a variant of a PRV polypeptide and has at least about 90%, about 95.5%, about 96%, about 96.5%, about 97%, about 97.5%, about 98%, about 98.5%, about 99%, about 99.5% or about 99.9% identity to a PRV polypeptide shown in SEQ ID NOs 29-40.

It will be understood that, for the particular PRV polypeptides described here, natural variations can exist between individual PRV strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino 15 acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino acid substitutions 20 include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/ Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity. It is know that polypeptide sequences having one or more amino acid sequence variations as compared to a reference polypeptide may still be useful for generating antibodies that bind the reference polypeptide. Thus in certain embodiments, the PRV polypeptides and the antibodies and antibody generation methods related thereto encompass PRV polypeptides isolated from different virus isolates that have sequence identity levels of at least about 90%, while still representing the same PRV protein with the same immunological characteristics.

The sequence identities can be determined by analysis with a sequence comparison algorithm or by a visual inspection. Protein and/or nucleic acid sequence identities (homologies) can be evaluated using any of the variety of sequence comparison algorithms and programs known in the art.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated.

Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.2.2. or FASTA version 3.0t78 algorithms and the default parameters discussed below can be used.

An example of an algorithm that is suitable for determining percent sequence identity and sequence similarity is the FASTA algorithm, which is described in Pearson, W. R. & Lipman, D. J., Proc. Natl. Acad. Sci. U.S.A. 85: 2444, 1988. See also W. R. Pearson, Methods Enzymol. 266: 227-258, 1996. Exemplary parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Another example of algorithm that is suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. BLAST and BLAST 2.0 are used, with the parameters described herein, to determine percent sequence identity for the nucleic acids and proteins of the invention. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. U.S.A. 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. U.S.A. 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, less than about 0.01, and less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360, 1987. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395, 1984.

Another example of an algorithm that is suitable for multiple DNA and amino acid sequence alignments is the CLUSTALW program (Thompson, J. D. et al., Nucl. Acids. Res. 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, Proc. Natl. Acad. Sci. U.S.A. 89:10915-10919, 1992).

In yet a further aspect, the invention provides a computer readable medium having stored thereon (i) a nucleic acid sequence selected from the group consisting of: a PRV nucleic acid sequence in any of SEQ ID NOs: 1-10, a sequence substantially identical to a PRV nucleic acid sequence in any of SEQ ID NOs: 1-10; a sequence variant of a PRV nucleic acid sequence in any of SEQ ID NOs: 1-10; or (ii) an amino acid sequence encoded by a nucleic acid sequence selected from the group consisting of: a PRV nucleic acid sequence in any of SEQ ID NOs: 1-10, an amino acid sequence encoded by a sequence substantially identical to a PRV nucleic acid sequence in any of SEQ ID NOs: 1-10; an amino acid sequence encoded by a sequence variant of a PRV nucleic acid sequence in any of SEQ ID NOs: 1-10.

The PRV nucleic acid sequences described herein may be useful for, inter alia, expression of PRV -encoded proteins or fragments, variants, or derivatives thereof, generation of diagnostic antibodies against PRV proteins (e.g. for determining whether an animal has been infected with PRV), generation of primers and probes for detecting PRV and/or for diagnosing PRV infection, and screening for drugs effective against Piscine reoviruses as described herein.

In certain embodiments, the polypeptides of the present invention can be suitable for use as antigens to detect antibodies against PRV represented by SEQ ID NOs: 1-10, and variants thereof. In other embodiments, the polypeptides of the present invention which comprise antigenic determinants can be used in various immunoassays to identify animals exposed to and/or samples which comprise PRV represented by SEQ ID NO: 1-10, and variants thereof.

In one aspect, the invention provides a diagnostic PRV antibody that binds a PRV, a PRV polypeptide, a PRV polypeptide fragment or a PRV polypeptide variant, or a polypeptide substantially identical to a PRV polypeptide and wherein the antibody is an antibody that binds a PRV or a PRV polypeptide but does not inhibit, neutralize or reduce the activity or function of the polypeptide or the PRV. In some embodiments, the diagnostic antibody is a polyclonal antibody, a monoclonal antibody, a teleost antibody or a chimeric antibody. Methods for purifying immunoglobulins from teleosts are also known in the art. See, for example, Havarstein et al, Dev Comp Immunol 1988, 12(4):773-85; Al-Harbi et al, Bull Eur Ass Fish Pathol 1993,13:40-4; Itami et al, Nippon Suisan Gakkaishi 1988, 54(9):1611-7.

In another aspect, the invention provides a method for determining whether or not a sample contains a PRV, the method comprising: (a) providing an immunoassay comprising a diagnostic antibody against a PRV derived antigen, (b) contacting the diagnostic antibody with a biological sample, (c) detecting binding between antigens in the test sample and the diagnostic antibody. In one embodiment, the immunoassay is a lateral flow assay or ELISA. In one embodiment, the biological sample is derived from an animal suspected of having a PRV.

In still a further aspect, the invention provides a method for determining whether or not a sample contains antibodies against PRV, the method comprising: (a) providing an immunoassay comprising an antigen from a PRV, (b) contacting the antigen with a biological sample, (c) detecting binding between antibodies in the test sample and the antigen.

The diagnostic antibodies of the invention can also be used to purify polypeptides of any polypeptide encoded by the nucleic sequence acid of any one of SEQ ID NO: 1-10, polypeptides comprising the sequence of any of SEQ ID NOs: 29-40, or variants or fragments thereof.

In other embodiments, the diagnostic antibodies of the invention can be used to identify expression and localization of a PRV polypeptide or variants or fragments thereof. Analysis of expression and localization of PRV polypeptides, or variants or fragments thereof, can be useful in diagnosing a PRV infection or for determining potential role of a PRV polypeptide.

In other embodiments, the antibodies of the present invention can be used in various immunoassays to identify animals exposed to and/or samples which comprise antigens from PRV.

Any suitable immunoassay which can lead to formation of antigen-antibody complex can also be used. Variations and different formats of immunoassays, for example but not limited to ELISA, lateral flow assays for detection of analytes in samples, immunoprecipitation, are known in the art. In various embodiments, the antigen and/or the antibody can be labeled by any suitable label or method known in the art. For example enzymatic immunoassays may use solid supports, or immunoprecipitation. Immunoassays which amplify the signal from the antigen-antibody immune complex can also be used with the methods described herein.

In certain aspects the invention provides methods for assaying a sample to determine the presence or absence of a PRV polypeptide, or a fragment or a variant thereof. In certain embodiments, methods for assaying a sample, include, but are not limited to, methods which can detect the presence of nucleic acids, methods which can detect the presence of PRV polypeptides, methods which can detect the presence of antibodies against PRV polypeptides, or any polypeptide encoded by a PRV nucleic acid.

In still a further aspect, the invention provides a PRV diagnostic kit comprising a PRV nucleic acid, a PRV nucleic acid fragment or a PRV nucleic acid variant, a nucleic acid substantially identical to a PRV nucleic acid, or a PRV diagnostic antibody.

One of skill in the art will recognize that when diagnostic antibodies or nucleic acid are used for diagnostic purposes, it is not necessary to use the entire nucleic acid or diagnostic antibody to detect a PRV or a PRV polypeptide in an animal or in a sample. In certain aspects, the invention is directed to methods for generating diagnostic antibodies that bind to the PRV polypeptides described herein by generating antibodies that bind to a fragment of a polypeptide described herein. Thus, in one aspect, the invention relates to diagnostic kits for detecting PRV infection or the presence of PRV in a sample, that comprise a PRV nucleic acid or a PRV diagnostic antibody.

In other aspect, the invention provides a nucleic acid vector comprising a PRV nucleic acid sequence, a PRV nucleic acid fragment or a PRV nucleic acid variant, or a nucleic acid substantially identical to a PRV nucleic acid.

In another aspect, the invention provides a nucleic acid vector encoding a PRV polypeptide, a PRV polypeptide fragment or a PRV polypeptide variant, or a polypeptide substantially identical to a PRV polypeptide. Non-limiting examples of vectors include, but are not limited to retroviral, adenoviral, adeno-associated viral, lentiviral, and vesiculostomatitis viral vectors.

In yet another aspect, the invention provides a host organism comprising a nucleic acid vector encoding a PRV polypeptide, a PRV polypeptide fragment, a PRV polypeptide variant, a polypeptide substantially identical to a PRV polypeptide or a the diagnostic PRV antibody that binds a PRV, a PRV polypeptide, a PRV polypeptide fragment or a PRV polypeptide variant, or a polypeptide substantially identical to a PRV polypeptide and which does not inhibit, neutralize or reduce the activity or function of the polypeptide or the PRV. In one embodiment, the host organism is a prokaryote, a eukaryote, or a fungus. In another embodiment the organism is a teleost (e.g. a salmon).

To produce the PRV polypeptides and diagnostic PRV antibodies described herein, the PRV nucleic acid sequences of the invention can be delivered to cultured cells, for example by transfecting cultured cells with plasmids or expression vectors containing PRV nucleic acid sequences, or by infecting cultured cells with recombinant viruses containing PRV nucleic acid sequences. PRV polypeptides may then be expressed in a host cell or expression system and purified. A host cell may be a cell of bacterial origin, e.g. *Escherichia coli, Bacillus subtilis* and *Lactobacillus* species, in combination with bacteria-based plasmids as pBR322, or bacterial expression vectors as pGEX, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses. In vitro expression systems, such as in-vitro transcription and in-vitro translation systems can also be used to generate the PRV polypeptides described herein. The purified proteins can then be incorporated into compositions suitable for administration to animals. Methods and techniques for expression and purification of recombinant proteins are well known in the art, and any such suitable methods may be used.

Any suitable plasmid or expression vector capable of driving expression of a polypeptide may be used. Plasmids and expression vectors can include a promoter for directing transcription of the nucleic acid. The nucleic acid sequence encoding PRV polypeptides may also be incorporated into a suitable recombinant virus for administration to the animal. Examples of suitable viruses include, but are not limited to, vaccinia viruses, retroviruses, adenoviruses and adeno-associated viruses. One of skill in the art will be able to select a suitable plasmid, expression vector, or recombinant virus for delivery of the PRV nucleic acid sequences of the invention. Direct vaccination with DNA encoding proteins has been successful for many different proteins. (As reviewed in e.g. Donnelly et al. The Immunologist 2: 20-26 (1993)).

The diagnostic PRV antibodies described herein can also be generated using live recombinant carriers capable of expressing the polypeptides described herein. Live recombinant carriers are micro-organisms or viruses in which additional genetic information, e.g. a nucleic acid sequence encoding a PRV polypeptide, or a fragment thereof has been cloned. Animals infected with such live recombinant carriers will produce an immunological response not only against the immunogens of the carrier, but also against the PRV polypeptide or PRV polypeptide fragment. Non-limiting examples of live recombinant carriers suitable for use with the methods described herein includes *Vibrio anguillarum* (Singer, J. T. et al. New Developments in Marine Biotechnology, p. 303-306, Eds. Le Gal and Halvorson, Plenum Press, New York, 1998), and alphavirus-vectors (Sondra Schlesinger and Thomas W. Dubensky Jr. Alphavirus vectors for gene expression and vaccines. Current opinion in Biotechnology, 10:434439 (1999)

The diagnostic PRV antibodies described herein can also be generated by any other method known in the art. Exemplary alternative in-vitro antibody generation technologies, transgenic animal technologies and hybridoma technologies. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, Antibodies, A Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

In-vitro technologies suitable for generating the diagnostic PRV antibodies described herein include, but are not limited to, ribosome display, yeast display, and bacterial display technologies. Ribosome display is a method of translating mRNAs into their cognate proteins while keeping the protein attached to the RNA. The nucleic acid coding sequence is recovered by RT-PCR (Mattheakis, L. C. et al. 1994. Proc Natl Acad Sci USA 91, 9022). Yeast display is based on the construction of fusion proteins of the membrane-associated alpha-agglutinin yeast adhesion receptor, aga1 and aga2, a part of the mating type system (Broder, et al. 1997. Nature Biotechnology, 15:553-7). Bacterial display is based fusion of the target to exported bacterial proteins that associate with the cell membrane or cell wall (Chen and Georgiou 2002. Biotechnol Bioeng, 79:496-503). In comparison to hybridoma technology, phage and other antibody display methods afford the opportunity to manipulate selection against the antigen target in vitro and without the limitation of the possibility of host effects on the antigen or vice versa.

For example, the diagnostic PRV antibodies described herein that bind a PRV polypeptide, a PRV polypeptide fragment or a PRV polypeptide variant, or a polypeptide substantially identical to a PRV polypeptide and which do not inhibit, neutralize or reduce the activity or function of the polypeptide or the PRV may be obtained by selecting from libraries, e.g. a phage library. A phage library can be created by inserting a library of random oligonucleotides or a library of polynucleotides containing sequences of interest, such as from the B-cells of an immunized animal (Smith, G. P. 1985. Science 228: 1315-1317). Antibody phage libraries contain heavy (H) and light (L) chain variable region pairs in one phage allowing the expression of single-chain Fv fragments or Fab fragments (Hoogenboom, et al. 2000, Immunol Today 21(8) 371-10). The diversity of a phagemid library can be manipulated to increase and/or alter the immunospecificities of the monoclonal antibodies of the library to produce and subsequently identify additional, teleost monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable affinity and neutralization capabilities. Antibody libraries also can be created synthetically by selecting one or more framework sequences and introducing collections of CDR cassettes derived from antibody repertoires or through designed variation (Kretzschmar and von Ruden 2000, Current Opinion in Biotechnology, 13:598-602). The positions of diversity are not limited to CDRs but can also include the framework segments of the variable regions or may include other than antibody variable regions, such as peptides.

Other antibody generation techniques suitable for generating diagnostic PRV antibodies against the PRV polypeptides described herein include, the PEPSCAN technique described in Geysen et al (Patent Application WO 84/03564, Patent Application WO 86/06487, U.S. Pat. No. 4,833,092, Proc. Natl. Acad. Sci. 81: 3998-4002 (1984), J. Imm. Meth. 102, 259-274 (1987).

Pepsin or papain digestion of whole diagnostic PRV antibodies that bind PRV polypeptides can be used to generate diagnostic PRV antibodies fragments that bind PRV polypeptides. In particular, an Fab fragment consists of a monovalent antigen-binding fragment of an diagnostic antibody molecule, and can be produced by digestion of a whole diagnostic antibody molecule with the enzyme papain, to yield a fragment consisting of an intact light chain and a portion of a heavy chain. An $(Fab')_2$ fragment of an diagnostic antibody can be obtained by treating a whole diagnostic antibody molecule with the enzyme pepsin, without subsequent reduction. An Fab' fragment of an diagnostic antibody molecule can be obtained from $(Fab')_2$ by reduction with a thiol reducing agent, which yields a molecule consisting of an intact light chain and a portion of a heavy chain. Two Fab' fragments are obtained per diagnostic antibody molecule treated in this manner.

Diagnostic PRV antibodies can be produced through chemical crosslinking of the selected molecules (which have been produced by synthetic means or by expression of nucleic acid that encode the polypeptides) or through recombinant DNA technology combined with in vitro, or cellular expression of the polypeptide, and subsequent oligomerization. Antibodies can be similarly produced through recombinant technology and expression, fusion of hybridomas that produce antibodies with different epitope specificities, or expression of multiple nucleic acid encoding antibody variable chains with different epitopic specificities in a single cell.

The diagnostic antibodies described herein may be either joined directly or indirectly through covalent or non-covalent binding, e.g. via a multimerization domain, to produce multimers. A "multimerization domain" mediates non-covalent protein-protein interactions. Specific examples include coiled-coil (e.g., leucine zipper structures) and alpha-helical protein sequences. Sequences that mediate protein-protein binding via Van der Waals' forces, hydrogen bonding or charge-charge bonds can also be used as multimerization domains. Additional examples include basic-helix-loop-helix domains and other protein sequences that mediate heteromeric or homomeric protein-protein interactions among nucleic acid binding proteins (e.g., DNA binding transcription factors, such as TAFs). One specific example of a multimerization domain is p53 residues 319 to 360 which mediate tetramer formation. Another example is human platelet factor 4, which self-assembles into tetramers. Yet another example is extracellular protein TSP4, a member of the thrombospondin family, which can form pentamers. Additional specific examples are the leucine zippers of jun, fos, and yeast protein GCN4.

The diagnostic antibodies described herein s may be directly linked to each other via a chemical cross linking agent or can be connected via a linker sequence (e.g., a peptide sequence) to form multimers.

The diagnostic antibodies described herein can be polyclonal or monoclonal. The antibodies can also be chimeric (i.e., a combination of sequences from more than one species, for example, a chimeric mouse-salmon immunoglobulin). The presence of such protein sequences form other species can lead to the rapid clearance of the antibodies or can lead to the generation of an immune response against the antibody by an antibody.

The diagnostic antibodies described herein can be antibodies that bind to other molecules (antigens) via heavy and light chain variable domains, $V_H$ and $V_L$, respectively. The antibodies described herein include, but are not limited to IgY, IgY(ΔFc)), IgG, IgD, IgA, IgM, IgE, and IgL. The antibodies may be intact immunoglobulin molecules, two full length heavy chains linked by disulfide bonds to two full length light chains, as well as subsequences (i.e. fragments) of immunoglobulin molecules, with or without constant region, that bind to an epitope of an antigen, or subsequences thereof (i.e. fragments) of immunoglobulin molecules, with or without constant region, that bind to an epitope of an antigen. Antibodies may comprise full length heavy and light chain variable domains, $V_H$ and $V_L$, individually or in any combination.

The basic immunoglobulin (antibody) structural unit can comprise a tetramer. Each tetramer can be composed of two identical pairs of polypeptide chains, each pair having one “light” (about 25 kD) and one “heavy” chain (about 50-70 kD). The N-terminus of each chain defines a variable region of about 100 to 110 or more amino acids primarily responsible for antigen recognition. The terms variable light chain ($V_1$) and variable heavy chain ($V_H$) refer to these light and heavy chains respectively.

The diagnostic antibodies described herein may exist as intact immunoglobulins or as a number of well characterized fragments produced by digestion with various peptidases. In particular, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially an Fab with part of the hinge region (see, Fundamental Immunology, W. E. Paul, ed., Raven Press, N.Y. (1993) for more antibody fragment terminology). While the Fab' domain is defined in terms of the digestion of an intact antibody, one of skill will appreciate that such Fab' fragments may be synthesized de novo either chemically or by utilizing recombinant DNA methodology. The Fab' regions may be derived from antibodies of animal origin or may be chimeric (Morrison et al., Proc Natl. Acad. Sci. USA 81, 6851-10855 (1984) both incorporated by reference herein) (Jones et al., Nature 321, 522-525 (1986), and published UK patent application No. 8707252, both incorporated by reference herein).

The diagnostic antibodies described herein can include or be derived from any mammal, such as but not limited to, a fish, a human, a mouse, a rabbit, a rat, a rodent, a primate, or any combination thereof and includes isolated fish, human, primate, rodent, mammalian, chimeric, humanized and/or CDR-grafted or CDR-adapted antibodies, immunoglobulins, cleavage products and other portions and variants thereof. In one embodiment the antibody is purified.

The diagnostic antibodies described herein include full length antibodies, subsequences (e.g., single chain forms), dimers, trimers, tetramers, pentamers, hexamers or any other higher order oligomer that retains at least a part of antigen binding activity of monomer. Multimers can comprise heteromeric or homomeric combinations of full length antibody, subsequences, unmodified or modified as set forth herein and known in the art. Antibody multimers are useful for increasing antigen avidity in comparison to monomer due to the multimer having multiple antigen binding sites. Antibody multimers are also useful for producing oligomeric (e.g., dimer, trimer, tertamer, etc.) combinations of different antibodies thereby producing compositions of antibodies that are multifunctional (e.g., bifunctional, trifunctional, tetrafunctional, etc.).

Specific examples of diagnostic antibody subsequences include, for example, Fab, Fab', $(Fab')_2$, Fv, or single chain antibody (SCA) fragment (e.g., scFv). Subsequences include portions which retain at least part of the function or activity of full length sequence. For example, an antibody subsequence will retain the ability to selectively bind to an antigen even though the binding affinity of the subsequence may be greater or less than the binding affinity of the full length antibody.

An Fv fragment is a fragment containing the variable region of a light chain $V_L$ and the variable region of a heavy chain $V_H$ expressed as two chains. The association may be non-covalent or may be covalent, such as a chemical cross-linking agent or an intermolecular disulfide bond (Inbar et al., (1972) Proc. Natl. Acad Sci. USA 69:2659; Sandhu (1992) Crit. Rev. Biotech. 12:437).

Other methods of producing subsequences of the diagnostic antibodies described herein, such as separation of heavy chains to form monovalent light-heavy chain fragments, further cleavage of fragments, or other enzymatic, chemical, or genetic techniques may also be used, provided that the subsequences bind to the antigen to which the intact antibody binds.

A single chain antibody (“SCA”) is a genetically engineered or enzymatically digested antibody containing the variable region of a light chain $V_L$ and the variable region of a heavy chain, optionally linked by a flexible linker, such as a polypeptide sequence, in either $V_L$-linker-$V_H$ orientation or in $V_H$-linker-$V_L$ orientation. Alternatively, a single chain Fv fragment can be produced by linking two variable domains via a disulfide linkage between two cysteine residues. Methods for producing scFv antibodies are described, for example, by Whitlow et al., (1991) In: Methods: A Companion to Methods in Enzymology 2:97; U.S. Pat. No. 4,946,778; and Pack et al., (1993) Bio/Technology 11:1271.

The PRV nucleic acids and polypeptides described herein can be used to generate diagnostic antibodies that that can be used to detect the present or absence of a PRV or a PRV polypeptide in an animal or in a sample The following examples illustrate the present invention, and are set forth to aid in the understanding of the invention, and should not be construed to limit in any way the scope of the invention as defined in the claims which follow thereafter.

EXAMPLES

Example 1

Isolation of PRV Fragment

A 200 nt fragment that is approximately 50% homologous at the amino acid level to mammalian Orthoreoviruses was obtained through high throughput sequencing of samples obtained from farmed salmon with HSMI in Norway. Quantitative PCR assays of muscle tissue from salmon with HSMI and normal salmon reveals a higher viral load in salmon with HSMI.

Example 2

Heart and Skeletal Muscle Inflammation of Farmed Salmon is Associated with Infection with a Novel Reovirus RNA extracted from heart of a salmon with experimentally induced HMSI was pyrosequenced (Margulies, M. et al., Nature 437, 376-380 (2005)) yielding 106,073 reads ranging in size up to 598 nucleotide (average=349.7, SD=149.5). Although database alignment analysis at the nucleotide level revealed no evidence of infection, the predicted amino acid sequence of one 265 nucleotide read was 49% similar to the core-spike protein λ2 of Mammalian orthoreovirus 3 (AF378009). A real time PCR assay based on this sequence was used to test for the presence of the candidate virus in RNA extracts of heart and serum obtained from salmon with HSMI in association with spontaneous outbreaks (n=20) or experimental infection (n=20), and in non-infected control fish (n=20). All samples from salmon with HSMI contained the candidate sequences. No sequences were found in the control salmon without HSMI.

The HSMI serum sample with the highest genetic load by PCR (3.0×106 genome copies/μl) was selected for additional pyrosequencing yielding 120,705 reads. A suite of bioinformatic tools was used to identify viral sequences. In the first phase of analysis, BLASTN and BLASTX (Altschul et al., J Mol Biol 215, 403-410 (1990)) detected 1.5% and 53.9% of the predicted viral genome, respectively, enabling identification of segments L1, L2, L3, M1, M2 and M3 (FIG. 1). Implementation of FASTX (Pearson et al., Genomics 46, 24-36(1997)) yielded an additional 5.5% of the genome and detected motifs in the S1 segment as well as additional sequences in the L2 and M3 segments. Frequency Analysis of Sequence Data (FASD) (Trifonov et al, (submitted)), a program that predicts taxonomy based on nucleotide frequency and order rather than sequence alignment, detected new sequences representing the S1, S2, S3 and S4 segments (FIG. 1) that comprised an additional 11.8% of the final viral genome assembly. In total, approximately 17 kilobases of sequence (72.8% of the genome) was obtained by pyrosequencing (FIG. 1). Gaps between fragments and the termini of gene segments were completed by PCR cloning. All sequence was verified by classical dideoxy sequencing by using primers designed along the draft sequence.

Figure 2:
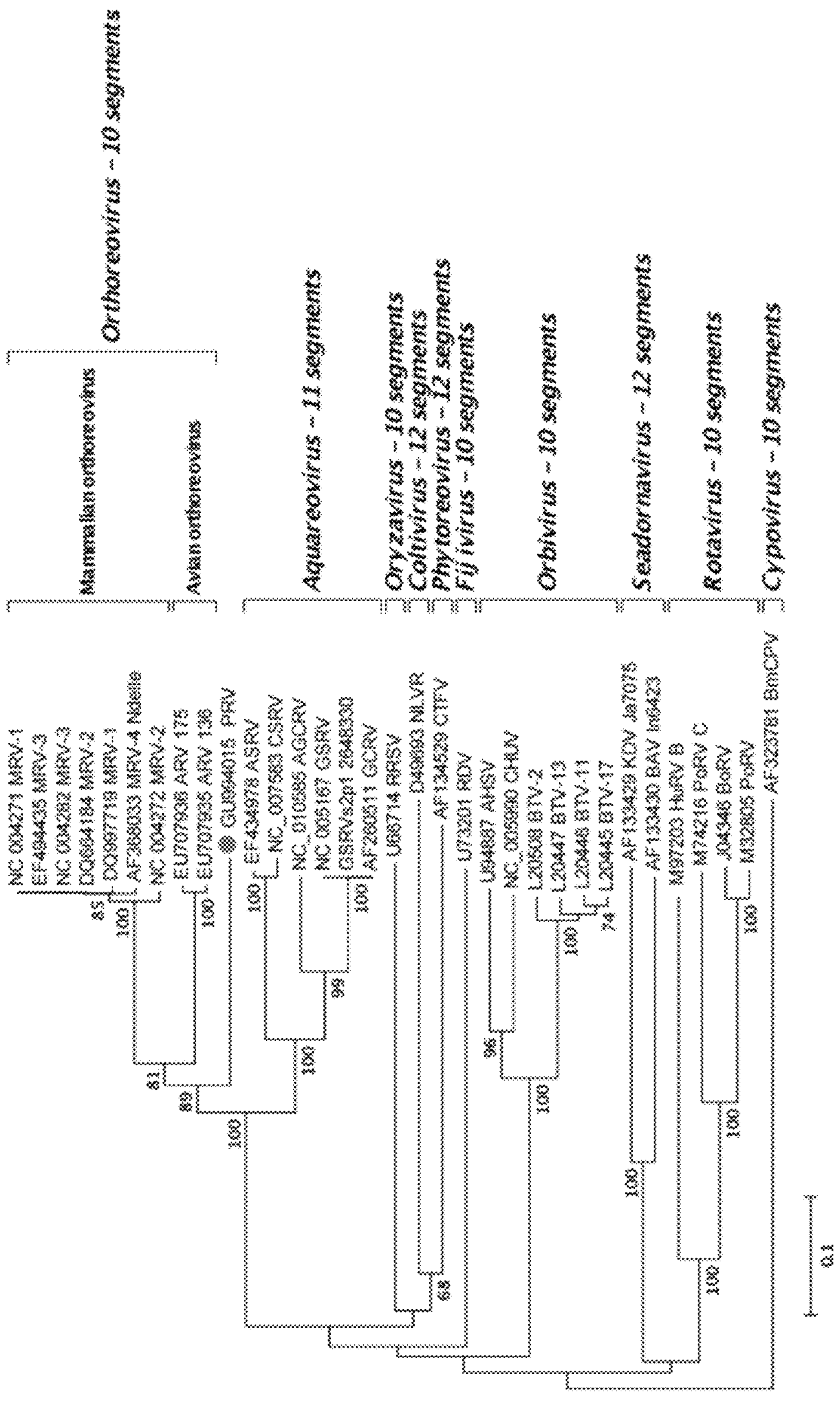
FIG. 2. Phylogenetic analysis of the RNA-dependent RNA-polymerase of Reoviridae. Full length amino acid sequences were aligned using the ClustalX14 implemented on MEGA software (Tamura et al., Mol Biol Evol 24, 1596-1599 (2007)) and refined using T-Coffee (Notredame et al., J Mol Biol 302, 205-217 (2000)) to incorporate protein structure data. Phylogenetic analysis was performed using p-distance as model of amino acid substitution as implemented by ICTV for analysis of the Reoviridae family (Mertens et al., T. Family Reoviridae. 447-454 (Elsevier Academic Press, 2005)). MEGA was used to produce phylogenetic trees, reconstructed through the Neighbor Joining (NJ) method. The statistical significance of a particular tree topology was evaluated by bootstrap re-sampling of the sequences 1000 times.

Consistent with the genome organization characteristic for members of the family Reoviridae, the genome of the PRV comprises at least 10 RNA segments (GenBank Accession numbers GU994013-GU994022). Reoviruses are non-enveloped icosahedral viruses with double-stranded RNA genomes comprising 10-12 segments. Twelve genera are defined based on host range, number of genome segments, G/C content, and antigenic relationships. A phylogenetic tree constructed using L gene segment sequences of known reoviruses indicate that PRV represents a distinct genetic lineage branching off the root of the aquareovirus and orthoreovirus genera, viruses of fish and shellfish, reptiles, birds and mammals (FIG. 2). Analysis of all ten PRV gene segments confirmed the divergence of PRV sequence with respect to other Reoviruses (FIGS. 5 to 12). All PRV gene segments contained the 3' terminal nucleotides (UCAUC-3') found in orthoreoviruses and aquareoviruses (Attoui et al., J Gen Virol 83, 1941-1951 (2002)); however, the 5' terminal nucleotides (5'-GAUAAA/U) were unique.

Figure 13:
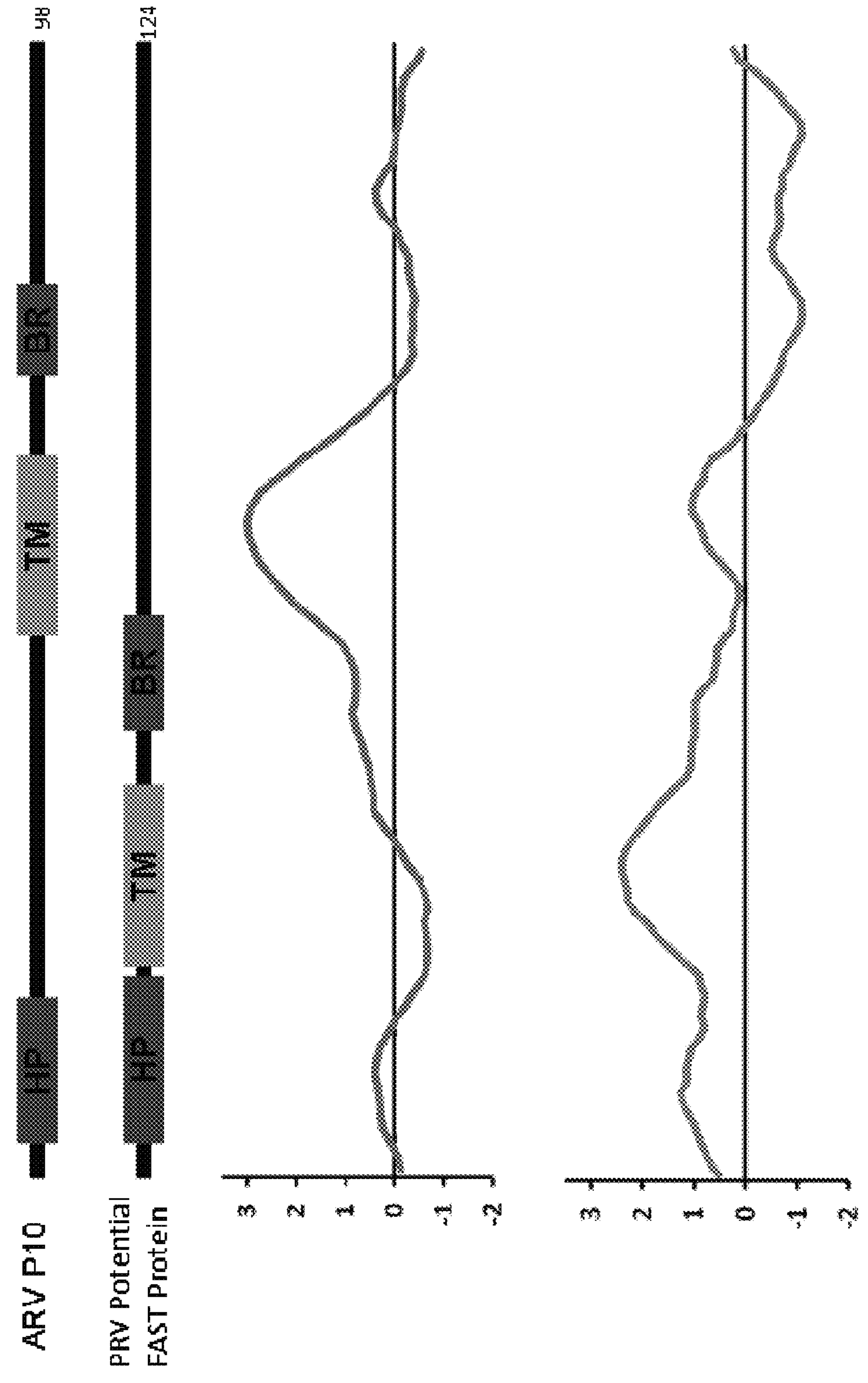
FIG. 13. Putative ORF of S1 has characteristics similar to FAST proteins. Hydrophobicity plots of ARV (red) and PRV (blue) obtained using the Kyle-Doolittle algorithm implemented in the program TopPred. Sequence analysis show that PRV contains the primary components of a FAST protein: hydrophobic region (HP), transmembrane domain(.TM.) and basic region (BR).
Figure 14:
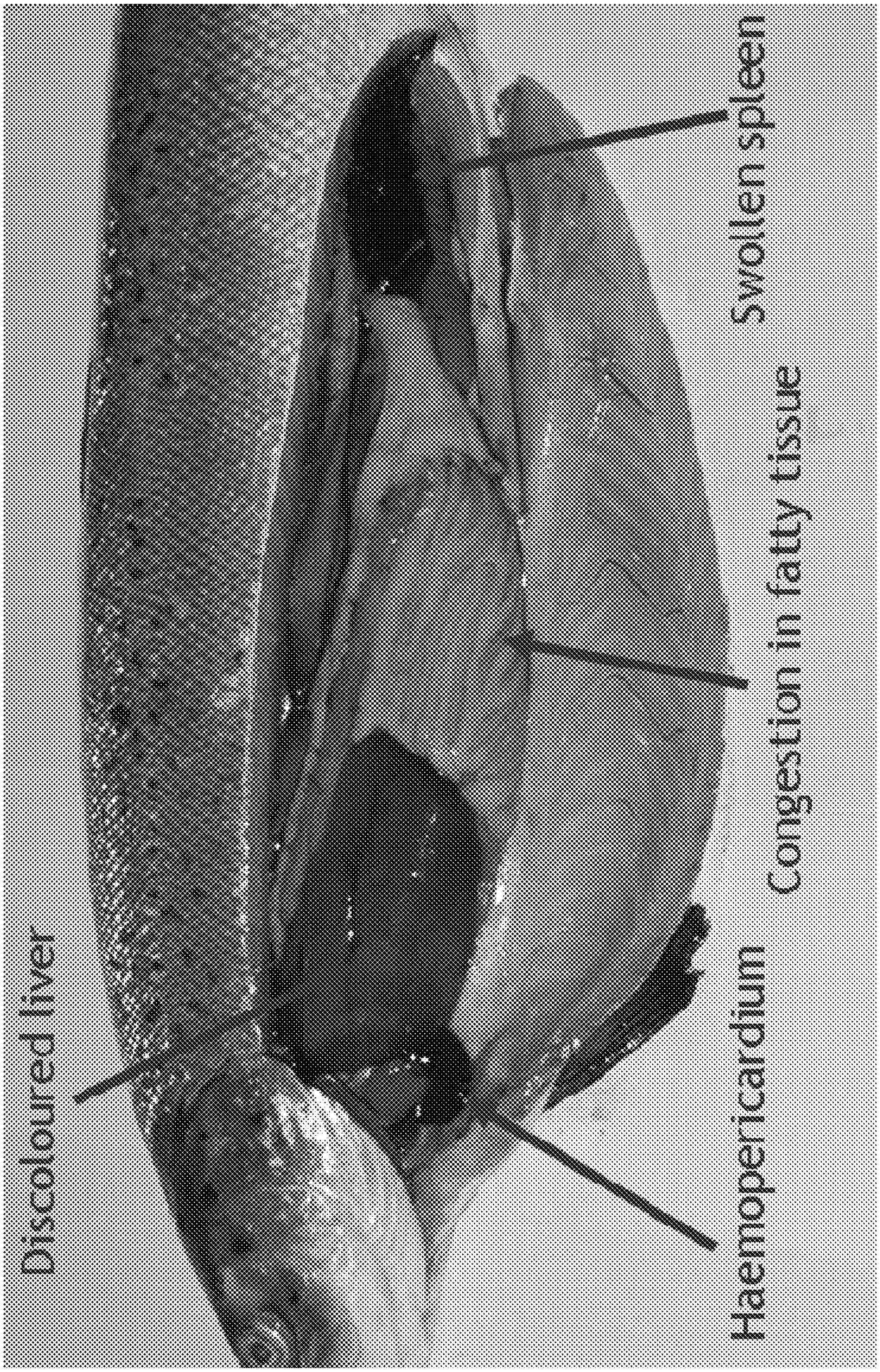
FIG. 14. The pathology of PRV infection can include liver discoloration, heamopericardium, congestion in fatty tissue and swollen spleen.
Figure 15:
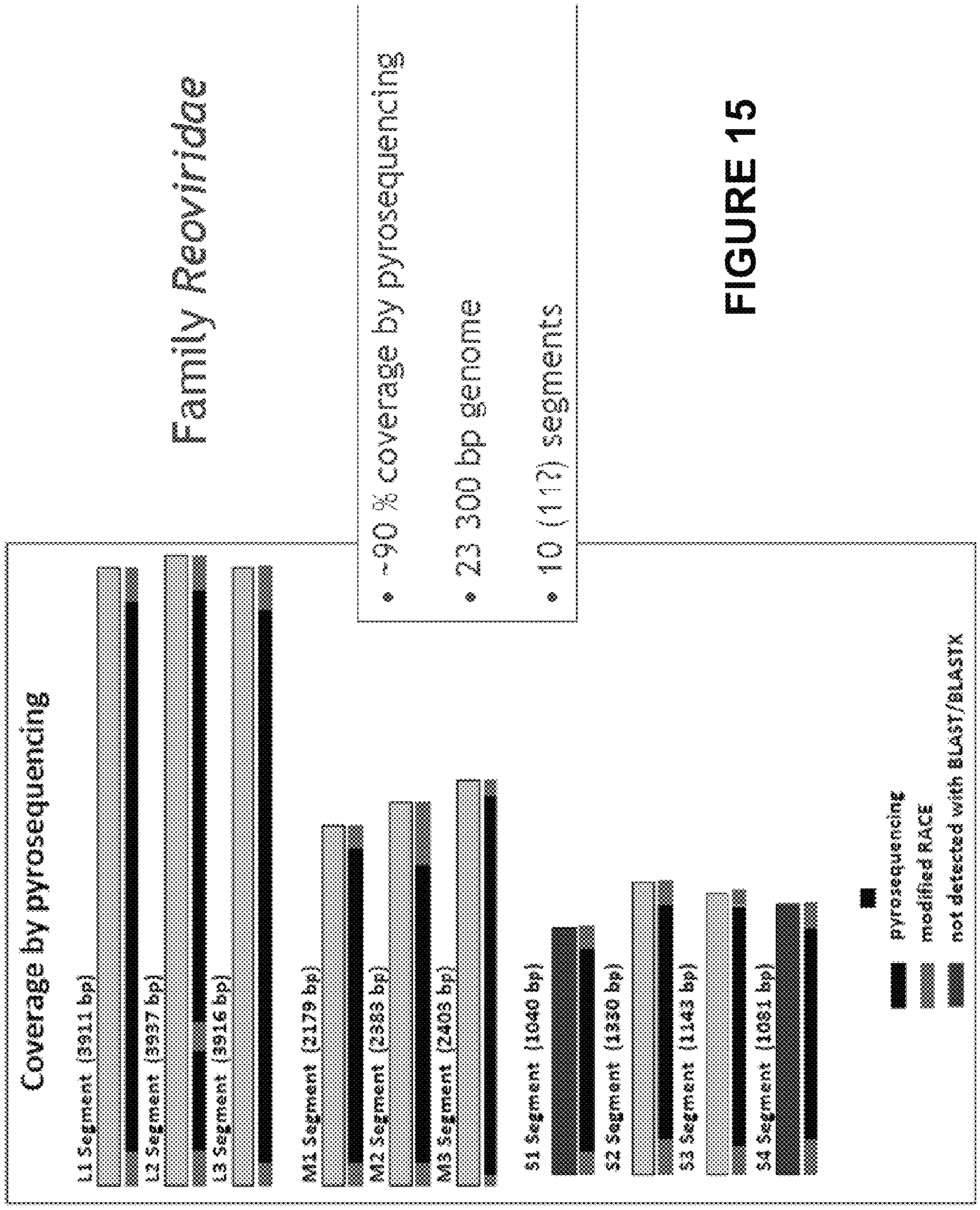
FIG. 15. Coverage by pyrosequencing.
Figure 16:
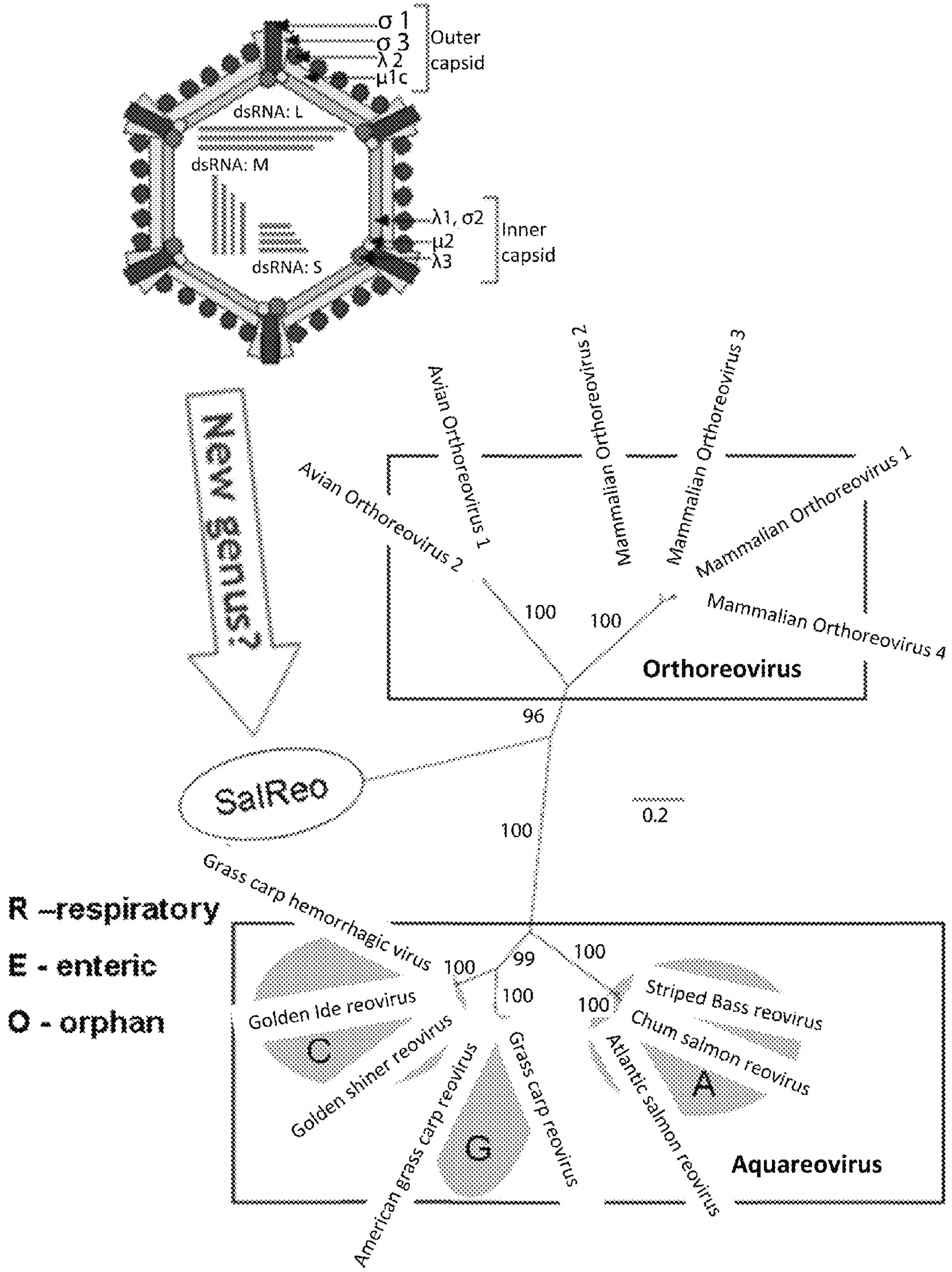
FIG. 16. Phylogenetic analysis of PRV, Orthoreovirus and Aquareovirus.
Figure 17:
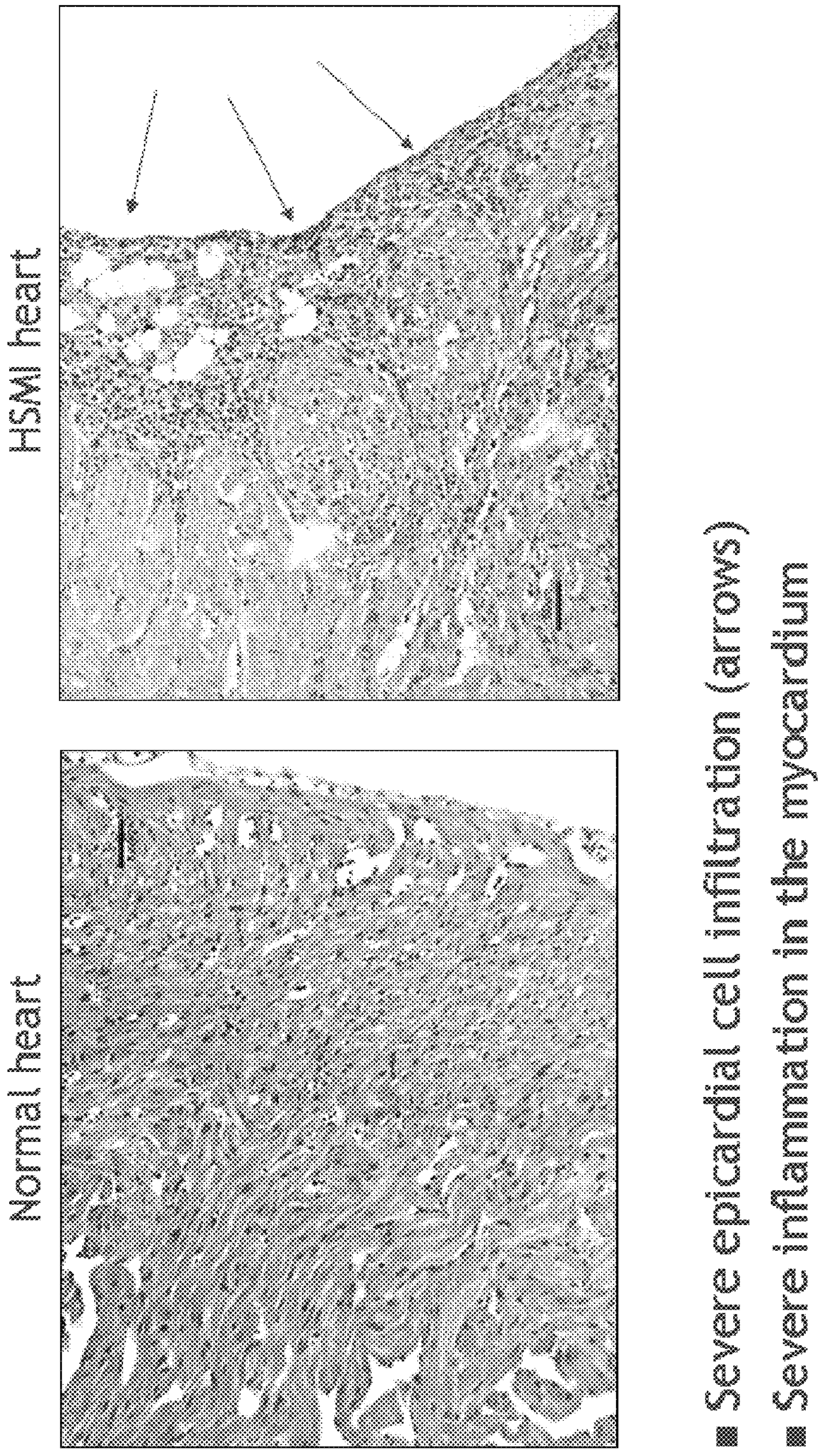
FIG. 17. Diagnosis of HSMI showing infiltration of the epicardium as well as severe inflammation of the myocardium.
Figure 18A:
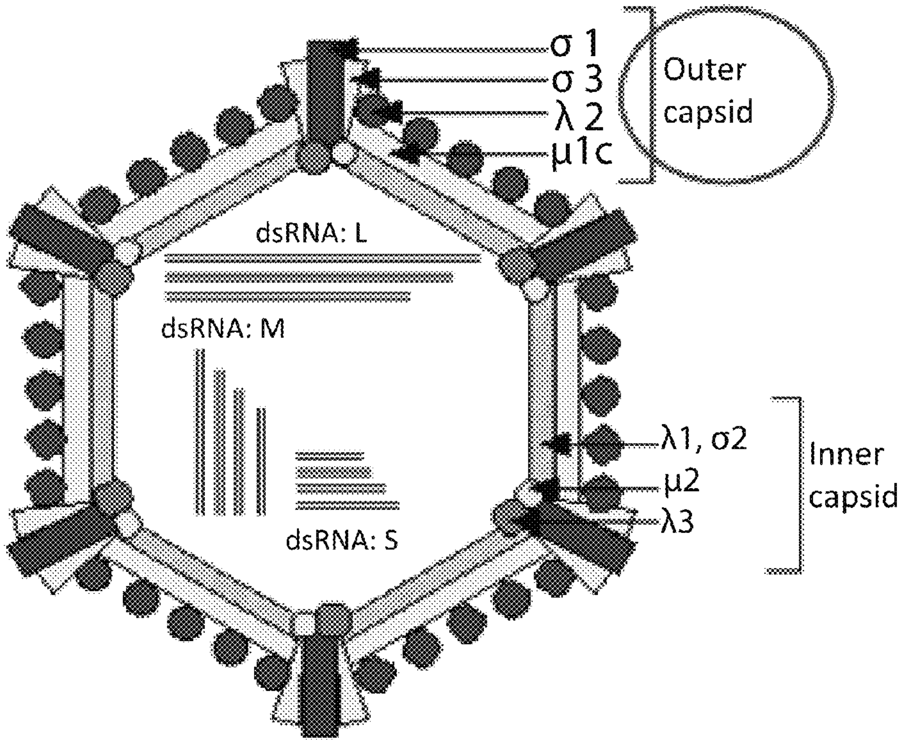
FIG. 18A shows outer capsid proteins σ1, σ3, λ2, μ1c and inner capsid proteins λ1, σ2, μ2, and λ3.
Figure 18B:
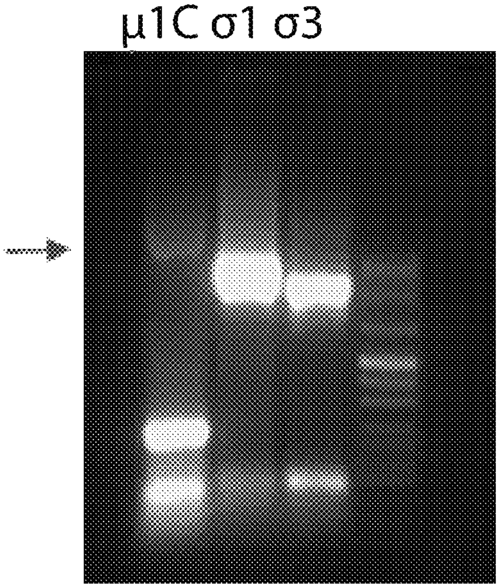
FIG. 18B shows amplification of σ1, σ3 and μ1C full length segments by PCR.
Figure 18C:
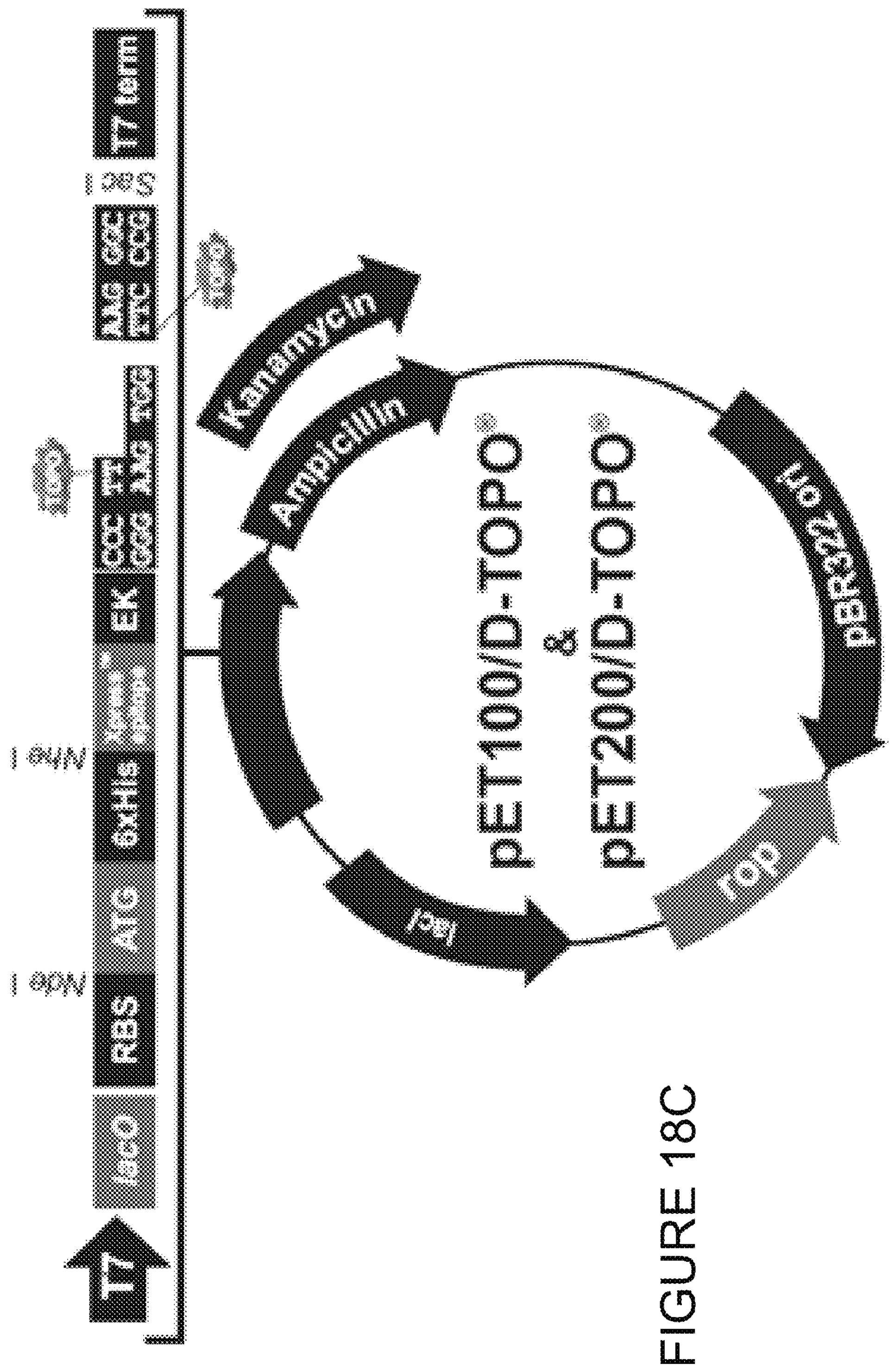
FIG. 18C shows that the amplified segments can be cloned into an expression vector to make an expression construct. The expression can be used to express antigens in an expression system (e.g. *E. coli*). The antigens can then be purified and used to immunize rabbits.
Figure 19A:
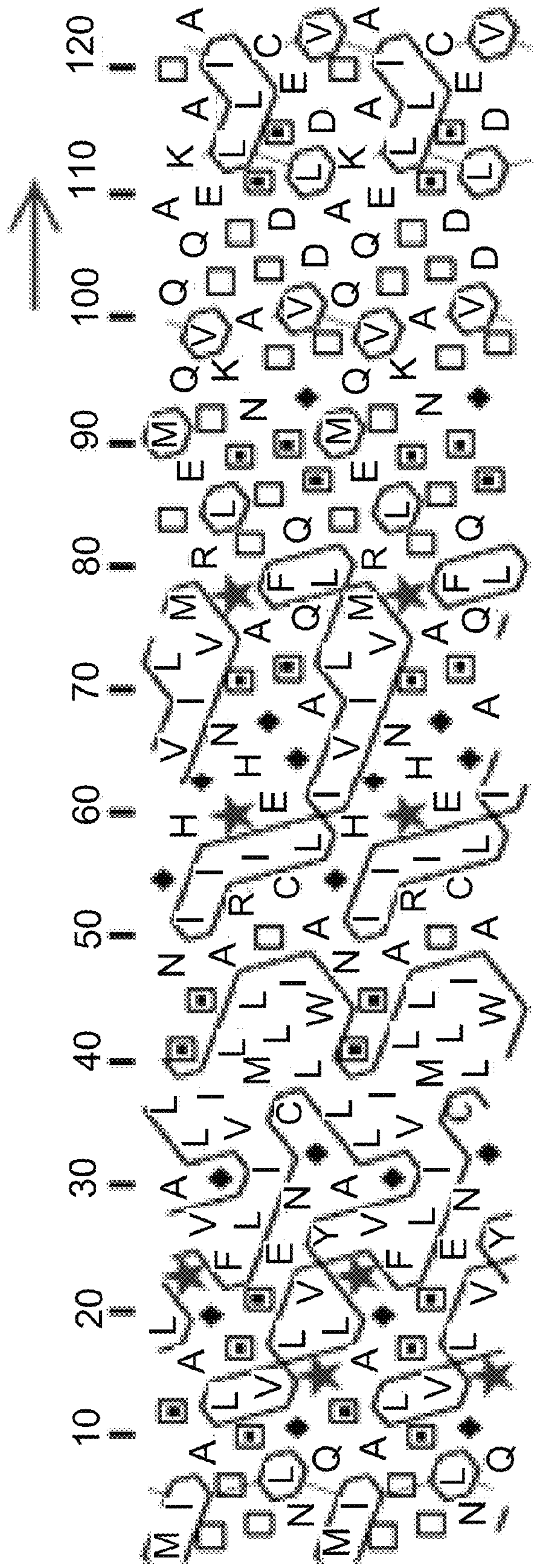
FIG. 19A shows FAST (fusion-associated small transmembrane protein encoded by S4.
Figure 19B:
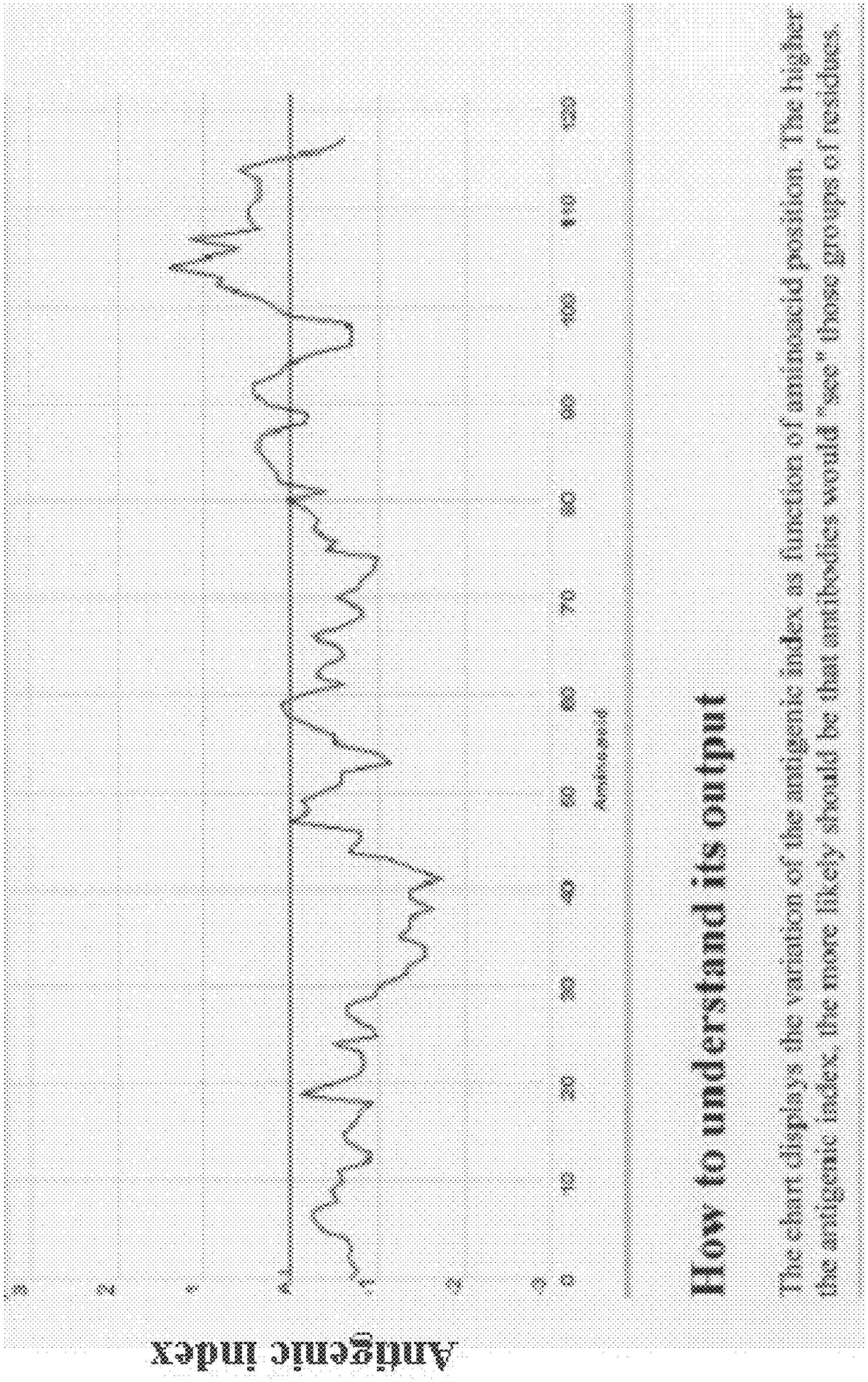
FIG. 19B shows the variation of the antigenic index as a function of amino acid position. The higher the antigenic index, the more likely should be that antibodies would "see" those groups of residues.

The orthoreoviruses have polycistronic segments in either S1 or S4. Whereas aquareovirus species C are polycistronic in the S7 (the orthoreovirus S1 homolog), the other aquareovirus species are not (Attoui et al., J Gen Virol 83, 1941-1951 (2002)). PRV has a putative open reading frame (ORF) in the 5'-end of S2 (71 aa, pI=8.8, 8 kDa), and a putative ORF in 5'-end of S1 (124 aa, pI=4.8, 13 kDa). Although homologues of the λ1, λ2, λ3, μ1, μ2, μ3, σ2 and σNS sequences of PRV are found in orthoreoviruses and aquareoviruses, the σ1 and σ3 sequences and the small putative open reading frames observed in S2 and S1 appear distinctive. The structure of the latter is similar to a fusion-associated small transmembrane (FAST) reovirus protein (Shmulevitz et al., EMBO J 19, 902-912 (2000)) (FIG. 13). Reovirus FAST proteins are nonstructural, single-pass membrane proteins that induce cell-cell fusion and syncytium formation (Shmulevitz et al., EMBO J 19, 902-912 (2000)). Taken together these data provide compelling evidence that PRV is the prototype of a new reovirus genus equally distant to the orthoreovirus and aquareovirus genera.

Figures 3A, 3B:
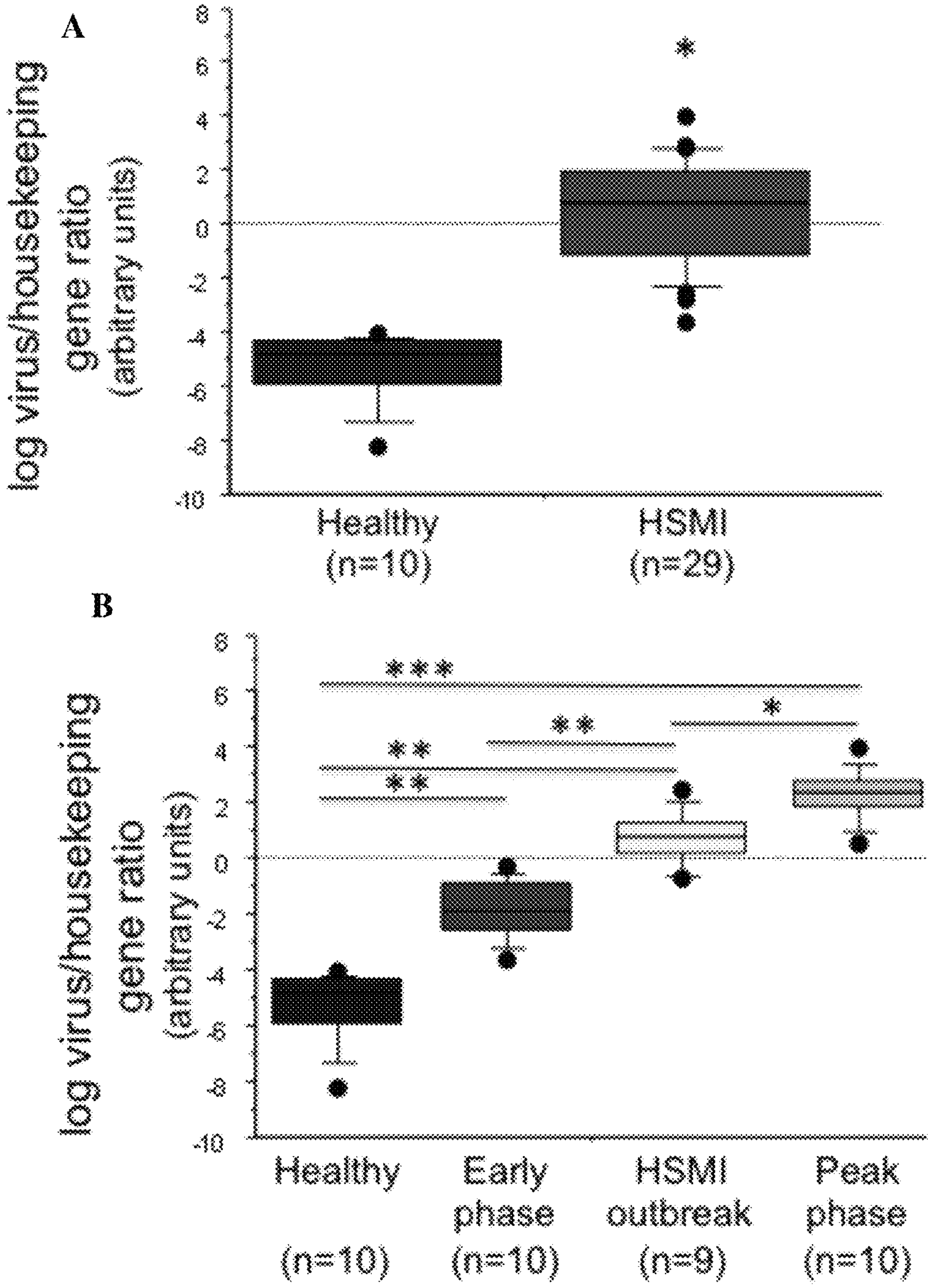
FIG. 3A shows a comparison of adjusted log ratio in mixed heart and kidney samples from healthy farmed fish and farmed fish with HSMI; *, $p<0.0001$ (Mann-Whitney U).
FIG. 3B shows a comparison of adjusted log ratios in farmed fish without HSMI (healthy farmed fish), in the early phase of an HSMI outbreak, in the middle of an HSMI outbreak, and during the peak of an HSMI outbreak; **, $p<0.0005$; *, $p<0.01$ (individual Mann-Whitney U). Adjusted log ratios also differed significantly across all four farmed fish groups ($p<0.0001$; Kruskal-Wallis).

The prevalence of PRV infection in farmed and wild salmon was examined using real time PCR assays targeting genome segments L1, L2, M3 and S4. Levels of viral RNA were quantitated using an MGB assay against L1 wherein results were normalized to elongation factor 1A (EF1A) using the formula by Pfaffl (Pfaffl et al., Nucleic Acids Res 29, e45 (2001)). Heart and kidney samples from 29 salmon representing three different HSMI outbreaks were studied (Table 1) and 10 samples from healthy farmed fish. Twenty-eight of the 29 (96.5%) known HSMI samples and none of the 10 (0%) healthy salmon samples were positive as defined by L1/EF1A gene log ratio ≥5.00. Only one of 29 HSMI samples was negative; this sample originated from a salmon net harboring fish in the early phase of HSMI, prior to the onset of fish mortality (FIG. 3). In fish with signs of severe disease, including abnormal swimming behavior, anorexia and histologic evidence of pancarditis and myositis (Kongtorp et al., J Fish Dis 29, 233-244 (2006)), the median adjusted L1/EF1A gene log ratio was 10.36 (IQR, 0.94). The L1/EF1A gene log ratio was correlated not only with the presence or absence of HSMI, but also, with severity of disease at the time of sampling. The log ratios were lowest in healthy farmed salmon (log ratio range, −0.23 to 3.89; n=10), higher in salmon collected in the early phase of an HSMI outbreak (range, 4.34 to 7.66; n=10), and highest in salmon obtained at the peak of an HSMI outbreak (range, 8.52 to 11.90; n=10). To study the prevalence and relative levels of PRV in healthy wild salmon from different geographic locations, 66 samples obtained from nine coastal rivers in Norway were tested. PRV was detected in only sixteen of these samples (24.2%). Two of these sixteen samples were positive by the cutoff established for farmed salmon with relative log ratios of 6.70 and 7.58; the other fourteen had L1/EF1A log ratios well below the 5.00 cutoff (range, −0.20 to 4.57). No PRV transcripts were detected in any of the remaining wild salmon samples (n=50).

TABLE 1

Viral burden data.

| Sample ID | Fish type | Disease status | Outbreak group/ disease phase | Tissue | L1/EF1A gene ratio (adjusted)[a] | log L1/EF1A gene ratio[b] | Virus detection[c] | Positive/ negative (min = 5.00)[d] |
|---|---|---|---|---|---|---|---|---|
| 408-1 | Farmed | HSMI | Farmed HSMI - peak phase | Heart/ kidney | 3.3E+08 | 8.52 | + | Positive |

TABLE 1-continued

Viral burden data.

| Sample ID | Fish type | Disease status | Outbreak group/ disease phase | Tissue | L1/EF1A gene ratio (adjusted)[a] | log L1/EF1A gene ratio[b] | Virus detection[c] | Positive/ negative (min = 5.00)[d] |
|---|---|---|---|---|---|---|---|---|
| 408-2 | Farmed | HSMI | Farmed HSMI - peak phase | Heart/ kidney | 1.1E+10 | 10.06 | + | Positive |
| 408-3 | Farmed | HSMI | Farmed HSMI - peak phase | Heart/ kidney | 6.4E+09 | 9.80 | + | Positive |
| 408-4 | Farmed | HSMI | Farmed HSMI - peak phase | Heart/ kidney | 1.8E+09 | 9.26 | + | Positive |
| 408-5 | Farmed | HSMI | Farmed HSMI - peak phase | Heart/ kidney | 5.5E+10 | 10.74 | + | Positive |
| 408-6 | Farmed | HSMI | Farmed HSMI - peak phase | Heart/ kidney | 7.1E+09 | 9.85 | + | Positive |
| 408-7 | Farmed | HSMI | Farmed HSMI - peak phase | Heart/ kidney | 6.9E+10 | 10.84 | + | Positive |
| 408-8 | Farmed | HSMI | Farmed HSMI - peak phase | Heart/ kidney | 8.0E+11 | 11.90 | + | Positive |
| 408-9 | Farmed | HSMI | Farmed HSMI - peak phase | Heart/ kidney | 5.2E+10 | 10.71 | + | Positive |
| 408-10 | Farmed | HSMI | Farmed HSMI - peak phase | Heart/ kidney | 4.6E+10 | 10.67 | + | Positive |
| SK300 | Farmed | HSMI | Farmed HSMI outbreak | Heart/ kidney | 2.8E+10 | 10.45 | + | Positive |
| SK301 | Farmed | HSMI | Farmed HSMI outbreak | Heart/ kidney | 1.6E+09 | 9.20 | + | Positive |
| SK302 | Farmed | HSMI | Farmed HSMI outbreak | Heart/ kidney | 1.9E+09 | 9.28 | + | Positive |
| SK303 | Farmed | HSMI | Farmed HSMI outbreak | Heart/ kidney | 1.9E+07 | 7.28 | + | Positive |
| SK304 | Farmed | HSMI | Farmed HSMI outbreak | Heart/ kidney | 2.7E+08 | 8.44 | + | Positive |
| SK305 | Farmed | HSMI | Farmed HSMI outbreak | Heart/ kidney | 2.6E+07 | 7.42 | + | Positive |
| SK306 | Farmed | HSMI | Farmed HSMI outbreak | Heart/ kidney | 5.6E+08 | 8.75 | + | Positive |
| SK307 | Farmed | HSMI | Farmed HSMI outbreak | Heart/ kidney | 5.9E+08 | 8.77 | + | Positive |
| SK308 | Farmed | HSMI | Farmed HSMI outbreak | Heart/ kidney | 2.0E+09 | 9.29 | + | Positive |
| 562-1 | Farmed | HSMI | Farmed HSMI - early phase | Heart/ kidney | 1.4E+06 | 6.14 | + | Positive |
| 562-2 | Farmed | HSMI | Farmed HSMI - early phase | Heart/ kidney | 1.5E+06 | 6.16 | + | Positive |

TABLE 1-continued

Viral burden data.

| Sample ID | Fish type | Disease status | Outbreak group/ disease phase | Tissue | L1/EF1A gene ratio (adjusted)[a] | log L1/EF1A gene ratio[b] | Virus detection[c] | Positive/ negative (min = 5.00)[d] |
|---|---|---|---|---|---|---|---|---|
| 562-3 | Farmed | HSMI | Farmed HSMI - early phase | Heart/ kidney | 1.3E+06 | 6.10 | + | Positive |
| 562-4 | Farmed | HSMI | Farmed HSMI - early phase | Heart/ kidney | 9.6E+05 | 5.98 | + | Positive |
| 562-5 | Farmed | HSMI | Farmed HSMI - early phase | Heart/ kidney | 2.2E+04 | 4.34 | + | Negative |
| 562-6 | Farmed | HSMI | Farmed HSMI - early phase | Heart/ kidney | 1.6E+07 | 7.22 | + | Positive |
| 562-7 | Farmed | HSMI | Farmed HSMI - early phase | Heart/ kidney | 4.6E+07 | 7.66 | + | Positive |
| 562-8 | Farmed | HSMI | Farmed HSMI - early phase | Heart/ kidney | 1.5E+05 | 5.18 | + | Positive |
| 562-9 | Farmed | HSMI | Farmed HSMI - early phase | Heart/ kidney | 2.8E+05 | 5.44 | + | Positive |
| 562-10 | Farmed | HSMI | Farmed HSMI - early phase | Heart/ kidney | 1.2E+07 | 7.07 | + | Positive |
| PD 3511 | Farmed | Healthy | Farmed healthy | Heart/ kidney | 7.6E+02 | 2.88 | + | Negative |
| PD 3512 | Farmed | Healthy | Farmed healthy | Heart/ kidney | 1.2E+02 | 2.07 | + | Negative |
| PD 3513 | Farmed | Healthy | Farmed healthy | Heart/ kidney | 2.5E+03 | 3.41 | + | Negative |
| PD 3514 | Farmed | Healthy | Farmed healthy | Heart/ kidney | 7.9E+03 | 3.90 | + | Negative |
| PD 3515 | Farmed | Healthy | Farmed healthy | Heart/ kidney | 4.8E+03 | 3.68 | + | Negative |
| PD 3516 | Farmed | Healthy | Farmed healthy | Heart/ kidney | 4.2E+01 | 1.62 | + | Negative |
| PD 3517 | Farmed | Healthy | Farmed healthy | Heart/ kidney | 4.5E+03 | 3.65 | + | Negative |
| PD 3518 | Farmed | Healthy | Farmed healthy | Heart/ kidney | 5.8E−01 | −0.23 | + | Negative |
| PD 3519 | Farmed | Healthy | Farmed healthy | Heart/ kidney | 1.1E+03 | 3.02 | + | Negative |
| PD 3520 | Farmed | Healthy | Farmed healthy | Heart/ kidney | 2.1E+03 | 3.32 | + | Negative |
| SF/08 350 | Wild | Healthy | Wild healthy | Heart | — | — | − | Negative |
| SF/08 351 | Wild | Healthy | Wild healthy | Heart | 4.5E+02 | 2.66 | + | Negative |
| SF/08 353 | Wild | Healthy | Wild healthy | Heart | — | — | − | Negative |
| SF/08 354 | Wild | Healthy | Wild healthy | Heart | 5.0E+02 | 2.7 | + | Negative |
| SF/08 315 | Wild | Healthy | Wild healthy | Heart | — | — | − | Negative |
| SF/08 316 | Wild | Healthy | Wild healthy | Heart | — | — | − | Negative |
| SF/08 319 | Wild | Healthy | Wild healthy | Heart | — | — | − | Negative |
| SF/08 321 | Wild | Healthy | Wild healthy | Heart | — | — | − | Negative |
| SF/08 325 | Wild | Healthy | Wild healthy | Heart | — | — | − | Negative |

TABLE 1-continued

Viral burden data.

| Sample ID | Fish type | Disease status | Outbreak group/ disease phase | Tissue | L1/EF1A gene ratio (adjusted)[a] | log L1/EF1A gene ratio[b] | Virus detection[c] | Positive/ negative (min = 5.00)[d] |
|---|---|---|---|---|---|---|---|---|
| SF/08 332 | Wild | Healthy | Wild healthy | Heart | — | — | − | Negative |
| SF/08 338 | Wild | Healthy | Wild healthy | Heart | 6.3E−01 | −0.2 | + | Negative |
| SF/08 48 | Wild | Healthy | Wild healthy | Heart | — | — | − | Negative |
| SF/08 50 | Wild | Healthy | Wild healthy | Heart | — | — | − | Negative |
| SF/08 53 | Wild | Healthy | Wild healthy | Heart | — | — | − | Negative |
| SF/08 56 | Wild | Healthy | Wild healthy | Heart | — | — | − | Negative |
| SF/08 60 | Wild | Healthy | Wild healthy | Heart | — | — | − | Negative |
| SF/08 61 | Wild | Healthy | Wild healthy | Heart | 5.0E+03 | 3.7 | + | Negative |
| SF/08 62 | Wild | Healthy | Wild healthy | Heart | — | — | − | Negative |
| SF/08 63 | Wild | Healthy | Wild healthy | Heart | — | — | − | Negative |
| SF/08 64 | Wild | Healthy | Wild healthy | Heart | 3.1E+03 | 3.49 | + | Negative |
| SF/08 432 | Wild | Healthy | Wild healthy | Heart | — | — | − | Negative |
| SF/08 438 | Wild | Healthy | Wild healthy | Heart | — | — | − | Negative |
| SF/08 440 | Wild | Healthy | Wild healthy | Heart | — | — | − | Negative |
| SF/08 442 | Wild | Healthy | Wild healthy | Heart | — | — | − | Negative |
| SF/08 444 | Wild | Healthy | Wild healthy | Heart | 5.1E+02 | 2.71 | + | Negative |
| SF/08 446 | Wild | Healthy | Wild healthy | Heart | — | — | − | Negative |
| SF/08 447 | Wild | Healthy | Wild healthy | Heart | — | — | − | Negative |
| SF/08 452 | Wild | Healthy | Wild healthy | Heart | 3.7E+04 | 4.57 | + | Negative |
| SF/08 453 | Wild | Healthy | Wild healthy | Heart | — | — | − | Negative |
| SF/08 463 | Wild | Healthy | Wild healthy | Heart | — | — | − | Negative |
| SF/08 464 | Wild | Healthy | Wild healthy | Heart | — | — | − | Negative |
| SF/08 477 | Wild | Healthy | Wild healthy | Heart | — | — | − | Negative |
| SF/08 491 | Wild | Healthy | Wild healthy | Heart | — | — | − | Negative |
| SF/08 497 | Wild | Healthy | Wild healthy | Heart | — | — | − | Negative |
| SF/08 508 | Wild | Healthy | Wild healthy | Heart | — | — | − | Negative |
| SF/08 511 | Wild | Healthy | Wild healthy | Heart | — | — | − | Negative |
| SF/08 517 | Wild | Healthy | Wild healthy | Heart | — | — | − | Negative |
| SF/08 518 | Wild | Healthy | Wild healthy | Heart | 1.7E+01 | 1.23 | + | Negative |
| SF/08 519 | Wild | Healthy | Wild healthy | Heart | — | — | − | Negative |
| SF/08 522 | Wild | Healthy | Wild healthy | Heart | — | — | − | Negative |
| SF/08 198 | Wild | Healthy | Wild healthy | Heart | 5.0E+06 | 6.7 | + | Positive |
| SF/08 200 | Wild | Healthy | Wild healthy | Heart | — | — | − | Negative |
| SF/08 201 | Wild | Healthy | Wild healthy | Heart | — | — | − | Negative |
| SF/08 205 | Wild | Healthy | Wild healthy | Heart | — | — | − | Negative |
| SF/08 206 | Wild | Healthy | Wild healthy | Heart | — | — | − | Negative |

TABLE 1-continued

| Viral burden data. | | | | | | | | |
|---|---|---|---|---|---|---|---|---|
| Sample ID | Fish type | Disease status | Outbreak group/ disease phase | Tissue | L1/EF1A gene ratio (adjusted)[a] | log L1/EF1A gene ratio[b] | Virus detection[c] | Positive/ negative (min = 5.00)[d] |
| SF/08 207 | Wild | Healthy | Wild healthy | Heart | — | — | − | Negative |
| SF/08 208 | Wild | Healthy | Wild healthy | Heart | 3.8E+07 | 7.58 | + | Positive |
| SF/08 209 | Wild | Healthy | Wild healthy | Heart | — | — | − | Negative |
| SF/08 210 | Wild | Healthy | Wild healthy | Heart | — | — | − | Negative |
| SF/08 211 | Wild | Healthy | Wild healthy | Heart | — | — | − | Negative |
| 1-13 | Wild | Healthy | Wild healthy | Heart | 1.2E+01 | 1.08 | + | Negative |
| 1-14 | Wild | Healthy | Wild healthy | Heart | — | — | − | Negative |
| 1-21 | Wild | Healthy | Wild healthy | Heart | — | — | − | Negative |
| 1-22 | Wild | Healthy | Wild healthy | Heart | — | — | − | Negative |
| 1-23 | Wild | Healthy | Wild healthy | Heart | — | — | − | Negative |
| 1-24 | Wild | Healthy | Wild healthy | Heart | 1.7E+00 | 0.24 | + | Negative |
| 1 H | Wild | Healthy | Wild healthy | Heart | 5.4E+01 | 1.73 | + | Negative |
| 2 H | Wild | Healthy | Wild healthy | Heart | — | — | − | Negative |
| 3 H | Wild | Healthy | Wild healthy | Heart | — | — | − | Negative |
| 1 M | Wild | Healthy | Wild healthy | Muscle | 4.0E+01 | 1.6 | + | Negative |
| 2 M | Wild | Healthy | Wild healthy | Muscle | — | — | − | Negative |
| 3 M | Wild | Healthy | Wild healthy | Muscle | 1.7E+02 | 2.23 | + | Negative |
| 1 Mi | Wild | Healthy | Wild healthy | Spleen | — | — | − | Negative |
| 2 Mi | Wild | Healthy | Wild healthy | Spleen | — | — | − | Negative |
| 3 Mi | Wild | Healthy | Wild healthy | Spleen | — | — | − | Negative |
| 521-6 | Wild | Healthy | Wild healthy | Various organs | 2.7E+00 | 0.42 | + | Negative |

[a]= Ratio of virus burden (quantitated through the L1 viral gene), normalized using a salmon housekeeping gene (EF1A) and adjusted by a factor of 108.
[b]= Log transformation of the adjusted ratio L1/EF1A.
[c]= Virus detection by real time RT-PCR.
[d]= For statistical analyses, samples were considered positive whenever the adjusted log ratio was higher than 5.00

Figures 4A, 4B, 4C, 4D:
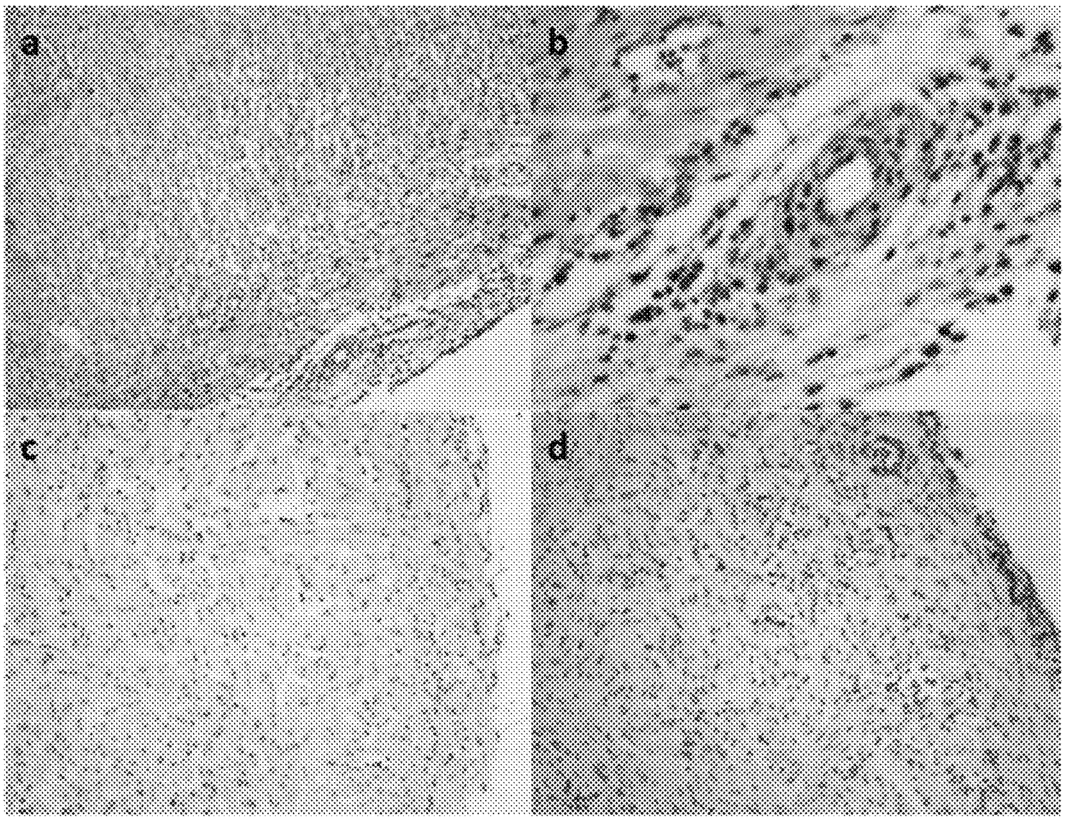
FIG. 4A shows heart from HSMI-infected fish (10×).
FIG. 4B shows heart from HSMI-infected fish (40×).
FIG. 4C shows heart from non-infected fish (40×).
FIG. 4D shows heart from a fish infected with salmon pancreas disease virus.
Figure 5:
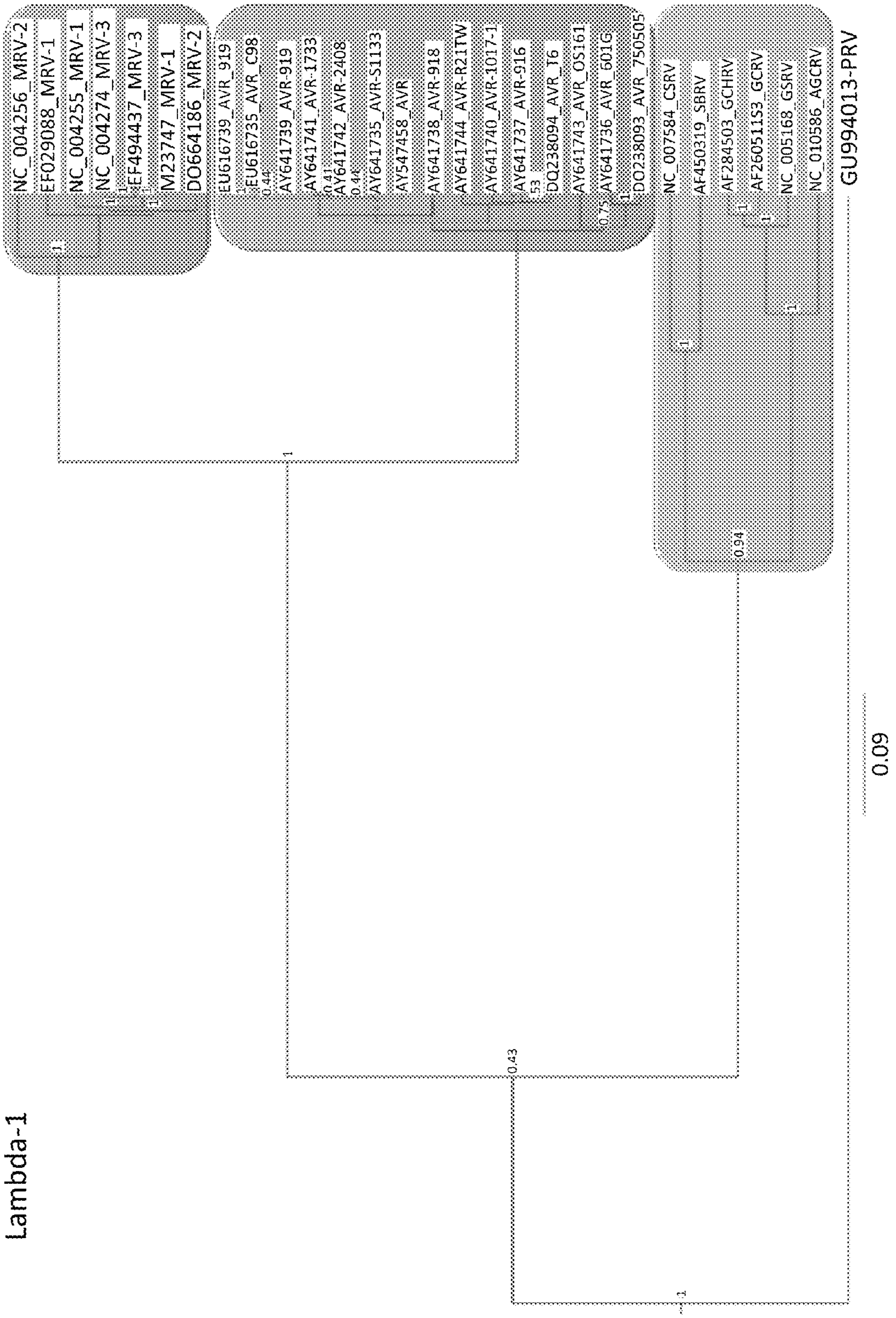
FIG. 5. Phylogenetic analysis of the Lambda-1 ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).
Figure 6:
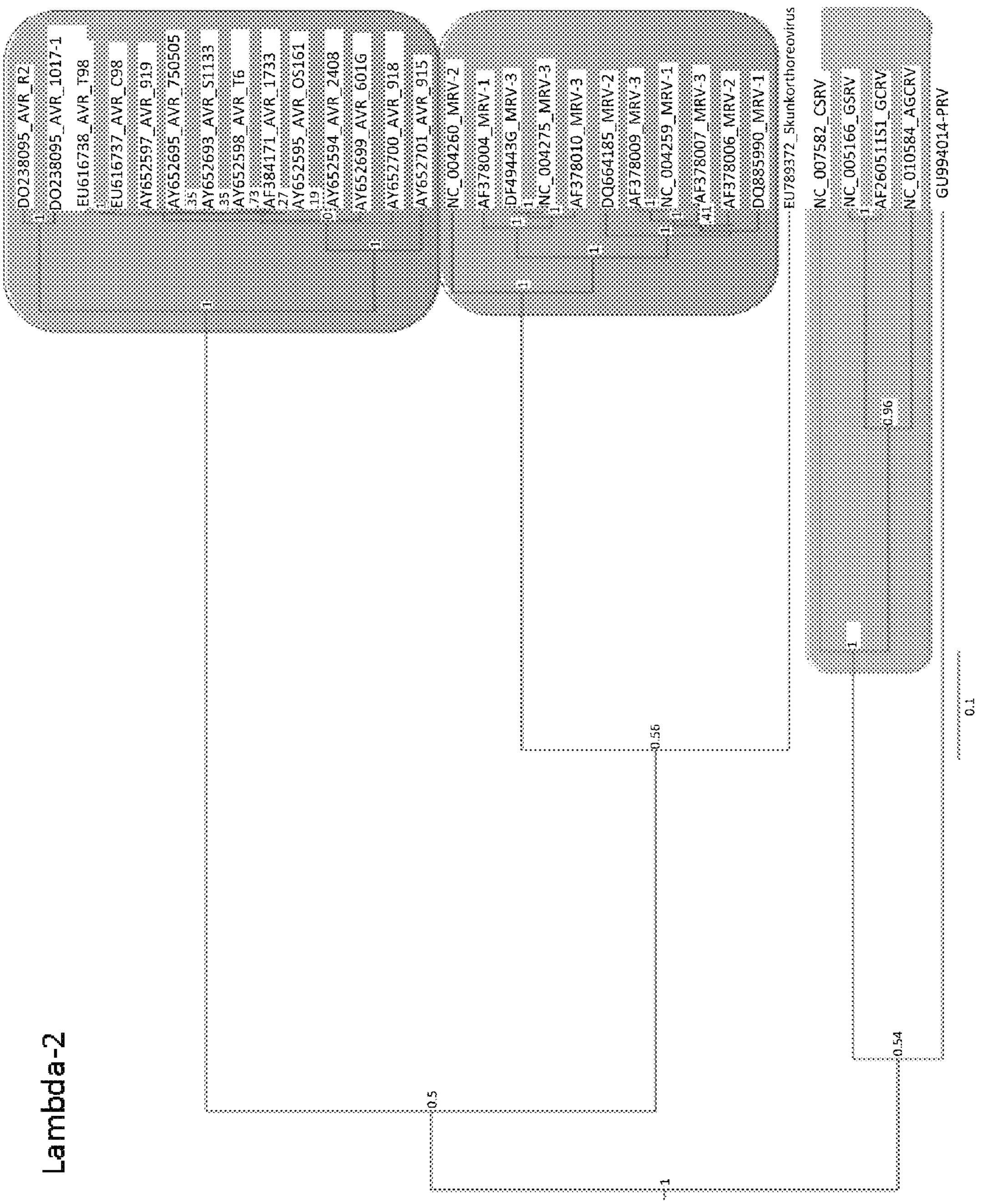
FIG. 6. Phylogenetic analysis of the Lambda-2 ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).
Figure 7:
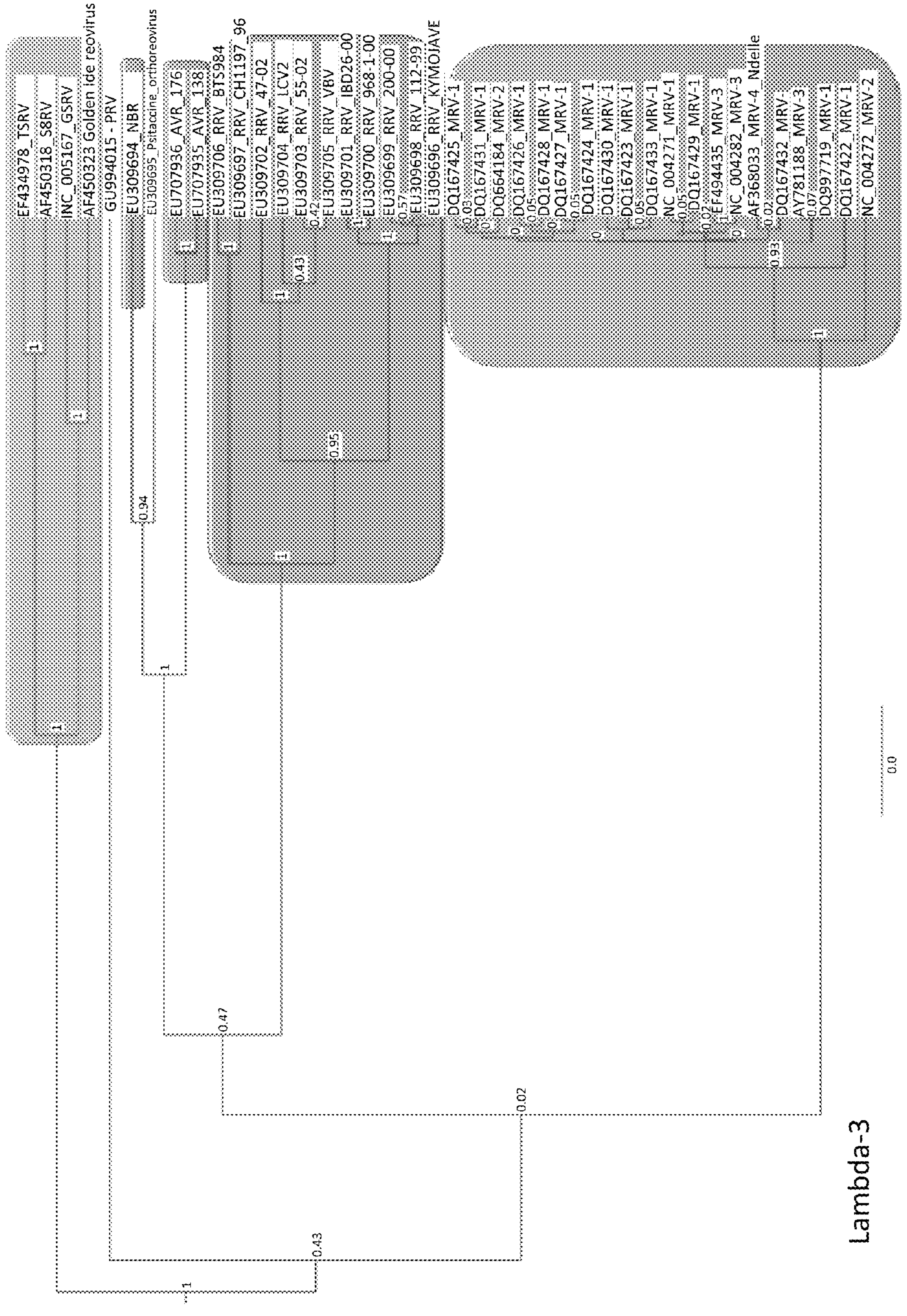
FIG. 7. Phylogenetic analysis of the Lambda-3 ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).
Figure 8:
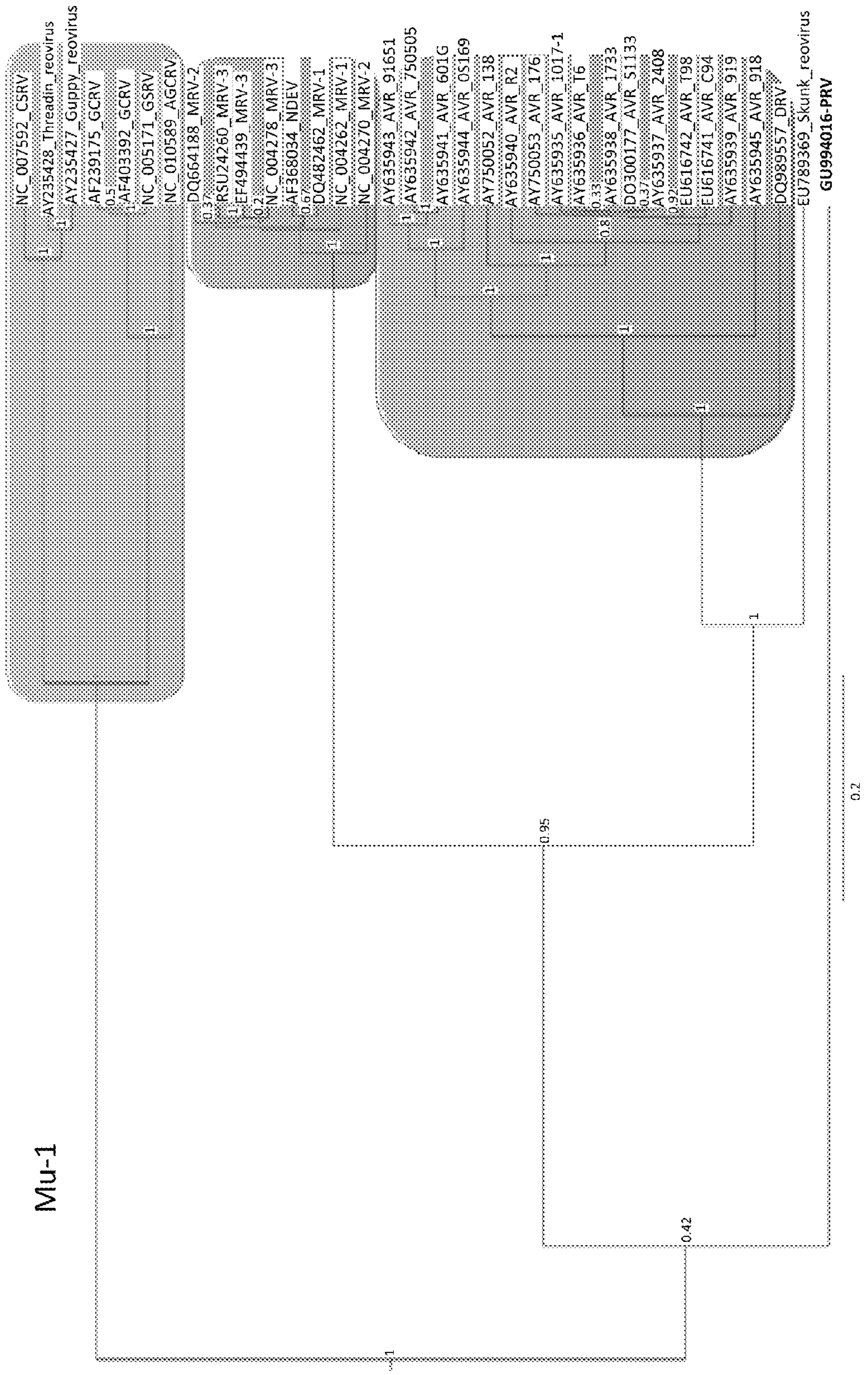
FIG. 8. Phylogenetic analysis of the Mu-1 ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).
Figure 9:
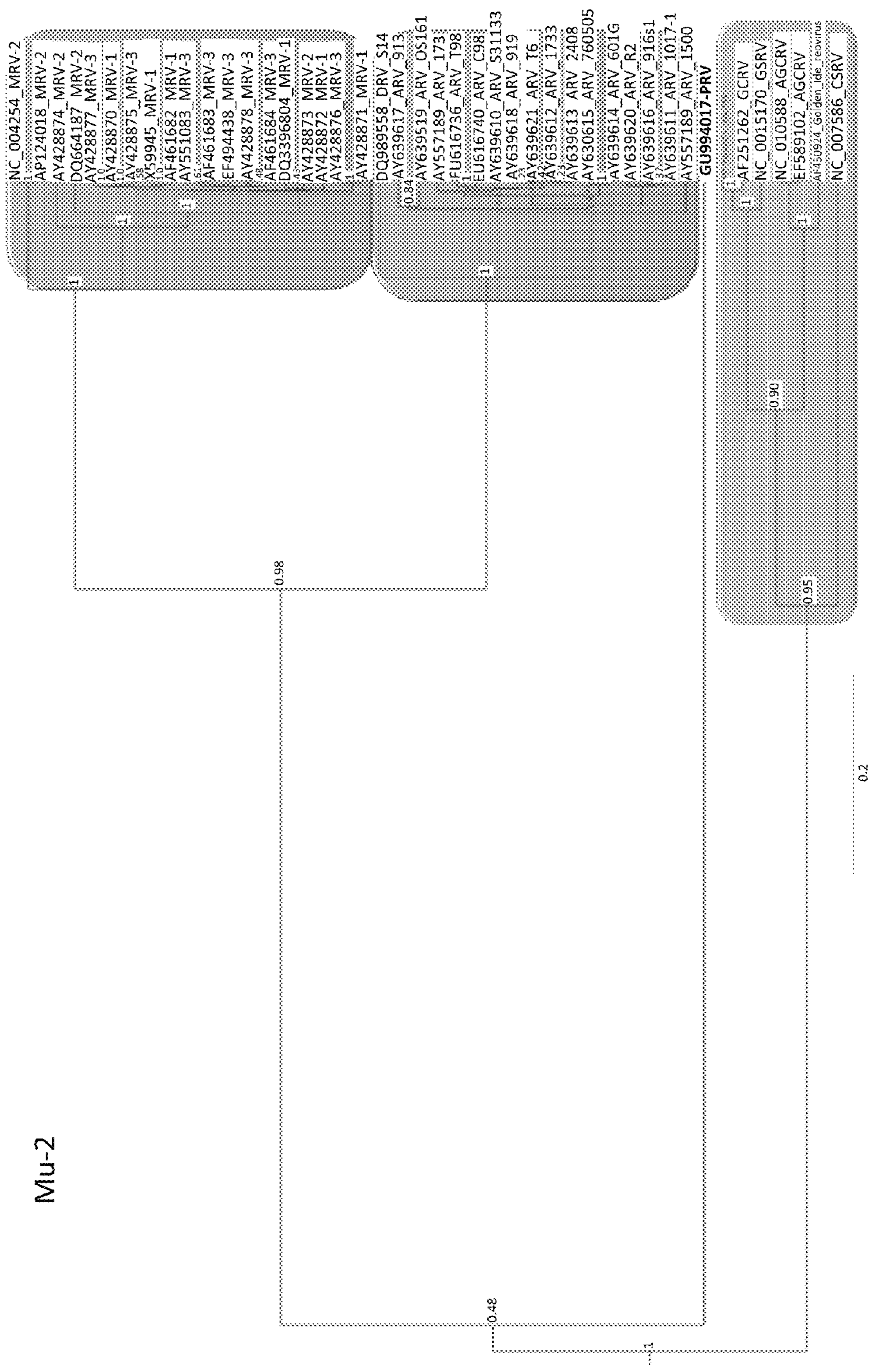
FIG. 9. Phylogenetic analysis of the Mu-2 ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).
Figure 10:
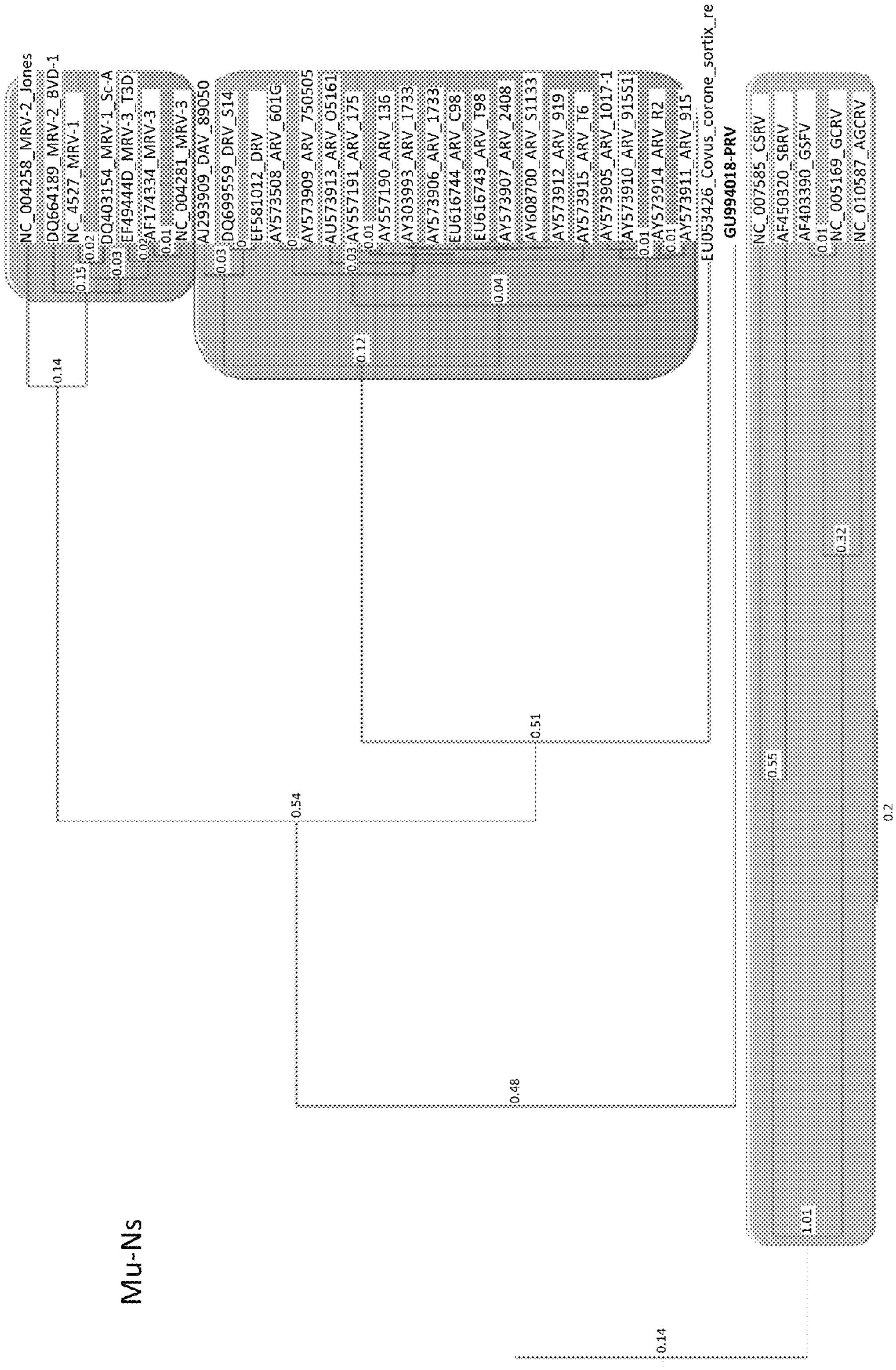
FIG. 10. Phylogenetic analysis of the Mu-3 ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).
Figure 11:
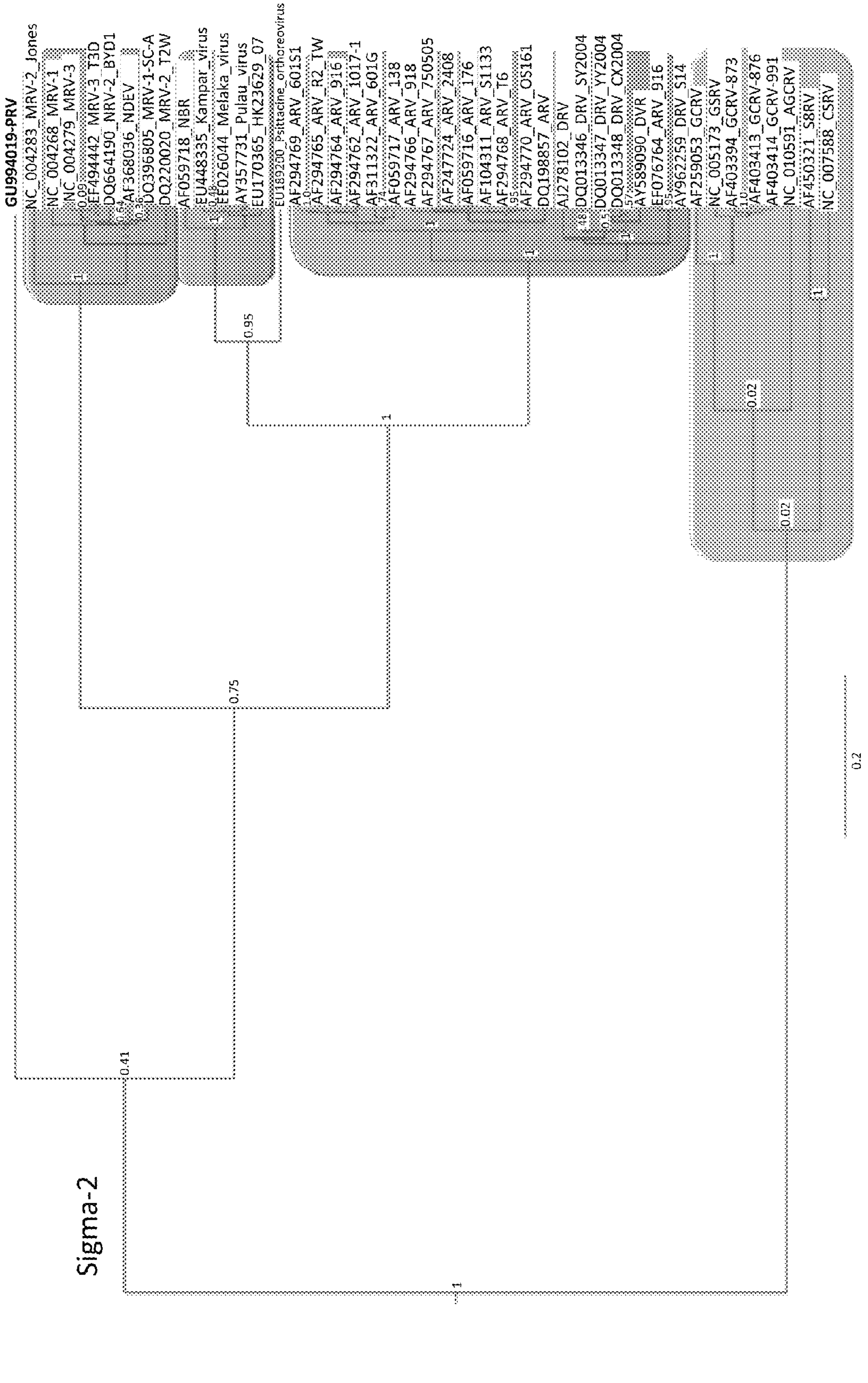
FIG. 11. Phylogenetic analysis of the Sigma-2 ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).
Figure 12:
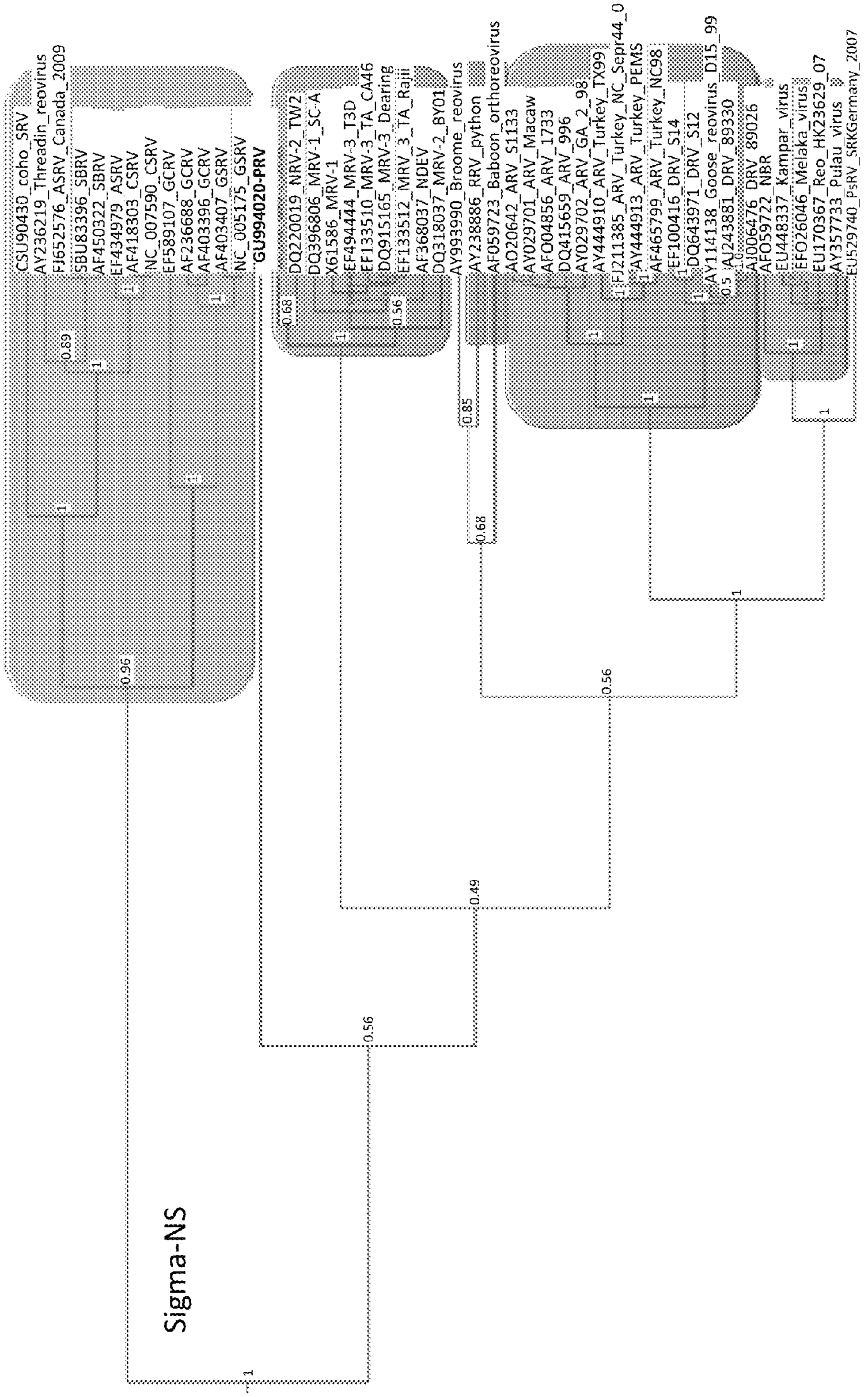
FIG. 12. Phylogenetic analysis of the Sigma-NS ORF of the Aquareovirus and Orthoreovirus. Bayesian phylogenetic analyses of sequence differences among segments λ1, λ2, λ3, μ1, μ2, μ3, σ2 and σNS (σ1 and σ3 of aquareovirus and orthoreovirus had different genomic organizations) were conducted using BEAST, BEAUti and Tracer analysis software packages. Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states. Colored boxes indicate representatives of different reovirus genera or species. Green, Aquareovirus genus; blue, species I (mammalian orthoreovirus); red, species II (avian orthoreovirus); purple, species III (Nelson Bay orthoreovirus); orange, species IV (reptilian orthoreovirus) and light blue, species V (Baboon orthoreovirus).

The anatomic distribution of PRV in relation to pathology was tested through in situ hybridization using probes to L2 gene RNA. PRV RNA was distributed throughout the myocardium and endocardium of salmon with HSMI (FIG. 4A, 4B) but not detected in normal salmon or salmon infected with salmon pancreas disease virus (FIG. 4C, 4D)

Implication of a microbe in a disease via Koch's postulate requires demonstration that an agent is specific for that disease, and that disease can be reproduced in a naïve host by inoculation with the agent propagated in culture following isolation from an affected host. Although fulfillment of this postulate is compelling evidence of causation the criteria are unduly stringent. Some agents cannot be cultured. Additionally, genetic and other factors may contribute to pathogenesis. PRV has not been cultured. Furthermore, PRV has been found in farmed fish that do not show clinical signs of HSMI. Moreover, PRV has been also detected in low quantities in wild Atlantic salmon. Nonetheless, the tissue distribution and load of PRV are correlated with disease in naturally and experimentally infected salmon. Analogies between commercial poultry production and Atlantic salmon aquaculture may be informative Reoviruses are also implicated in numerous diseases of poultry, including enteritis, myocarditis, and hepatitis (Jones, Rev Sci Tech 19, 614-625 (2000)). Both poultry production and aquaculture confine animals at high density in conditions that are conducive to transmission of infectious agents and may reduce resistance to disease by induction of stress.

Unlike terrestrial animal farming, where contact between domestic and free ranging wild animals of the same or closely related species is easily monitored and controlled, ocean based aquaculture is an open system wherein farmed fish may incubate and transmit infectious agents to already diminishing stocks of wild fish. PRV will be isolated in cell culture and prevention or modification of the disease will be performed disease through use of specific drugs or vaccines. Nonetheless, the results described herein show that a causal relationship can exists, measures to control PRV can be undertaken because PRV threatens domestic salmon production and also has the potential for transmission to wild salmon populations.

Example 3

PRV Identification and Sequencing

HSMI was experimentally-induced in normal Atlantic salmon by inoculation with heart and kidney extracts from fish with HSMI or cohabitation with fish with HSMI. RNA extracted from heart tissue from Atlantic salmon with experimentally-induced HSMI was used as template for high throughput pyrosequencing. Sequences were analyzed using a suite of bioinformatic applications available at the GreenePortal website, including FASD, a method whereby the statistical distribution of oligonucleotide frequencies within an unknown sequence set is compared to frequencies calculated for known sequence sets. Seven of ten segments of a novel reovirus, piscine reovirus (PRV), were identified using alignment and a motif-based program; three additional segments were identified using FASD. Quantitative real time PCR assays of samples from fish collected during outbreaks of HSMI and from fish with experimentally-induced HSMI confirmed association between PRV and HSMI. In situ hybridization confirmed the presence of PRV sequences in heart of fish with HSMI.

Identification of PRV by high-throughput sequencing Healthy Atlantic salmon produced at an experimental facility (VESO, Vikan; Namsos, Norway), with an average weight of 50 g were inoculated with cardiac tissue from field outbreaks of HSMI and served as donors for material for the high-throughput sequencing. Non-inoculated fish served as negative controls (Kongtorp and Taksdal, J Fish Dis 32, 253-262 (2009)). Three heart muscle biopsies were diluted 1:10 in HBSS, filtrated through a 0.22 μm filter and inactivated in TRIzol LS reagent. Several serum samples were inactivated directly in TRIzol LS. Total RNA extracts were treated with DNase I and cDNA generated by using the Superscript II system for reverse transcription primed by random octamers that were linked to an arbitrary defined 17-mer primer sequence (Palacios et al., Emerg Infect Dis 13, 73-81 (2007)). The resulting cDNA was treated with RNase H and then randomly amplified by the polymerase chain reaction (PCR); applying a 9:1 mixture of a primer corresponding to the defined 17-mer sequence and the random octamer-linked 17-mer primer, respectively (Palacios et al., Emerg Infect Dis 13, 73-81 (2007)). Products >70 base pairs (bp) were selected by column purification and ligated to specific linkers for sequencing on the 454 Genome Sequencer FLX without fragmentation of the cDNA (Margulies, M. et al., Nature 437, 376-380 (2005); Palacios et al. N Engl J Med 358, 991-998 (2008); Cox-Foster et al., Science 318, 283-287 (2007)).

Removal of primer sequences, redundancy filtering, and sequence assembly were performed with software programs accessible through the analysis applications at the GreenePortal website. When traditional BLASTN, BLASTX and FASTX analysis failed to identify the origin of the sequence read, FASD was applied (Trifonov et al, (submitted)), a novel method based on the statistical distribution of oligonucleotide frequencies. The probability of a given segment to belong to a class of viruses is computed from their distribution of oligonucleotide frequencies in comparison with the calculated for other segments. A statistic measure was developed to assess the significance of the relation between segments. The p-value estimates the likelihood that an oligonucleotide distribution is derived from a different one. Thus, highly related distributions present a high p-value.

Conventional PCRs were performed with HotStar polymerase on PTC-200 thermocyclers an enzyme activation step of 5 min at 95° C. was followed by 45 cycles of denaturation at 95° C. for 1 min, annealing at 55° C. for 1 min, and extension at 72° C. for 1 to 3 min depending on the expected amplicon size. Amplification products were run on 1% agarose gels, purified and directly sequenced in both directions with ABI PRISM Big Dye Terminator 1.1 Cycle Sequencing kits on ABI PRISM 3700 DNA Analyzers.

Example 4

Sequence Analyses

Programs of the Geneious package (Biomatters, New Zealand) were used for sequence assembly and analysis. Sequences were downloaded from GenBank and aligned using the ClustalX (Thompson et al., Curr Protoc Bioinformatics Chapter 2, Unit 23 (2002)) implementation on the MEGA software (Tamura et al., Mol Biol Evol 24, 1596-1599 (2007)). The amino acid alignments obtained were further refined using T-Coffee (Notredame et al., J Mol Biol 302, 205-217 (2000)) to incorporate protein structure data on the alignment. To evaluate the robustness of the approach, the ability to find and align motifs previously identified as conserved among Reoviridae was used as a marker. Phylogenetic analysis were performed using p-distance as model of amino acid substitution as accepted by ICTV for analysis of the Reoviridae family. MEGA was used to produce phylogenetic trees, reconstructed through the Neighbor Joining (NJ) method.

The statistical significance of a particular tree topology was evaluated by bootstrap resampling of the sequences 1000 times. Bayesian phylogenetic analyses of the sequence differences among segments λ1, λ2, λ3, μ1, μ2, μ3, σ2 and σ3 (σ1 and σNS of aquareovirus and orthoreovirus had different genomic organizations) were conducted using the BEAST, BEAUti and Tracer analysis software packages.

Preliminary analyses were run for 10,000,000 generations with the Dayhoff amino acid substitution model to select the clock and demographic models most appropriate for each ORF. An analysis of the marginal likelihoods indicated that the relaxed lognormal molecular clock and constant population size model was chosen for all datasets. Final data analyses included MCMC chain lengths of 5,000,000-30,000,000 generations, with sampling every 1000 states (FIGS. 5-12).

Example 5

Real Time PCR

Quantitative assays were established based upon virus specific sequences obtained from the high throughput sequencing for several reovirus segments. Six different realtime assays were designed targeting genome fragment L1, L2 and M3 (SYBR green) as well as L1 and S4 (MGB assays) (See Table 2 for a list of the primers). Samples from different organs from experimentally infected fish were positive while samples from non-infected control fish were negative. For further screening, the real-time PCR for segment L1 was performed using the QIAGEN OneStep kit. Six μl of template RNA were denatured (95° C./5 min). Reactions were performed using the following concentrations: 400 nM primer, 300 nM probe and 1.25 mM $MgCl_2$. Amplifications were done in a Stratagene Mx3005P real-time PCR machine (Stratagene) with the following cycle parameters: 30 min at 50° C. (reverse transcription), 15 min at 94° C. (RT inactivation and PCR polymerase activation), 45 cycles of 94° C./15 sec, 54° C./30 sec and 72° C./15 sec. Standard curves were created using RNA pooled from three fish with high viral loads.

Standard curves were made in duplicates for both the MGB assay and the EF1A assay (Olsvik et al., BMC Mol Biol 6, 21 (2005)) and relative viral RNA loads for field samples were calculated by using normalization against EF1A.

TABLE 2

Primers for realtime assays for targeting genome fragment L1, L2 and M3 (SYBR green) as well as L1 and S4.

| Primer name | Assay type | Target segment | Sequence (5'-3') | SEQ ID NO |
|---|---|---|---|---|
| AqureoGT70F | SYBR green | L2 (1577-1561) | AGGATGTATGCCACTAGCTCC | SEQ ID NO: 11 |
| AqureoGT70R | SYBR green | L2 1513-1536) | GCTGGTAACTGGCTTACTGCTAAT | SEQ ID NO: 12 |
| AquareoHC86F | SYBR green | L1 (3832-3810) | ATGTCACAACTTGAGTCAGTTCC | SEQ ID NO: 13 |
| AquareoHC86R | SYBR green | L1 (3747-3770) | GATACAGCTACCCAACATGATTGA | SEQ ID NO: 14 |
| AquareoNS86F | SYBR green | M3 (2119-2096) | TCAGTGCGGGGAACTCTAGTGGCA | SEQ ID NO: 15 |
| AquareoNS86R | SYBR green | M3 (2025-2048) | GACGACCTTGAACGCACGAGCGTG | SEQ ID NO: 16 |
| Salmon_Reo_F | SYBR green | L2 (1767-1792) | TGCTGGCGATGATCTTGGAGTATGC | SEQ ID NO: 17 |
| Salmon_Reo_R | SYBR green | L2 (1908-1935) | ACACCATCAGTGAACTTAGGAGCAACA | SEQ ID NO: 18 |
| L1_2671F | MGB assay | L1 (3277-3257) | TGCTAACACTCCAGGAGTCATTG | SEQ ID NO: 19 |
| L1_2729R | MGB assay | L1 (3219-3241) | TGAATCCGCTGCAGATGAGTA | SEQ ID NO: 20 |
| L1 MGB probe | MGB assay | L1 (3243-3256) | FAM - CGCCGGTAGCTCT - MGBNFQ | SEQ ID NO: 21 |
| S4_F1 | MGB assay | S1 (399-417) | ACAGTCGCGGTTCAAACGA | SEQ ID NO: 22 |
| S4_R2 | MGB assay | S1 (460-441) | AAGGCGTCGCTTAGCTTCAA | SEQ ID NO: 23 |
| S4 MGB probe | MGB assay | S1 (419-433) | FAM - AGACCAGACAGACGC - MGBNFQ | SEQ ID NO: 24 |
| ELAF | TAQMAN | Elongation | CCACAGACAAGCCCCTTCGT | SEQ ID NO: 25 |
| ELAR | TAQMAN | factor A | CCTTCAGGGTTCCAGTCTCCA | SEQ ID NO: 26 |
| ELA probe | TAQMAN | | FAM - AGGTACAGTTCCAATACCACCGATTTTGTAAACG - TAMRA | SEQ ID NO: 27 |

Example 6

In Situ Hybridization

In situ hybridization was performed in compliance with the protocol from GeneDetect (Auckland, New Zealand) with some modifications using LNA probes targeting L2. Sections were permeabilized using 40 μg ml-1 Proteinase K in TE buffer at 37° C. for 15 min followed by hybridization with a mixture of two 5' and 3' double DIG labeled LNA probes (5'-CACCATCAGTGAACTTAGGAGCAAC-3' (SEQ ID NO: 28) and 5'-CATACTCCAAGATCATCGCCAGCA-3' (SEQ ID NO: 41)) (250 nM each) for 18 hours at 50° C. Stringency washes were carried out at 60° C.

Sections were incubated with a mouse monoclonal anti-DIG-HRP overnight at 4° C. and stained using a Tyramide Signal Amplification System (Perkin Elmer, Mass., USA) according to the manufacturer's protocol. Sections were counterstained with Meyer's hematoxylin solution. Negative controls included were samples from non-infected fish from experimental trial, head kidney samples from non-infected fish as a source of immune cells, salmon with pancreatic disease (a differential diagnosis to HSMI), and samples from material sent for diagnostics at random.

Example 7

Statistical Analysis

StatView version 5.0.1 software for Windows (SAS Institute, Cary, N.C., USA) was used for all statistical analyses. Samples without detectable L1 viral gene transcripts were excluded from statistical analysis. Log transformations were performed for all other samples after calculating L1/EF1A ratios (adjusted by a factor of 108). Log-transformed data were retained to facilitate graphical display of group differences, though distributions were not normalized by this method; thus, nonparametric analytic approaches were employed (Mann-Whitney U-test for comparison of healthy and HSMI fish; Kruskal-Wallis for comparisons of healthy and early, middle and peak phase HSMI fish). For all tests, statistical significance was assumed where $p<0.05$.

Example 8

Propagation of Virus in Cell Culture

Syncytium formation and vacuolization can be observed after infecting epithelioma paplosum cyprini (EPC) cells and fat head minnow (FHM) cells with tissue homogenate from HSMI diagnosed fish, however the cytopathic effect (CPE) is rarely seen after 2 to 4 passages.

Example 9

Challenge of Atlantic Salmon

Experimental challenge by injecting Atlantic salmon with material from HSMI diagnosed fish shows pathological changes consistent with HSMI.

Example 10

Electron Microscopy

Virus-like particles of 60 to 80 nm diameter are been observed in necrotic cardiomyocytes diagnosed with HSMI. Chloroform sensitivity analysis shows that PRV belongs to the Reoviridae family, which is a family of naked viruses.

Example 11

Screening of Heart Samples from Experimental Challenge

Heart samples were screened by RT-qPCR for quantification of virus after challenge of Atlantic salmon with tissue homogenate from HSMI diagnosed fish. 10 weeks post challenge (wpc), 4 of 5 fish were positive for the virus (Table 3). The results are consistent with the pathological findings.

TABLE 3

Quantification of virus in heart samples after challange.
Wpc = weeks post challenge.

| Wpc | 0 | 1 | 2 | 3 | 4 | 5 | 6 | 8 | 10 |
|---|---|---|---|---|---|---|---|---|---|
| Positive (Ct) | 0/5 | 1/5 (40) | 1/5 (38) | 0/5 | 0/5 | 0/5 | 0/5 | 1/5 (39) | 4/5 (21-36) |

Example 12

Immunization of Rabbits

Figure 20:
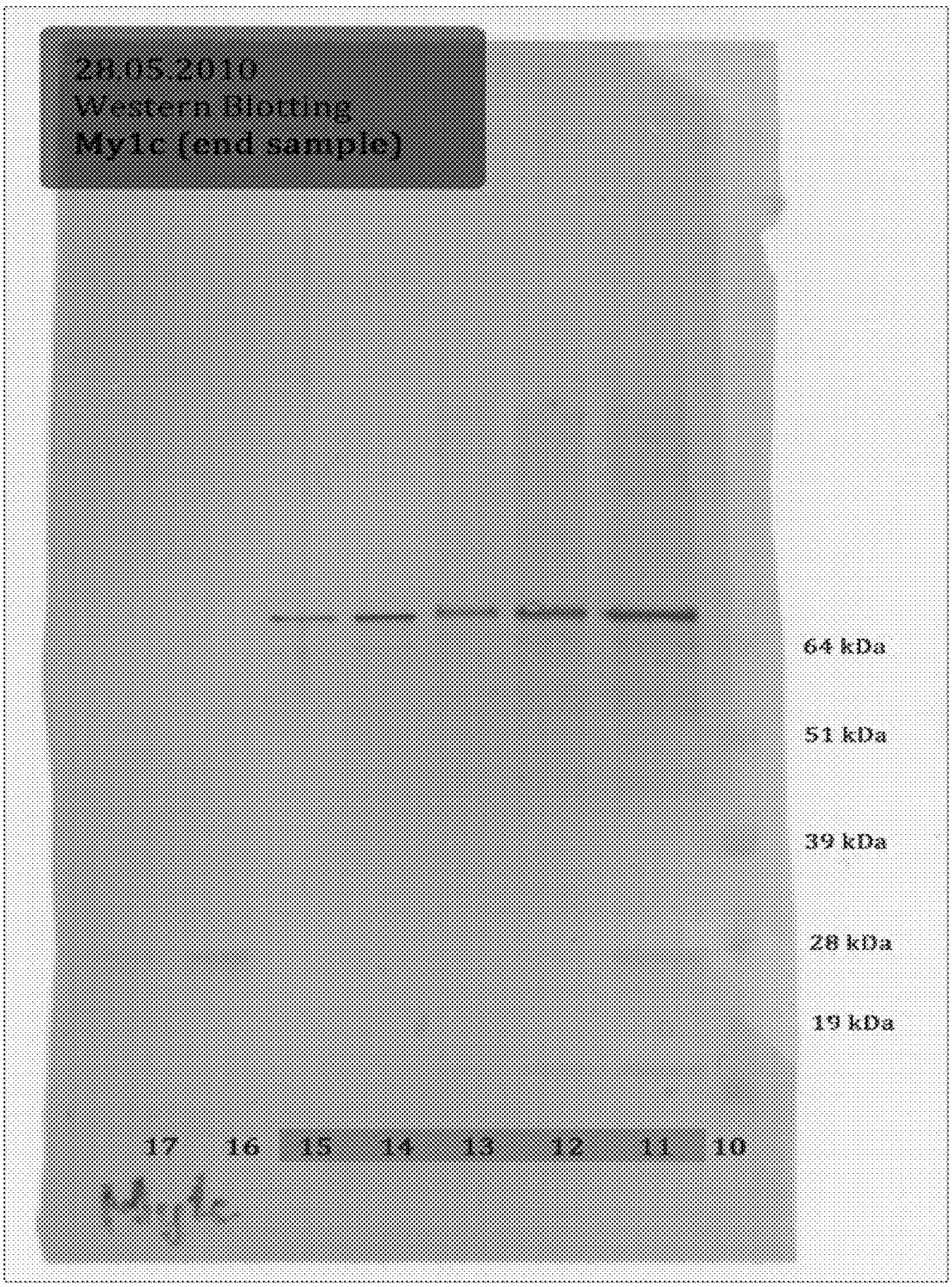
FIG. 20. The antiserum recognizes the μ1C protein as found in Western blots of *E. coli* His-tag fusion protein. Lines 11-13, eluates of purified protein; L14-15, dilutions of pellet of induced bacteria, L16-L17 pellet of non-induced bacteria FIG. 21. The antiserum recognizes the σ2 protein as found in western blots of *E. coli* His-tag fusion protein and different negative controls. Lines 2-4, eluates of purified protein; L5-6, dilutions of pellet of induced bacteria, L7-L8 pellet of non-induced bacteria.

The open reading frame (ORF), minus the 126 first nucleotides, of the M2 genomic segment (SEQ ID NO: 5) encoding the μ1 protein was cloned in the pET100 plasmid and expressed as His-tag fusion protein in *E. coli*, purified. The μl protein is posttranscriptionally cleaved into μ1c in mammalian orthoreovirus in a process wherein 42 aa are removed from the N-terminus of μ1. The protein was used for immunization of a rabbit to obtain polyclonal, μ1C-specific antiserum. The antiserum recognizes the μ1c protein as found in Western blots of *E. coli* His-tag fusion protein and different negative controls (FIG. 20). The antiserum recognizes PRV, as has been shown in immunohistochemistry of hearts of fish with HSMI.

The open reading frame (ORF), from nucleotide 29-1018 of the S1 genomic segment (SEQ ID NO: 2) encoding the σ3 protein (330 amino acids long) (SEQ ID NO: 39) was cloned in the pET101 plasmid and expressed as His-tag fusion protein in *E. coli*, purified and used for immunization for a rabbit to obtain polyclonal, σ3-specific antiserum. The antiserum recognizes the σ3 protein as found in western blots of *E. coli* His-tag fusion protein and different negative controls. The antiserum recognizes native PRV, as has been shown in immunohistochemistry of heart of fish with HSMI.

Figure 21:
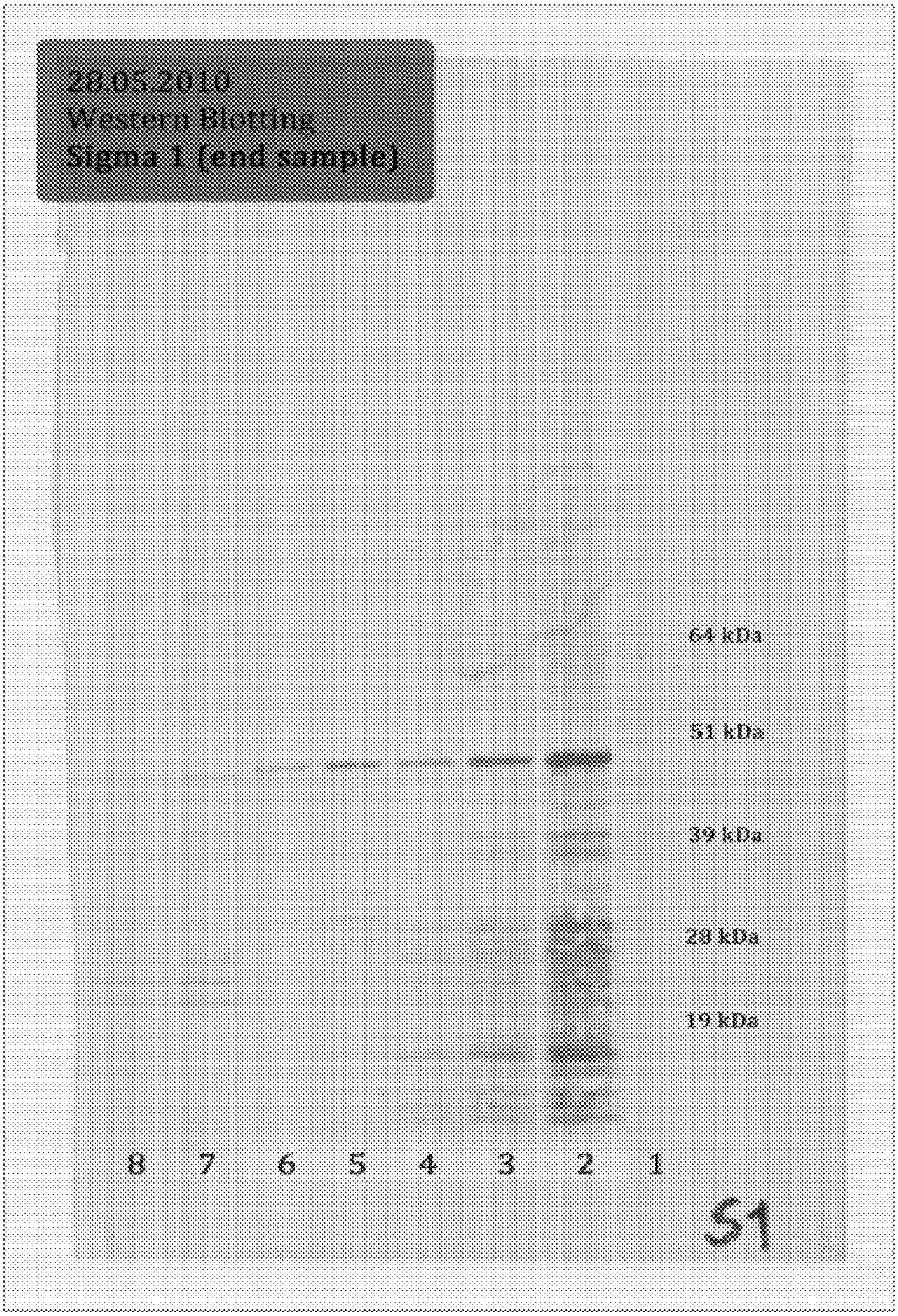
Figure 22:
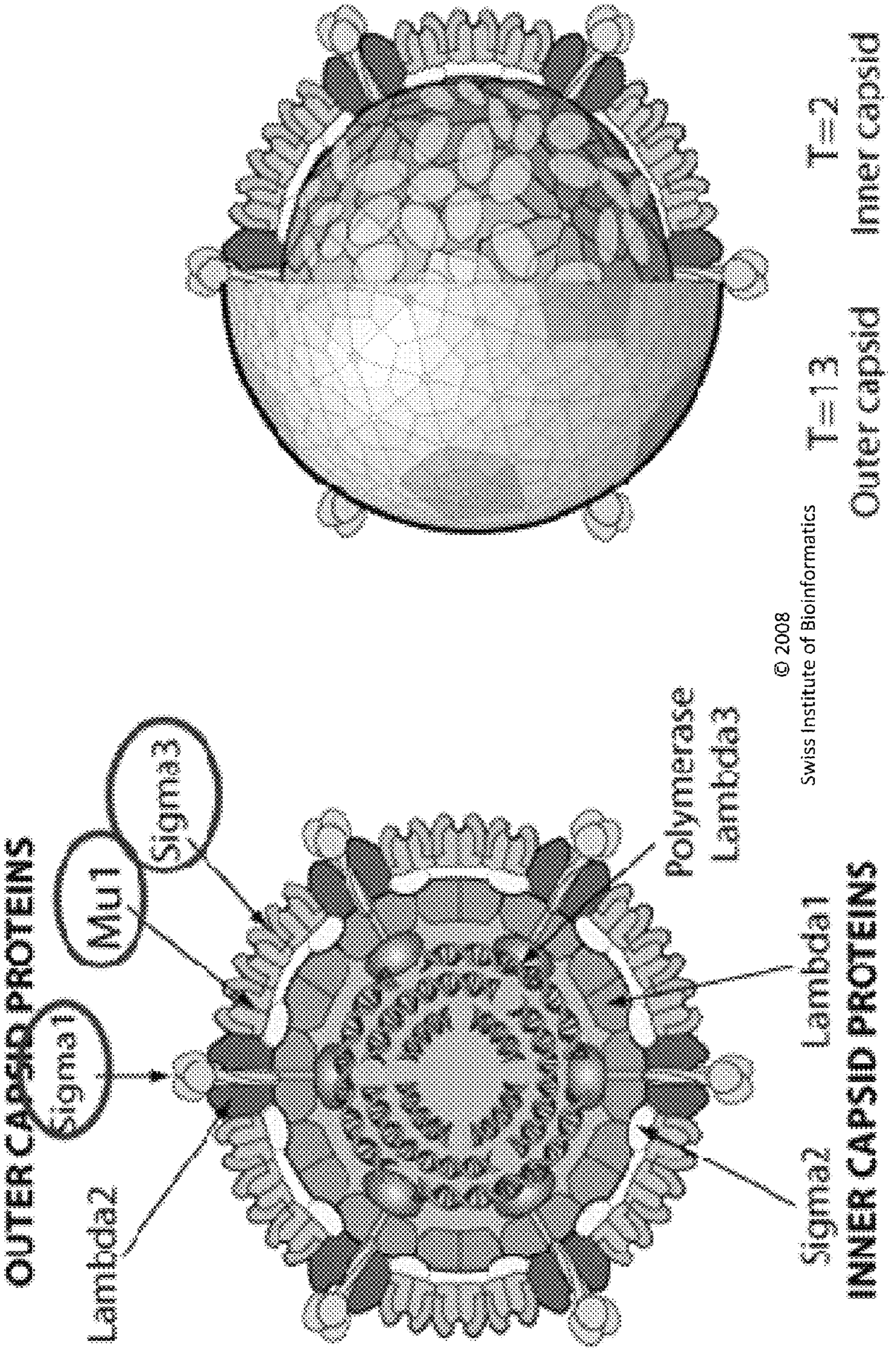
FIG. 22. PRV Illustration.

The open reading frame (ORF), from the nucleotide 22-1281 of the S2 genomic segment (SEQ ID NO: 4) encoding the σ1 protein (420 amino acids long) (SEQ ID NO: 35) was cloned in the pET101 plasmid and expressed as a His-tag fusion protein in *E. Coli*, purified and used for immunization of a rabbit to obtain polyclonal, σ2-specific antiserum. The antiserum recognizes the σ1 protein as found in western blots of *E. coli* His-tag fusion protein (FIG. 21) and in immunohistochemistry of hearts of fish with HSMO.

The open reading frame (ORF), from nucleotide 39-983 of the S4 genomic segment (SEQ ID NO: 3) encoding the σ2 protein (SEQ ID NO: 38) (315 amino acids long) was cloned in the pET100 plasmid and expressed in *E. coli*. Purification of protein is ongoing.

Peptides were synthesized form the amino acid sequences of assumed antigenic region from the fusion-associated small transmembrane protein (FAST) protein (SEQ ID NO: 40) encoded by S1 (SEQ ID NO: 2) (nucleotide 108-479, +1 frame relative to the ORF of σ3) and was used for immunization of a rabbit to obtain polyclonal FAST-specific antiserum. Currently it is being tested by immunohistochemistry of hearts of fish with HSMI of the antiserum recognizes PRV infected cells.

Rabbits were immunized ($3^{rd}$ booster) with recombinant proteins expressed in *E. coli*. The outer capsid proteins sigma-1 (SEQ ID NO: 35), sigma-3 (SEQ ID NO: 37) and mu-1C (SEQ ID NO: 33) were expressed and injected, in addition to a synthetic peptide of the FAST protein of S1 (SEQ ID NO: 40). Specific antibodies targeting the FAST protein can increase chances of culturing the virus, as the FAST protein is involved in syncytium formation.

The sera raised against the μ1, σ3 and putative σ2 proteins all give positive signals in immunohistochemistry of hearts from salmon with HSMI. The serum against the μ1 protein works best and gives a good signal to noise ratio in immunohistochemistry.

TABLE 4

Annotation of ORFS proteins. Based on in silico analysis.

| Genomic Segment of PRV | PRV Proteins | PRV Protein SEQ ID NO | Putative Function of PRV Compared to MRV, ARV and GCRV |
|---|---|---|---|
| L3 (SEQ ID NO: 9) | λ3, 144.3 kDa, 1286 aa | SEQ ID NO: 31 | RNA-dependent RNA polymerase |
| L2 (SEQ ID NO: 10) | λ2, 143.7 kDa, 1290 aa | SEQ ID NO: 30 | Guanylyltransferase, methyltransferase |
| L1 (SEQ ID NO: 8) | λ1, 141.1 kDa, 1282 aa | SEQ ID NO: 29 | Helicase, NTPase |
| M1 (SEQ ID NO: 6) | μ2, 86.1 kDa, 760 aa | SEQ ID NO: 33 | NTPase |
| M2 (SEQ ID NO: 5) | μ1, 74.2 kDa, 687 aa | SEQ ID NO: 32 | Outer capsid |
| M3 (SEQ ID NO: 7) | μNS, 83.5 kDa, 752 aa | SEQ ID NO: 34 | dsRNA binding |
| S2 (SEQ ID NO: 4) | σ1, 45.9 kDA, 420 aa (S2 ORF 1) | SEQ ID NO: 35 | Inner capsid |
| S2 (SEQ ID NO: 4) | σ1s, 10.9 kDa, 71aa (S2 ORF 2) | SEQ ID NO: 36 | Inner capsid |
| S4 (SEQ ID NO: 3) | σ2, 34.6 kDa, 315 aa | SEQ ID NO: 38 | Cell attachment, primary serotype determinant |
| S3 (SEQ ID NO: 1) | σNS, 39.1 kDa, 354 aa | SEQ ID NO: 37 | dsRNA binding |
| S1 (SEQ ID NO: 2) | σ3 37.0 kDa, 330 aa (S1 ORF 1) | SEQ ID NO: 39 | Zinc mettaloprotein |
| S1 (SEQ ID NO: 2) | FAST 13.0 kDa, 124 aa (S1 ORF 2) | SEQ ID NO: 40 | FAST protein |

Example 13

Virus Characterization and Virulence Studies

PRV virus segments were cloned and expressed in insect and fish cell lines to examine potential virulence factors virus characterization and virulence studies. The hemagglutinating properties of the virus will also be tested and samples from geographically distant areas will be sequenced to study potential differences and strain variations.

Example 14

Screening of Wild Fish and Fertilized Eggs

Material from the National Gene Bank will be screened for presence of the virus in wild salmon populations and examined for possible vertical transfer of virus.

Example 15

Screening of Brood Stocks

Material for screening of brood stocks kept under different conditions can be obtained, inter alia, from one or more commercial breeding companies.

REFERENCES

Kongtorp, R. T., Kjerstad, A., Taksdal, T., Guttvik, A. & Falk, K. Heart and skeletal muscle inflammation in Atlantic salmon, Salmo salar L: a new infectious disease. J Fish Dis 27, 351-358, doi:10.1111/j.1365-2761.2004.00549.xJFD549 [pii] (2004).

Ferguson, H. W., Kongtorp, R. T., Taksdal, T., Graham, D. & Falk, K. An outbreak of disease resembling heart and skeletal muscle inflammation in Scottish farmed salmon, Salmo salar L., with observations on myocardial regeneration. J Fish Dis 28, 119-123, doi:JFD602 [pii] 10.1111/j.1365-2761.2004.00602.x (2005).

Kongtorp, R. T., Taksdal, T. & Lyngoy, A. Pathology of heart and skeletal muscle inflammation (HSMI) in farmed Atlantic salmon Salmo salar. Dis Aquat Organ 59, 217-224 (2004).

Watanabe, K. et al. Virus-like particles associated with heart and skeletal muscle inflammation (HSMI). Dis Aquat Organ 70, 183-192 (2006).

Margulies, M. et al. Genome sequencing in microfabricated high-density picolitre reactors. Nature 437, 376-380 (2005).

Altschul, S. F., Gish, W., Miller, W., Myers, E. W. & Lipman, D. J. Basic local alignment search tool. J Mol Biol 215, 403-410, doi:10.1006/jmbi.1990.9999 S0022283680799990 [pii] (1990).

Pearson, W. R., Wood, T., Zhang, Z. & Miller, W. Comparison of DNA sequences with protein sequences. Genomics 46, 24-36, doi:S0888-7543(97)94995-8 [pii] 10.1006/geno.1997.4995 (1997).

Trifonov, V. & Rabadan, R. Frequency analysis techniques for discovery of novel microorganisms. mBio (submitted).

Attoui, H. et al. Common evolutionary origin of aquareoviruses and orthoreoviruses revealed by genome characterization of Golden shiner reovirus, Grass carp reovirus, Striped bass reovirus and golden ide reovirus (genus Aquareovirus, family Reoviridae). J Gen Virol 83, 1941-1951 (2002).

Shmulevitz, M. & Duncan, R. A new class of fusion-associated small transmembrane (FAST) proteins encoded by the non-enveloped fusogenic reoviruses. EMBO J 19, 902-912, doi:10.1093/emboj/19.5.902 (2000).

Pfaffl, M. W. A new mathematical model for relative quantification in real-time RT-PCR. Nucleic Acids Res 29, e45 (2001).

Kongtorp, R. T., Halse, M., Taksdal, T. & Falk, K. Longitudinal study of a natural outbreak of heart and skeletal muscle inflammation in Atlantic salmon, Salmo salar L. J Fish Dis 29, 233-244, doi:JFD710 [pii] 10.1111/j.1365-2761.2006.00710.x (2006).

Jones, R. C. Avian reovirus infections. Rev Sci Tech 19, 614-625 (2000).

Thompson, J. D., Gibson, T. J. & Higgins, D. G. Multiple sequence alignment using ClustalW and ClustalX. Curr Protoc Bioinformatics Chapter 2, Unit 23, doi:10.1002/0471250953.bi0203s00 (2002).

Tamura, K., Dudley, J., Nei, M. & Kumar, S. MEGA4: Molecular Evolutionary Genetics Analysis (MEGA) software version 4.0. Mol Biol Evol 24, 1596-1599, doi: msm092 [pii] 10.1093/molbev/msm092 (2007).

Notredame, C., Higgins, D. G. & Heringa, J. T-Coffee: A novel method for fast and accurate multiple sequence alignment. J Mol Biol 302, 205-217, doi:10.1006/jmbi.2000.4042 S0022-2836(00)94042-7 [pii] (2000).

Mertens, P., Attoui, H., Duncan, R. & Dermody, T. Family Reoviridae. 447-454 (Elsevier Academic Press, 2005).

Kongtorp, R. T. & Taksdal, T. Studies with experimental transmission of heart and skeletal muscle inflammation in Atlantic salmon, Salmo salar L. J Fish Dis 32, 253-262, doi:JFD983 [pii] 10.1111/j.1365-2761.2008.00983.x (2009).

Palacios, G. et al. Panmicrobial oligonucleotide array for diagnosis of infectious diseases. Emerg Infect Dis 13, 73-81 (2007).

Palacios, G. et al. A new arenavirus in a cluster of fatal transplant-associated diseases. N Engl J Med 358, 991-998, doi:NEJMoa073785 [pii] 10.1056/NEJMoa073785 (2008).

Cox-Foster, D. L. et al. A metagenomic survey of microbes in honey bee colony collapse disorder. Science 318, 283-287, doi:1146498 [pii] 10.1126/science. 1146498 (2007).

Olsvik, P. A., Lie, K. K., Jordal, A. E., Nilsen, T. O. & Hordvik, I. Evaluation of potential reference genes in real-time RT-PCR studies of Atlantic salmon. BMC Mol Biol 6, 21, doi:1471-2199-6-21 [pii] 10.1186/1471-2199-6-21 (2005).

Kongtorp R. T., Taksdal T. & Lyngoy A. (2004b) Pathology of heart and skeletal muscle inflammation (HSMI) in farmed Atlantic salmon Salmo salar. Diseases of Aquatic Organisms 59, 217-224.

Kongtorp R. T., Kjerstad A., Guttvik A., Taksdal T. & Falk K. (2004a) Heart and skeletal muscle inflammation in Atlantic salmon, Salmo salar L.: a new infectious disease. Journal of Fish Diseases 27, 351-358.

Eliassen T. M., Solbakk I. T., Evensen Ø. & Gravningen K. (2004) Isolation of heart and poster skeletal muscle inflammation virus (HSMIV) from salmon. 6th International Symposium on Viruses of Lower Vertebrates, Hokkaido, Japan.

Watanabe K., Karlsen M., Devold M., Isdal E., Litlabo A. & Nylund A. (2006) Virus-like particles associated with heart and skeletal muscle inflammation (HSMI). Diseases of Aquatic Organisms 70, 183-192.

Kongtorp R. T., Halse M., Taksdal T. & Falk K. (2006) Longitudinal study of a natural outbreak of heart and skeletal muscle inflammation in Atlantic salmon, Salmo salar L. Journal of Fish Diseases 29, 233-244.

Studies with experimental transmission of heart and skeletal muscle inflammation in Atlantic salmon, Salmo salar L. Kongtorp R T, Taksdal T. J Fish Dis. 2009 Mar;32(3):253-62. Epub 2009 Feb 18. PMID: 19236557

What is claimed is:

1. A cDNA probe comprising from about 10 nucleotides to about 50 nucleotides, wherein at least about 10 contiguous nucleotides are at least 95% complementary to a nucleic acid target region within a nucleic acid sequence of SEQ ID NO: 2.

2. The cDNA probe of claim 1, wherein the probe is at least about 95.5%, about 96%, about 96.5%, about 97%, about 97.5%, about 98%, about 98.5%, about 99%, about 99.5% or about 99.9% complementary to SEQ ID NO: 2.

3. The cDNA probe of claim 2, wherein the cDNA probe consists essentially of from about 10 to about 50 nucleotides.

4. A cDNA fragment which has a sequence consisting essentially of from about 10 to about 30 consecutive nucleotides from a nucleic acid sequence of SEQ ID NO: 2.

5. A method for detecting the presence of piscine reovirus (PRV) in a biological sample, the method comprising:

a) contacting nucleic acid from a biological sample with at least one primer which is a cDNA fragment which has a sequence consisting essentially of from about 10 to about 30 consecutive nucleotides from a nucleic acid sequence of SEQ ID NO: 2, b) subjecting the nucleic acid and the primer to amplification conditions, and c) detecting the presence of amplification product, wherein the presence of amplification product indicates the presence of RNA associated with PRV in the sample.

6. A cDNA fragment which has a sequence consisting essentially of from about 10 to about 30 consecutive nucleotides from a nucleic acid sequence which is complementary to a nucleic acid sequence of SEQ ID NO: 2.

7. The method of claim 5, wherein the sample is from a teleost.

8. The method of claim 7, wherein the teleost is a salmon.

* * * * *